(12) United States Patent
Yin et al.

(10) Patent No.: US 12,121,510 B2
(45) Date of Patent: *Oct. 22, 2024

(54) COMPOUNDS AND METHODS TO SENSITIZE CANCER CELLS TO CISPLATIN

(71) Applicants: Cedars-Sinai Medical Center, Los Angeles, CA (US); Da Zen Theranostics, Inc., Beverly HIlls, CA (US)

(72) Inventors: Liyuan Yin, Los Angeles, CA (US); Yi Zhang, Los Angeles, CA (US); Stefan Mrdenovic, Osijek (HR); Gina Chia Yi Chu, Los Angeles, CA (US); Ruoxiang Wang, Los Angeles, CA (US); Qinghua Zhou, Chengdu (CN); Jian Zhang, Ann Arbor, MI (US); Leland W. K. Chung, Beverly Hills, CA (US)

(73) Assignees: Da Zen Theranostics, Inc., San Jose, CA (US); Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/343,697

(22) PCT Filed: Oct. 21, 2017

(86) PCT No.: PCT/US2017/057762
§ 371 (c)(1),
(2) Date: Apr. 19, 2019

(87) PCT Pub. No.: WO2018/075994
PCT Pub. Date: Apr. 26, 2018

(65) Prior Publication Data
US 2019/0262312 A1   Aug. 29, 2019

Related U.S. Application Data

(60) Provisional application No. 62/410,960, filed on Oct. 21, 2016.

(51) Int. Cl.
*A61P 35/00* (2006.01)
*A61K 31/22* (2006.01)
(Continued)

(52) U.S. Cl.
CPC ............ *A61K 31/404* (2013.01); *A61K 31/22* (2013.01); *A61K 31/282* (2013.01); *A61K 31/337* (2013.01); *A61K 31/351* (2013.01); *A61K 31/357* (2013.01); *A61K 31/366* (2013.01); *A61K 31/40* (2013.01); *A61K 31/4045* (2013.01); *A61K 31/47* (2013.01); *A61K 31/505* (2013.01); *A61K 31/513* (2013.01); *A61K 31/519* (2013.01); *A61K 31/5377* (2013.01); *A61K 31/555* (2013.01); *A61K 31/65* (2013.01); *A61K 31/704* (2013.01);
(Continued)

(58) Field of Classification Search
CPC ...................................................... A61P 35/00
See application file for complete search history.

(56) References Cited

U.S. PATENT DOCUMENTS 6,376,537 B1   4/2002   Weinberg
7,198,778 B2   4/2007   Achilefu et al.
(Continued)

FOREIGN PATENT DOCUMENTS

CN      104312194 A      1/2015
WO    2009152440 A1    12/2009
(Continued)

OTHER PUBLICATIONS

Partial European Supplementary Search Report from European Patent Application No. 17862099.3 dated Sep. 1, 2020.
Boyang Wu et al., "Near-Infrared fluorescence heptamethine carbocyanine dyes mediate imaging and targeted drug delivery for human brain tumor," Biomaterials, Oct. 1, 2015, vol. 67, pp. 1-10.
Boyang Wu et al., "Supplementary Data Near-Infrared Fluorescence Heptamethine Carbocyanine Dyes Mediate Imaging and Targeted Drug Delivery for Human Brain Tumor," Appendix A, Oct. 1, 2015, https://ars.els-cdn.com/content/image/1-s2.0-S0142961215006109-mmc1.pdf.
(Continued)

*Primary Examiner* — John S Kenyon
(74) *Attorney, Agent, or Firm* — McCarter & English, LLP; Michael J. DeGrazia

(57) ABSTRACT

The present invention generally relates to sensitizer compounds and their use to sensitize cancer and/or pre-cancerous cells of certain cancers to treatment with certain resistance-prone therapeutics used in cancer therapy. In embodiments, the conjugates of particular esters or amides of Near Infrared Dyes, are used as sensitizers to avoid or overcome therapeutic resistance once formed. In embodiments, the sensitizers include conjugates with Cisplatin, Simvastatin, Artemisinin, platin-based compounds or statins. In embodiments, the resistance prone cancer therapeutics include cisplatin, gemcitabine, doxorubicin, paclitaxel, docetaxel, and platin-based compounds. These may be administered in combination with the sensitizer, or the sensitizer itself may comprise an therapeutic-derived moiety conjugated to the sensitizer, for example as is the case for dye-CIS conjugated sensitizers. Alternatively, the sensitizer may be co-administered with one or more therapeutic. Embodiments of the invention may advantageously be used in cancers that have a tendency to develop resistance to such cancer therapeutics and/or to form metastases, including e.g. lung, pancreatic, prostate, testicular, ovarian, cervical, bladder, breast, head and neck, esophageal, and stomach, cancers, germ cell tumors, lymphomas and other cancers.

19 Claims, 31 Drawing Sheets

(51) Int. Cl.

| | | |
|---|---|---|
| A61K 31/282 | (2006.01) | |
| A61K 31/337 | (2006.01) | |
| A61K 31/351 | (2006.01) | |
| A61K 31/357 | (2006.01) | |
| A61K 31/366 | (2006.01) | |
| A61K 31/40 | (2006.01) | |
| A61K 31/404 | (2006.01) | |
| A61K 31/4045 | (2006.01) | |
| A61K 31/47 | (2006.01) | |
| A61K 31/505 | (2006.01) | |
| A61K 31/513 | (2006.01) | |
| A61K 31/519 | (2006.01) | |
| A61K 31/5377 | (2006.01) | |
| A61K 31/555 | (2006.01) | |
| A61K 31/65 | (2006.01) | |
| A61K 31/704 | (2006.01) | |
| A61K 31/7068 | (2006.01) | |
| A61K 33/243 | (2019.01) | |
| A61K 47/52 | (2017.01) | |
| A61K 47/54 | (2017.01) | |
| A61K 47/55 | (2017.01) | |
| A61K 49/00 | (2006.01) | |
| A61P 35/04 | (2006.01) | |
| C07D 209/10 | (2006.01) | |
| C07D 405/14 | (2006.01) | |
| C07D 493/18 | (2006.01) | |
| C09B 23/01 | (2006.01) | |
| A61K 45/06 | (2006.01) | |

(52) U.S. Cl.
CPC ........ *A61K 31/7068* (2013.01); *A61K 33/243* (2019.01); *A61K 47/52* (2017.08); *A61K 47/545* (2017.08); *A61K 47/55* (2017.08); *A61K 49/0004* (2013.01); *A61K 49/0032* (2013.01); *A61P 35/00* (2018.01); *A61P 35/04* (2018.01); *C07D 209/10* (2013.01); *C07D 405/14* (2013.01); *C07D 493/18* (2013.01); *C09B 23/0016* (2013.01); *C09B 23/0066* (2013.01); *A61K 45/06* (2013.01)

(56) References Cited

U.S. PATENT DOCUMENTS

| | | | |
|---|---|---|---|
| 9,771,625 | B2 | 9/2017 | Shih et al. |
| 10,307,489 | B2 * | 6/2019 | Chung .................... A61P 35/00 |
| 2002/0151583 | A1 | 10/2002 | Weinberg |
| 2003/0232033 | A1 | 12/2003 | Cantrell |
| 2012/0219570 | A1 | 8/2012 | Chang et al. |
| 2013/0039854 | A1 | 2/2013 | Shih et al. |
| 2013/0101513 | A1 | 4/2013 | Yang et al. |
| 2014/0248213 | A1 | 9/2014 | Chung et al. |
| 2014/0323551 | A1 | 10/2014 | Chung et al. |
| 2015/0209361 | A1 | 7/2015 | Shih et al. |
| 2019/0262312 | A1 | 8/2019 | Yin et al. |
| 2019/0269783 | A1 * | 9/2019 | Yin ...................... A61K 33/243 |
| 2019/0269801 | A1 * | 9/2019 | Chung ................ C09B 23/0016 |
| 2022/0031855 | A1 * | 2/2022 | Chung ................ C09B 23/0066 |

FOREIGN PATENT DOCUMENTS

| | | | |
|---|---|---|---|
| WO | 2013016580 A2 | 1/2013 | |
| WO | 2013052776 A1 | 4/2013 | |
| WO | 2014086942 A1 | 6/2014 | |
| WO | 2015188934 A1 | 12/2015 | |
| WO | WO-2016106324 A1 * | 6/2016 | .............. A61P 35/00 |
| WO | 2018075993 A1 | 4/2018 | |
| WO | 2018075994 A1 | 4/2018 | |
| WO | 2018075996 A1 | 4/2018 | |

OTHER PUBLICATIONS

Yang Guan et al., "Improving Therapeutic Potential of Farnesylthiosalicylic Acid: Tumor Specific Delivery via Conjugation with Heptamethine Cyanine Dye," Molecular Pharmaceutics, Mar. 21, 2016, vol. 14, No. 1, pp. 1-13.
Ki-Eun Hwang et al., "Effect of simvastatin on the resistance of EGFR tyrosine kinase inhibitors in a non-small cell lung cancer with the T790M mutation of EGFR," Experimental Cell Research, May 1, 2014, vol. 323, No. 2, pp. 288-296.
Partial European Supplementary Search Report from European Patent Application No. 17862097.7 dated May 27, 2020.
Wu et al., Near-Infrared Fluorescence and nuclear imaging and targeting of prostate cancer, Trans. Androl. Urol. 2013, 2, 254-264.
Zhang, E. et al., "Mechanistic study of IR-780 dye as a potential tumor targeting and drug delivery agent," Biomaterials, Jan. 2014, vol. 35, No. 2, pp. 771-778, p. 776, FIG 5A, p. 777, 3.5.
Yang, Z. et al., "Folate-based near-infrared fluorescent theranostic gemcitabine delivery," J. Am. Chem. Soc., Aug. 7, 2013, vol. 135, No. 31, pp. 11657-11662.
Xiao, L. et al., Heptamethine cyanine based (64)Cu-PET probe PC-1001 for cancer imaging: synthesis and in vivo evaluation, Nucl. Med. Biol., Apr. 2013, vol. 40, No. 3, pp. 351-360.
International Search Report published with WO2016106324 (PCT/US2015/067393).
International Search Report published with WO2018075994 (PCT/US2017/057762).
International Search Report published with WO2018075996 (PCT/US2017/057765).
International Search Report published with WO2018075993 (PCT/US2017/057761).
Partial Supplementary European Search Report from European Patent Application No. 17861447.5, dated Jan. 25, 2021.
National Cancer Institute, "Erlotinib Hydrochloride," Oct. 5, 2006, https://www.cancer.gov/about-cancer/treatment/drugs/erlotinibhydrochloride.
"Kinase Inhibitors for Cancer Treatment—Chemotherapy," Apr. 24, 2010, https://chemoth.com/types/kinaseinhibitors.
Supplemental European Search Report dated May 28, 2021 for European Patent Application No. 17861447.5.

* cited by examiner

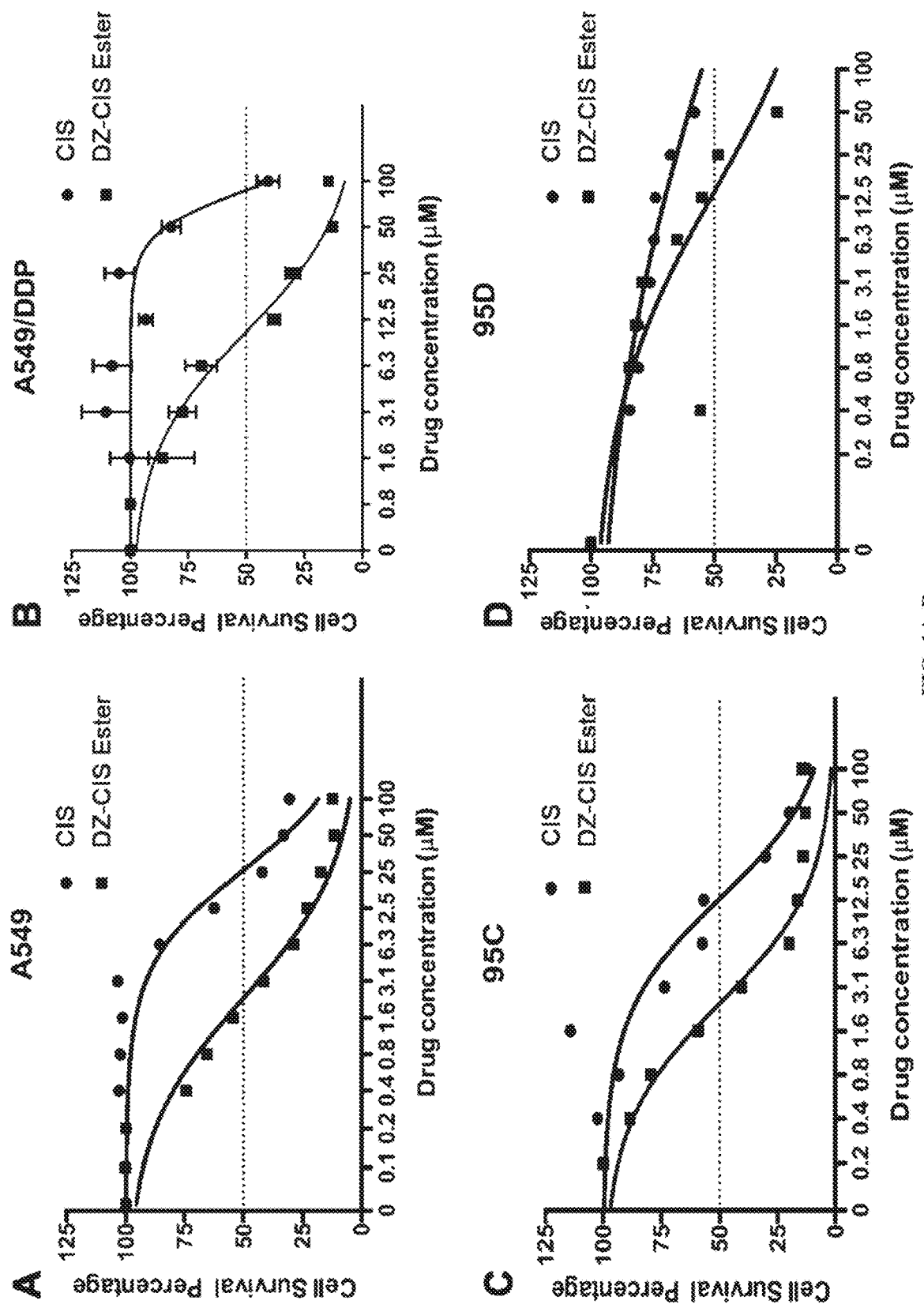
FIG. 1A-B

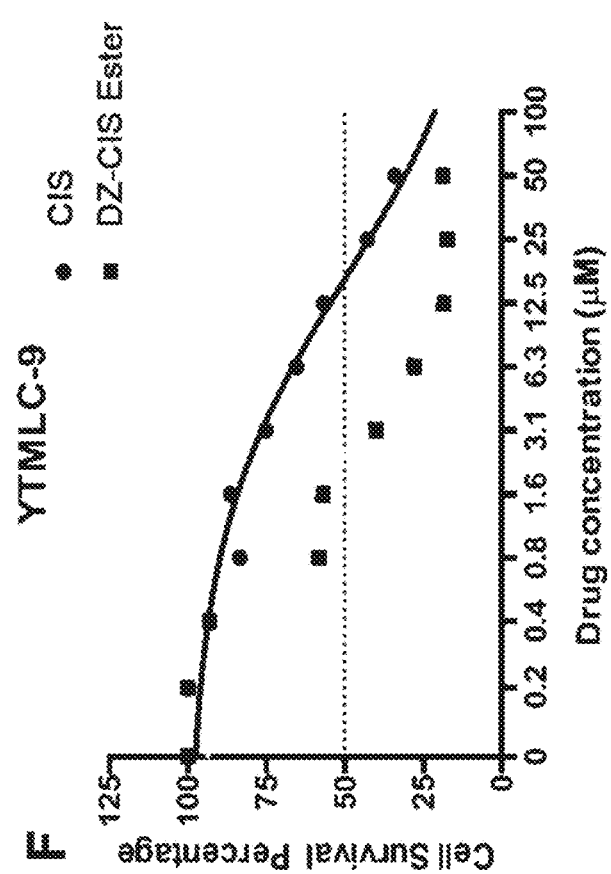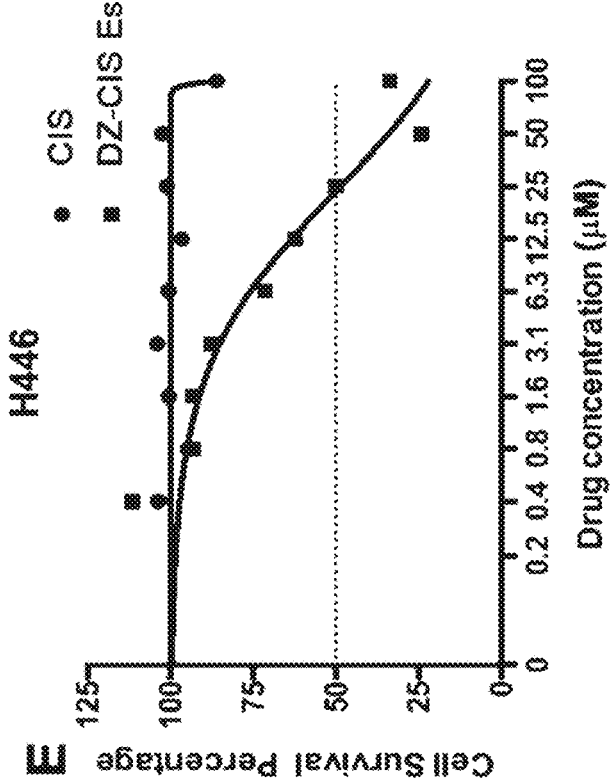
FIG. 1E-F

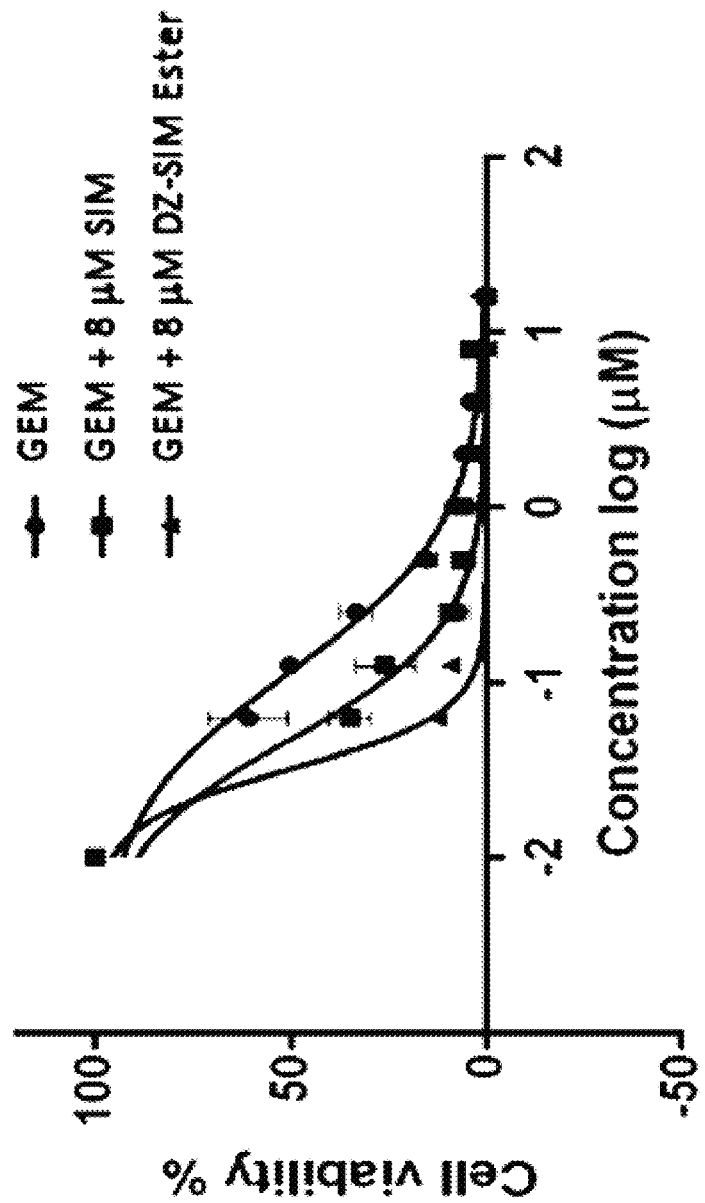
FIG. 3B1

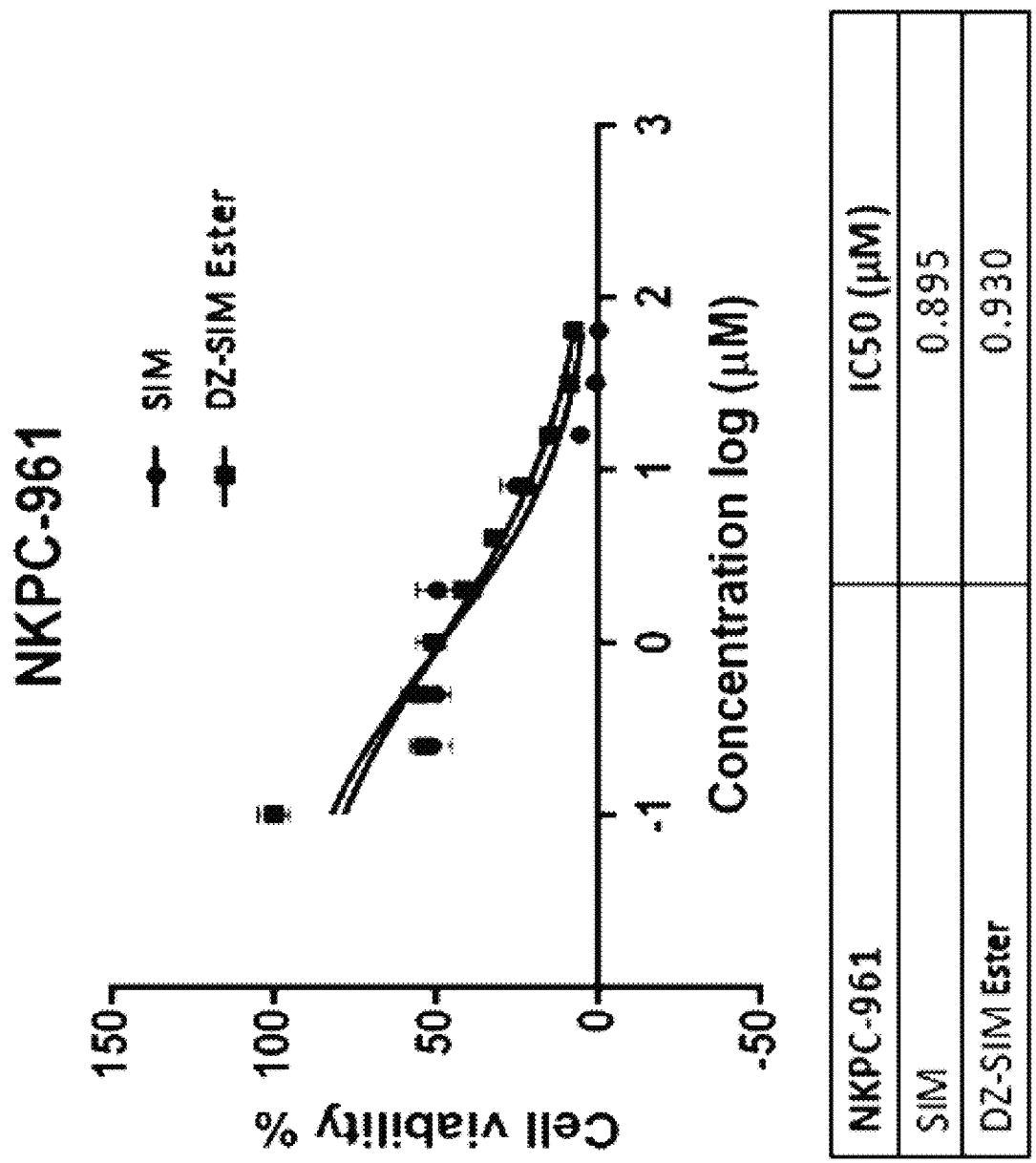
FIG. 3B2

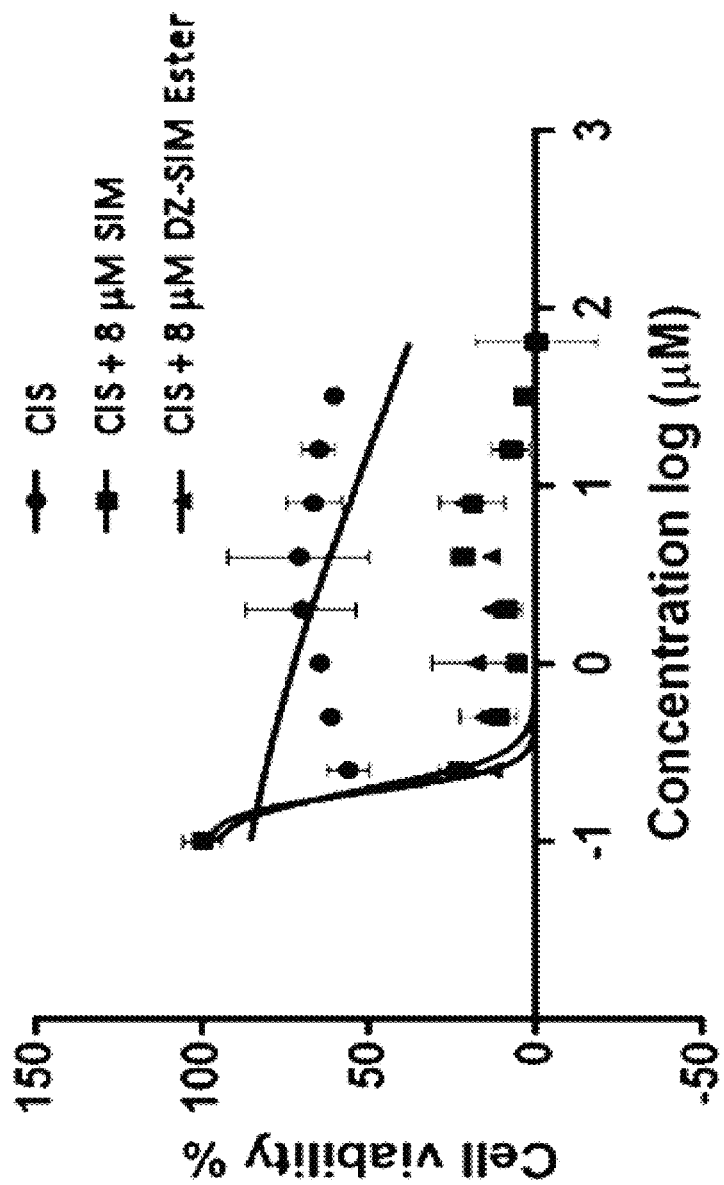
FIG. 3B3

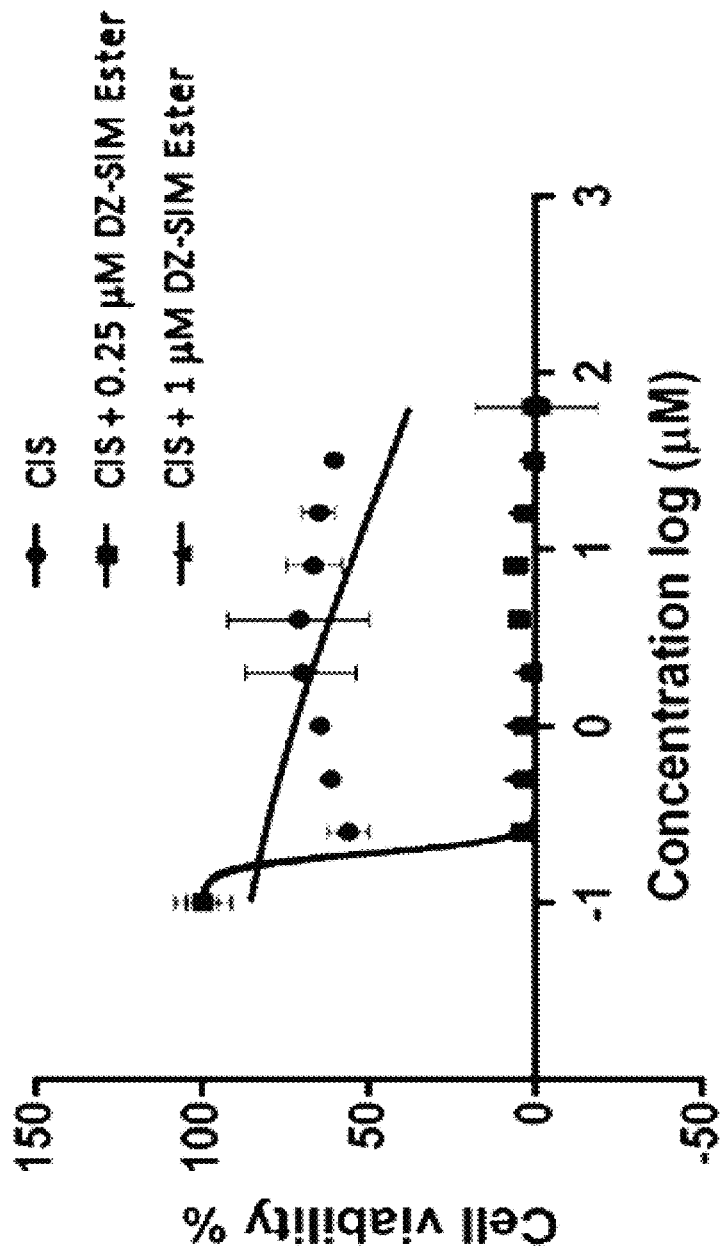
FIG. 3B4

／ Tubular dilatation ▲ Intratubular debris ＊ Tubular cell necrosis

COMPOUNDS AND METHODS TO SENSITIZE CANCER CELLS TO CISPLATIN

FIELD OF THE INVENTION

The present invention generally relates to sensitizer compounds and their use to sensitize cancer and/or pre-cancerous cells of certain cancers to treatment with certain resistance-prone therapeutics (RPTs) used in cancer therapy. In embodiments, the conjugates of particular esters or amides of Near Infrared Dyes (NIR Dyes), referred to herein as DZ-amide or ester conjugates, are used as sensitizers to avoid resistance to RPTs or to overcome drug resistance once formed. In embodiments, the sensitizers include DZ-conjugates with either Cisplatin (CIS), Simvastatin (SIM), or Artemisinin (ART). In embodiments, the RPTs include cisplatin (CIS), gemcitabine (GEM), doxorubicin (DOX), paclitaxel (PAC or PTX), docetaxel (DT), and platin-based compounds (PT). The RPTs may be administered in combination with the sensitizer, or the sensitizer itself may comprise an RPT-derived moiety conjugated to the sensitizer, for example as is the case for the DZ-CIS amide/ester sensitizer. Alternatively, the sensitizer may be co-administered with one or more of CIS, GEM, DOX, PAC DT, or PT. Embodiments of the invention may advantageously be used in cancers that have a tendency to develop resistance to such cancer therapeutics and/or to form metastases, including e.g. lung, pancreatic, prostate, testicular, ovarian, cervical, bladder, breast, head and neck, esophageal, and stomach, cancers, germ cell tumors, lymphomas and other cancers.

CROSS-REFERENCE TO RELATED APPLICATIONS

This is an application filed under 35 USC § 371 of PCT/US2017/057762, filed on Oct. 21, 2017, claiming priority to U.S. 62/410,960, filed on Oct. 21, 2016, each of which is herein incorporated by reference in its entirety.

BACKGROUND OF THE INVENTION

Various cancer therapeutics, especially those used for the most aggressive and/or metastatic cancers, are known to be associated with the development of resistance during therapy, and allow or even induce the development of resistance. Such resistance-prone therapeutics (RPTs) include Cisplatin (CIS), gemcitabine (GEM), doxorubicin (DOX), paclitaxel (PAC), and docetaxel (DT).

Cisplatin (CIS) and its derivatives or their combination therapies with other drugs are used for treatment of certain cancers, in particular of advanced or metastatic cancers, or cancers that typically develop metastases. In particular, CIS is used for cancers including lung, small cell lung, non-small cell lung, testicular, ovarian, bladder, head and neck, esophageal, breast, cervical, stomach and prostate cancers. Treatment options for these cancers, in particular of their advanced/metastatic forms, are limited, and these cancer types often develop resistance to treatment with CIS. CIS has been combined with various other drugs, for example, statins including Simvastatin have been used in combination with Cisplatin, but often with limited success.

Similarly, gemcitabine (GEM), doxorubicin (DOX), paclitaxel (PAC), and docetaxel (DT) have been used for treatment of various cancers such as the above and/or including advanced/metastatic forms and those with tendencies to develop therapeutic resistance.

Presently known strategies for cancer therapy employ various drug combinations to increase sensitivity of cancer cells to chemotherapeutic drugs and/or overcoming resistance to such drugs. These include statins such as Simvastatin. However, known approaches often lack sufficient effect, inacceptable side effect, benefits may be limited to very specific cancer cell types (cell types, tissue types, subtypes, phenotypes), and/or studies show inconsistent effectiveness with only some patients benefiting, and others even showing worse outcomes.

Near infrared (NIR) dye cancer drug conjugates are generally known for their capabilities to preferentially target some cancer drugs to cancer cells. However, NIR dye conjugates have not been known to consistently increase sensitivity to CIS, GEM, DOX, PAC or DT in cancer or tumor cells, or to overcome therapeutic resistance to these therapeutics. Further, sufficiently increasing the sensitivity of cancer cells, and avoiding or overcoming their therapeutic resistance, has not been possible with prior art methods.

The present approaches are lacking in effectiveness, are accompanied by sometimes severe side effects that may limit the therapeutical dose, or both. Furthermore, present approaches are either not able to lower the half maximal inhibitory concentration (IC50), or are not able to lower the IC50 sufficiently to provide an effective therapy and/or acceptable side effects.

Therefore, there is a need in the art for improved approaches to sensitize cancer cells to RPTs (CIS, GEM, DOX, PAC or DT), and avoid or overcome resistance to these resistance-prone therapeutics. Further, there is a need in the art for therapeutics with less side effects. Still further, there is a need for therapeutics that kill cancer cells more effectively at the same dose, or allow to lower a given dose. Also there is a need for therapeutics that reduce tumor volume, or an reduce the increase thereof. In particular, there is a need for such therapeutics for patients with cancer cells or tumors that are resistant to RPTs, and especially patients that have already undergone therapy with these therapeutics, and developed resistance. Also, there is a need for a novel therapeutic that is effective and/or has lesser side effects, and that has these advantages consistently in different cancer or tumor types. Particularly there is a need for sensitizers that overcome or avoid resistance to RPTs in cancer cells or tumors resistant to these therapeutics, or prone to develop such resistance. Still further there is a need for sensitizers to overcome or avoid resistance to RPTs in lung cancer, non-small cell lung cancer (NSCLC), small cell lung cancer, pancreatic cancer, lymphomas, kidney or renal cancer, prostate cancer, ovarian cancer, testicular cancer, cervical cancer, bladder cancer, breast cancer, head and neck cancer, esophageal cancer, stomach cancer, germ cell cancer, and other cancers. Further yet there is a need to provide a therapeutic that is able to significantly reduce the IC50 of CIS, GEM, DOX, PAC or DT, or itself provide a significantly lower IC50 compared to these RPTs. Still further there is a need to provide sensitizers that have sufficient solubility and stability. Also there is a need for sensitizers that enter cancer cells, enter cancer cells more quickly, accumulate faster and/or to a higher concentration. These and other features and advantages of the present invention will be explained and will become apparent to one skilled in the art through the summary of the invention that follows.

SUMMARY OF THE INVENTION

Surprisingly it has been found that certain NIR dye conjugates, in particular certain DZ-DRG ester and amide conjugates disclosed herein, have a sensitizing effect on tumor, cancer or pre-cancerous cells, and for example, makes them sensitive to RPTs, reduces the necessary RPT dose, overcomes cellular therapeutic resistance to the RPT, and/or avoids cellular therapeutic resistance to the RPT. The tumor tissue/cells, cancer cells or pre-cancerous cells may be exposed to the sensitizer administered together with an RPT drug in its free form, or certain RPTs may be conjugated to a DZ residue and thus form part of the sensitizer as its DRG moiety or residue.

In an embodiment, provided is a sensitizer compound which is a DZ-DRG amide or ester conjugate, wherein a DZ-residue of formula FI or FII, via an amide or ester bond, is linked to the residue of a drug (DRG); wherein the conjugated drug (DRG) is selected from the group consisting of Cisplatin (CIS), Simvastatin (SIM), Artemisinin (ART), Gemcitabine (GEM), Doxorubicin (DOX), Paclitaxel (PAC), Docetaxel (DT), a platin-based compound, a statin, or a therapeutically functional derivative thereof, and wherein the DZ residue is selected from the group consisting of an amide DZ residue of formula I below

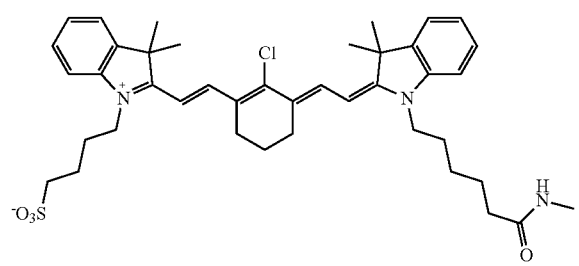

FI and an ester residue of formula II below

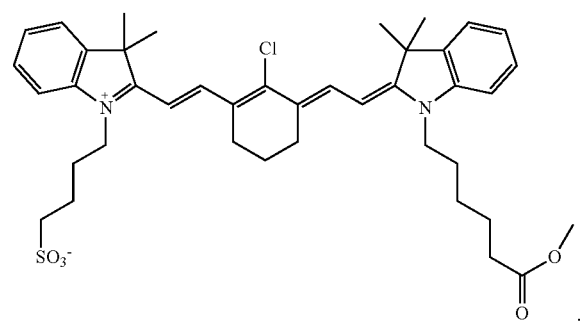

FII

In an embodiment, provided is a sensitizer compound, wherein the sensitizer is selected from group consisting of: DZ-CIS ester, DZ-CIS amide, DZ-SIM ester, DZ-SIM amide, DZ-ART ester, DZ-ART amide.

In an embodiment, provided is a sensitizer wherein the conjugated DRG is a statin drug selected from the group consisting of simvastatin, atorvastatin, fluvastatin, lovastatin, pitavastatin, pravastatin, and rosuvastatin.

In an embodiment, provided is a sensitizer wherein the conjugated DRG is a platin-based drug selected from the group consisting of cisplatin, carboplatin (also known as CBDCA), dicycloplatin (also known as DCP), oxaliplatin, satraplatin, picoplatin, nedaplatin, triplatin, lobapatin, heptaplatin, and lipoplatin.

In an embodiment, provided is a sensitizer wherein the conjugated DRG is a drug selected from the group consisting of Simvastatin (SIM), Cisplatin (CIS), and a therapeutically functional derivative thereof.

In an embodiment, provided is a pharmaceutical composition comprising a sensitizer compound which is a DZ-DRG amide or ester conjugate and at least one pharmaceutically acceptable carrier; wherein a DZ-residue of formula FI or FII, via an amide or ester bond, is linked to the residue of a DRG drug; wherein the conjugated DRG of the sensitizer is selected from the group consisting of Cisplatin (CIS), Simvastatin (SIM), Artemisinin (ART), a platin-based compound, a statin, or a therapeutically functional derivative thereof, and wherein the DZ residue is selected from the group consisting of an amide DZ residue of formula I below

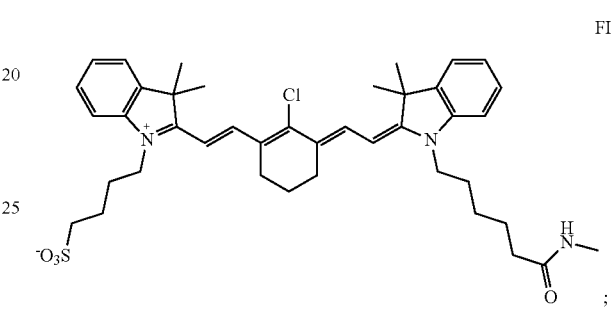

FI and an ester DZ reside of formula II below

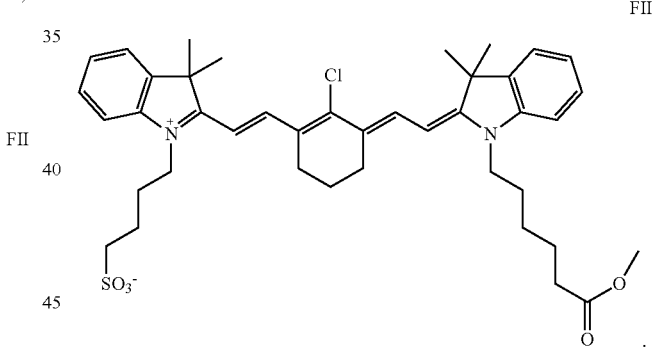

FII

In an embodiment, provided is a pharmaceutical composition wherein the sensitizer is selected from the group consisting of DZ-CIS ester, DZ-CIS amide, DZ-SIM ester, DZ-SIM amide, DZ-ART ester, and DZ-ART amide.

In an embodiment, provided is a pharmaceutical composition wherein the concentration of the sensitizer compound and its carrier are adapted to provide the sensitizer to pre-cancerous cells or cancer cells of a tumor type generally responsive, and optionally resistant, to a RPT selected from the group consisting of Cisplatin (CIS), Gemcitabine (GEM), Doxorubicin (DOX), Paclitaxel (PAC), Docetaxel (DT), a platin-based compound, or a therapeutically functional derivative thereof, in sufficient concentration to sensitize the tumor or cancer cells to the RPT.

In an embodiment, provided is a pharmaceutical composition as part of a kit of one or more pharmaceutical compositions, the kit comprising (1) the DRG-conjugated sensitizer (2) a RPT (3) one or more delivery means for (1), (2), or for both, and (4) instructions for coordinated administration of the sensitizer and the RPT in a common administration regimen, wherein the RPT is selected from the group consisting of Cisplatin (CIS), Gemcitabine (GEM), Doxorubicin (DOX), Paclitaxel (PAC), Docetaxel (DT), a platin-based compound, or a therapeutically functional derivative thereof.

In an embodiment, provided is a composition wherein (1) is DRG-CIS, and (2) RPT is selected from the group consisting of CIS, a platin-based compound, or a therapeutically functional derivative thereof.

In an embodiment, provided is a composition wherein for (1) the DRG sensitizer is selected from the group consisting of DRG-SIM and DRG-ART.

In an embodiment, provided is a composition wherein for (1) the DRG sensitizer is selected from the group consisting of DRG-SIM and DRG-ART, and for (2) the RPT is CIS.

In an embodiment, provided is a method of sensitizing tumor, cancer, or precancerous cells present in a subject to the treatment with a RPT drug;

In an embodiment, provided is a method wherein the sensitizer is a DZ-DRG amide or ester conjugate comprising a conjugated DRG; wherein the DRG is selected from the group consisting of Cisplatin (CIS), Simvastatin (SIM), Artemisinin (ART), a platin-based compound, a statin, or a therapeutically functional derivative thereof; wherein the RPT is selected from the group consisting of Cisplatin (CIS), Gemcitabine (GEM), Doxorubicin (DOX), Paclitaxel (PAC), Docetaxel (DT), a platin-based compound, or a therapeutically functional derivative thereof; and wherein the DZ residue is selected from the group consisting of a DZ amide of formula FI, and a DZ ester of formula FII, shown below:

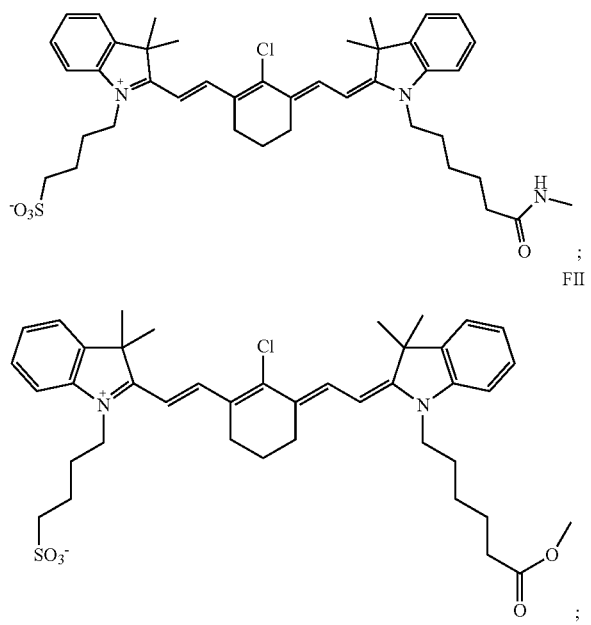

the method comprising exposing a plurality of tumor, cancer or pre-cancerous cells to the RPT by administering a sensitizer compound to a subject in need of treatment with the RPT, in an amount and concentration sufficient to increase the sensitivity of the cells to the RPT.

In an embodiment, provided is a method, comprising co-administering, or administering in a coordinated schedule adapted to increase the sensitivity of the cells to the RPT, and in an amount and concentration sufficient for the RPT to provide an anticancer effect in presence of, or together with, the sensitizer.

In an embodiment, provided is a method, wherein the RPT is selected from the group consisting of CIS, and a platin-based compound (PT), and the tumor, cancer or pre-cancerous cells are exposed and thus sensitized to CIS by its administration in form the DZ-CIS conjugate or the DZ-PT conjugate.

In an embodiment, provided is a method, wherein the RPT is selected from the group consisting of CIS, and a platin-based compound (PT), and wherein the sensitizer is selected from the group consisting of DZ-SIM ester, DZ-SIM amide, DZ-ART ester, a DZ-ART amide.

In an embodiment, provided is a method, wherein the DRG of the sensitizer is a statin selected from the group consisting of atorvastatin, fluvastatin, lovastatin, pitavastatin, pravastatin, and rosuvastatin.

In an embodiment, provided is a method, wherein the DRG of the sensitizer is a platin-based compound selected from the group consisting of cisplatin, carboplatin (also known as CBDCA), and dicycloplatin (also known as DCP), oxaliplatin, satraplatin, picoplatin, nedaplatin, triplatin, lobapatin, heptaplatin, and lipoplatin.

In an embodiment, provided is a method, wherein the tumor, cancer, or precancerous cells are cells of one or more of lung cancer, non-small cell lung cancer (NSCLC), small cell lung cancer (SCLC), pancreatic cancer, kidney cancer, and prostate cancer.

In an embodiment, provided is method wherein prior to administration of one or more of sensitizer or RPT, the method comprises the further steps of: isolating cancer cells from a patient; culturing the isolated cancer cells in a suitable medium that allows cell growth; exposing the cancer cells to one or more of DZ-RPT sensitizer and RPT, and determining sensitivity of the cells to one or more of sensitizer and RPT.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

FIG. 1A-B (A) shows the calculated 50% inhibitory concentration (IC50) of DZ-CIS ester compared to Cisplatin as tested in cell line A549. FIG. 1A-B (B) shows the calculated 50% inhibitory concentration (IC50) of DZ-CIS ester compared to Cisplatin as tested in cell line A549/DDP. FIG. 1A-B (C) shows the calculated 50% inhibitory concentration (IC50) of DZ-CIS ester compared to Cisplatin as tested in cell line 95C. FIG. 1A-B (D) shows the calculated 50% inhibitory concentration (IC50) of DZ-CIS ester compared to Cisplatin as tested in cell line 95D.

FIG. 1E-F (E) shows the calculated 50% inhibitory concentration (IC50) of DZ-CIS ester compared to Cisplatin as tested in cell line H446. FIG. 1E-F (F) shows the calculated 50% inhibitory concentration (IC50) of DZ-CIS ester compared to Cisplatin as tested in cell line YTMLC-9.

FIG. 2 (B) shows the calculated 50% inhibitory concentration (IC50) of Cisplatin, with various concentrations of DZ-SIM Amide, as tested in cell line A549. FIG. 2 (C) shows the calculated 50% inhibitory concentration (IC50) of Cisplatin, with various concentrations of DZ-SIM Ester, as tested in cell line A549/DDP. FIG. 2 (D) shows the calculated 50% inhibitory concentration (IC50) of Cisplatin, with various concentrations of DZ-SIM Amide, as tested in cell line A549/DDP.

FIG. 3B1 shows the calculated 50% inhibitory concentration (IC50) of conventional chemotherapeutic drug Gemcitabine alone and in combination with SIM or DZ-SIM Ester, as tested in mouse pancreatic cancer cell line NKPC-961. FIG. 3B2 shows the calculated 50% inhibitory concentration (IC50) of SIM and DZ-SIM Ester, as tested in mouse pancreatic cancer cell line NKPC-961. FIG. 3B3 shows the calculated 50% inhibitory concentration (IC50) of Cisplatin alone and in combination with SIM or DZ-SIM Ester, as tested in mouse pancreatic cancer cell line NKPC-961. FIG. 3B4 shows the calculated 50% inhibitory concentration (IC50) of Cisplatin alone and in combination with various concentrations of DZ-SIM Ester, as tested in mouse pancreatic cancer cell line NKPC-961.

FIG. 4 shows DZ-SIM, but not SIM, inhibits the growth of therapeutically resistant tumors in vivo, and sensitizes prostate carcinoma tumors to the anticancer effects of cytotoxic prostate cancer chemotherapeutic drug, Docetaxel (DT).

FIG. 5-1 shows the effect of Cisplatin and DZ-CIS Ester on the in vivo growth of tumors in a human lymphoma xenograft model, as tested in NCr Nu/Nu mice. FIG. 5-2 shows the effect of Cisplatin and DZ-CIS Ester on the in vivo growth of tumors in a human lymphoma xenograft model, as tested in NOD-SCID mice.

FIG. 6-1 shows the calculated 50% inhibitory concentration (IC50) of Cisplatin compared to DZ-CIS Ester as tested in human ovarian cancer cell strain OV90. FIG. 6-2 shows the calculated 50% inhibitory concentration (IC50) of Cisplatin compared to DZ-CIS Ester as tested in human ovarian cancer cell strain OVCA 433.

FIG. 7 (Left-Side) shows the CaspaseGlo 3/7 luminescent assay of Cisplatin and DZ-CIS Ester, as tested in human Burkitt lymphoma cell line Namalwa.

FIG. 10 (Left-Side) shows a histopathology of a mouse kidney treated with DZ-CIS Ester.

FIG. 16-1 shows the growth inhibitory effect of Simvastatin compared to DZ-SIM Ester as tested in ovarian tumor cells OV90 and OVCA433. FIG. 16-2 shows the growth inhibitory effect of Cisplatin compared to DZ-CIS Ester as tested in ovarian tumor cells OV90 and OVCA433.

DETAILED DESCRIPTION OF THE INVENTION

Figure 2:
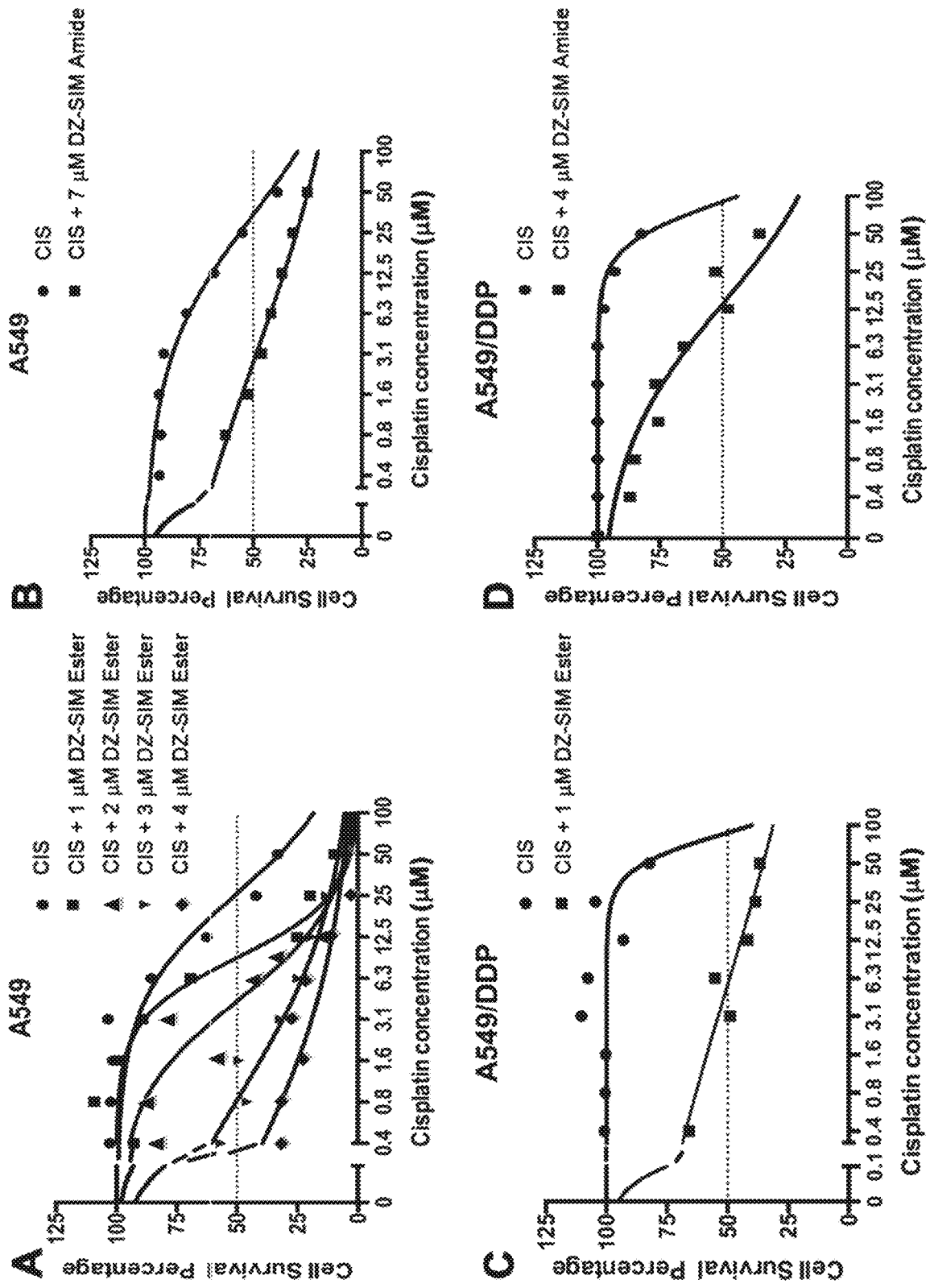
FIG. 2 (A) shows the calculated 50% inhibitory concentration (IC50) of Cisplatin, with various concentrations of DZ-SIM Ester, as tested in cell line A549.

The present invention generally relates to sensitizer compounds and their use to sensitize tumor, cancer and/or pre-cancerous cells to treatment with certain resistance-prone therapeutics (RPTs) used for their anticancer effects on such cells in the therapy of tumors or cancer. The sensitizers are dye-drug conjugates of a particular NIR dye amide or ester derivative, generally referred to herein as sensitizers, sensitizer compounds, DZ-DRG, and DZ-DRG amide or ester, respectively. The dye residue may be referred to herein, in particular in the figures, as "DZ", "DZ1", "D", "dye", or "HMCD", and its amide/ester, respectively. Where ester or amide is not indicated, both derivatives are encompassed. The related conjugates with drugs (DRG) may be referred to accordingly, e.g. DZ-DRG, DZ-Cisplatin, DZ-CIS, DZ-Simvastatin, DZ-SIM (or DZ1-SIM, dye-Simvastatin, or DS), similar applies to the other conjugated DRG (e.g. DZ-Artemisinin or DZ-ART. DZ-Platin or DZ-PT, DZ-statin, and so forth.

In embodiments, the anticancer effects of RPTs against tumor cells/tissues, cancer cells, or pre-cancer cells may include reducing the number of these cells, slowing cell or tumor growth, reducing or slowing the increase of tumor volume, inducing apoptosis (programmed cell death), reducing formation of metastases, reducing the spreading of cancer cells or metastases through the body, and reducing the formation of further tumors. Therapeutic resistance to RPTs may occur over the duration of therapy, e.g. anticancer effects initially achieved will cease and e.g. tumors will not reduce their volume, or not to the same extent, tumor, cancer and pre-cancer cells will not be inhibited in their growth or development, and their apoptosis will not occur, or not occur to the same extend, etc. Further, certain subtypes of tumors, cancer cells or pre-cancerous cells exposed to the RPT may display resistance to RPT therapy from the start, despite belonging to a generally responsive type of tumor or tissue.

In embodiments, these RPTs may include Cisplatin (CIS), Gemcitabine (GEM), Doxorubicin (DOX), Paclitaxel (PAC), Docetaxel (DT), a platin-based compound (PT), or therapeutically functional derivatives thereof. Such RPTs have been associated with resistance of tumor, cancer or pre-cancerous cells to treatment using these RPTs. While these RPTs often have initial anticancer effects, these effects decline over time of use, or with repeated use on cells.

In embodiments, the conjugates of particular esters or amides of Near Infrared Dyes (NIR Dyes), referred to herein as DZ-amide or ester conjugates, may be used as sensitizers to reduce the risk of resistance to RPTs, increase therapeutic response to the RPT, and to overcome drug resistance once formed. In embodiments, these DZ-DRG conjugates include sensitizers wherein the conjugated DRG is selected from Cisplatin (CIS), Simvastatin (SIM), Artemisinin (ART), a platin-based compound (PT), and a statin, for sensitizing cells to the therapeutic effects of one or more RPT.

In an embodiment, a sensitizer may be co-administered or used in combination with one or more RPT; for example CIS, GEM, DOX, PAC or DT, or derivatives thereof may be co-administered with a DZ-DRG sensitizer. In this case, the RPT is unconjugated to the sensitizer.

In an embodiment, in case of CIS or another platin-based compound (PT), the DRG moiety of the sensitizer itself may be a conjugated RPT, i.e. a RPT-derived moiety or residue linked to the DZ ester or amide to form the sensitizer, e.g. conjugated CIS or PT, in particular a DZ-CIS amide, DZ-CIS ester, DZ-PT amide, and DZ-PT ester. In this case, administration of the sensitizer at the same time provides the RPT (in conjugated form, as the DRG).

Embodiments of the invention can advantageously be used to achieve an anticancer effect on tumors, cancer cells or pre-cancerous cells that have a tendency to develop resistance to cancer therapeutics such as the RPTs described herein, and/or to form metastases; these include cells of lung, pancreatic, prostate, testicular, ovarian, cervical, bladder, breast, head and neck, esophageal, and stomach cancers/tumors, germ cell tumors, lymphomas and other cancers.

In an embodiment, DZ-CIS, DZ-PT, or combinations of DZ-DRG combined with CIS/PT as RPT may be used to sensitize RPT-therapy resistant tumor, cancer and pre-cancerous cells, including in particular lung cancer, non-small cell lung cancer, sarcomas, some carcinomas (including, e.g., small cell lung cancer (SCLC), squamous cell carcinoma of the head and neck, ovarian cancer), lymphomas, bladder cancer, cervical cancer, germ cell tumors, and testicular cancer. Carboplatin typically is used to treat ovarian cancer, lung cancer, head and neck cancer, brain cancer, and neuroblastoma and Carboplatin sensitizers or DZ-DRG combinations with Carboplatin may be used for these cancers as well. The risk of resistance to CIS or PT may thus be reduced or resistance may be overcome.

In an embodiment, DZ-SIM may be used for the treatment of one or more of lung cancer, small cell lung cancer (SCLC), and non-small cell lung cancer (NSCLC), and other cancers as disclosed herein.

Without wishing to be bound by theory, both the particular therapeutic cancer drug, its amount and/or concentration applied, and the type and stage of cancer are believed to contribute to the potential for the development of therapeutic resistance to the RPT drugs. Embodiments of the invention can advantageously be used in cancers that have a tendency to develop resistance to certain RPTs and/or form metastases, especially in their more aggressive/metastatic forms, in a therapeutically resistant sub-type, or after initial treatment with RPTs that are subject to the development of resistance in certain cancers, e.g. one or more of CIS, GEM, DOX, PAC, DT or PT in one or more cancer selected from the group comprising: lung, pancreatic, prostate, testicular, ovarian, cervical, bladder, breast, head and neck, esophageal, and stomach, cancers, germ cell tumors, lymphomas, and other cancers.

In an embodiment, in addition to a sensitizing effect, advantageously, the sensitizers of the present invention may, together with one or more RPT, advantageously provide anti-cancer or anti-tumor effects, including to inhibit growth of cancer cells, and/or to initiate the apoptosis of cancer cells. Advantageously, in a variety of different cancer types and tumors, sensitizers may contribute to the effect of the RPTs in a more-than-additive and/or synergistic fashion.

In an embodiment, in addition to a sensitizing effect, the sensitizers of the present invention may advantageously protect normal tissues from damage caused by the RPT, including liver, kidney, lung, pancreas, prostate, testicular, ovarian, cervical, bladder, breast, head and neck, esophageal, and stomach tissues, germ cells, blood cells and other tissues of the body.

In an embodiment, in addition to a sensitizing effect, the sensitizers of the present invention may advantageously protect normal liver tissues from damage caused by the RPT. In particular, the sensitizers may protect from liver damage by a RPT including CIS, for example tissue necrosis.

In an embodiment, in addition to a sensitizing effect, the sensitizers of the present invention may advantageously protect protect normal kidney tissue from damage caused by the RPT. In particular, the sensitizers may protect from kidney damage by a RPT including CIS, for example damage such as e.g. tubular diallation, excessive intratubular debris and tubular necrosis.

In an embodiment, in addition to a sensitizing effect, the sensitizers of the present invention may advantageously have one or more of the following additional effects: inhibiting tumor progression, inhibiting the formation of metastases, toxic effect on mitochondria, and toxic effect on lysosomes.

In an embodiment, the sensitizer of the invention may be conjugated to Simvastatin (DZ-SIM). Similar results may be achieved replacing the simvastatin moiety in the compound with a moiety derived from compound of the same class of drugs, namely another statin. Non-limiting examples of statins, in addition to simvastatin, include: atorvastatin, fluvastatin, lovastatin, pitavastatin, pravastatin, rosuvastatin), and derivatives thereof.

In an embodiment, the sensitizer of the invention may be conjugated to cisplatin (CIS), also known as cis-diamminedichloridoplatinum (II) or CDDP. Similar to CIS, many of its derivatives or other platin-based compounds also suffer from associated therapeutic resistance when used for their anticancer effect on the cells of a patient, and the sensitizers may similarly be conjugated to such CIS derivatives or platin-based compounds and be used to sensitize tumor, cancer or pre-cancerous cells to such platin-based compounds. Non-limiting examples of such platin-based compounds with anti-cancer effects on cells may include: oxoplatin, carboplatin (also known as CBDCA), dicycloplatin (also known as DCP), oxaliplatin, satraplatin, picoplatin, nedaplatin, triplatin, lobapatin, heptaplatin, lipoplatin, and derivatives thereof.

In an embodiment, the DZ-conjugated amide/ester sensitizer may be conjugated to artemisinin (ART). Similar results may be achieved replacing artemisinin with a compound of the same class and/or an artemisinin derivative having anticancer effects on cells. Non-limiting examples of artemisinin derivatives include: dihydroartemisinin, and derivatives thereof.

In an embodiment, the DZ-conjugated sensitizers may include DZ-CIS ester, DZ-CIS amide, DZ-SIM ester, and DZ-SIM amide, DZ-ART ester, and DZ-ART amide, and their use for sensitizing tumor, cancer or pre-cancerous cells to treatment with RPTs by exposing such cells to the sensitizer and the RPT, e.g. by administering a sensitizers and a RPT to a subject having such cells, including cancer and tumor patients. Particular examples of these sensitizers and their chemical formulae are shown below. The sensitizers include

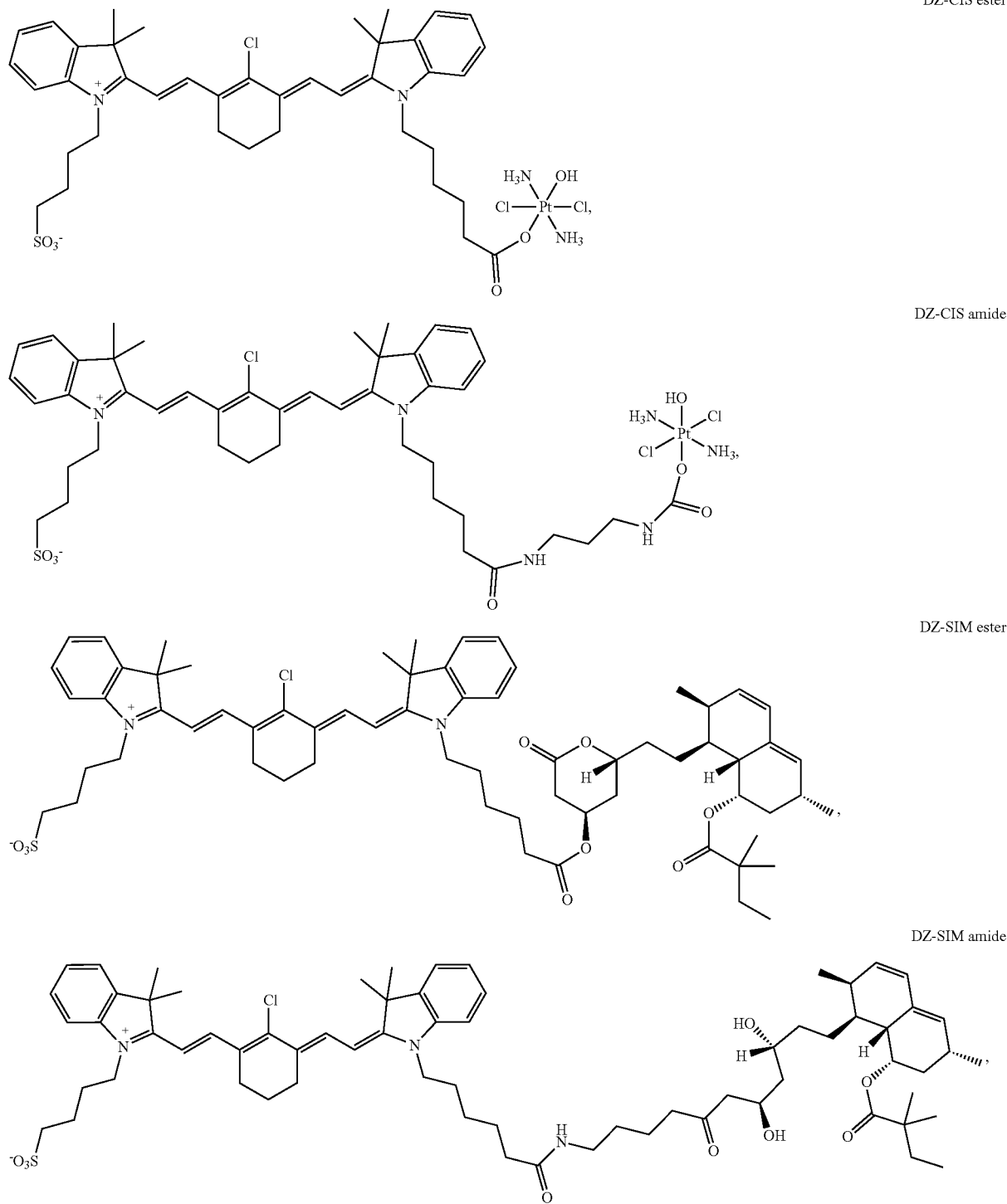

DZ-CIS ester

DZ-CIS amide

DZ-SIM ester

DZ-SIM amide

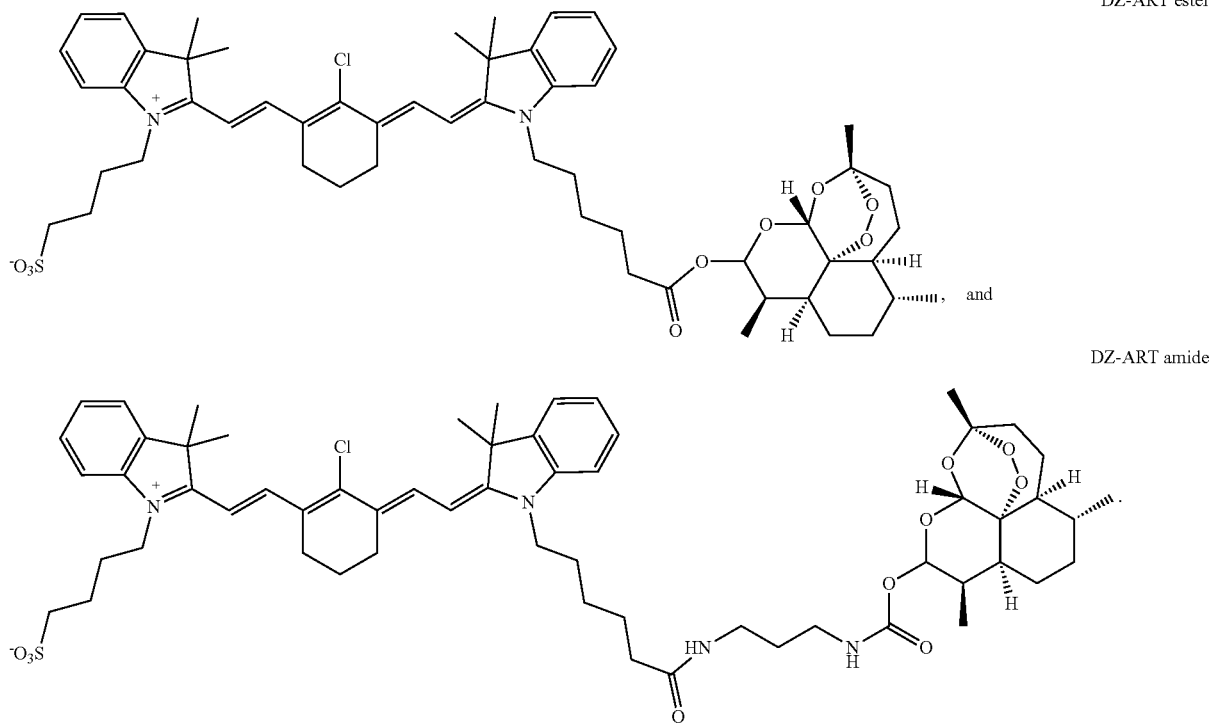

DZ-ART ester and

DZ-ART amide

According to an embodiment of the present invention, for treatment of solid malignancies, the sensitizers and in particular DZ-CIS may be administered, for example, intravenously as a short-term infusion in normal saline.

In an embodiment, to sensitize tumor, cancer or pre-cancerous cells to a RPT, the sensitizer may be administered to a subject prior to or concurrently with DZ-DRG administration. Alternatively, for treatment of cancer cells that already developed resistance to the RPT, the sensitizer may be administered to the patient after one or more initial RPT administration, optionally before or concurrently with one or more further RPT administration.

According to an embodiment of the present invention, a pharmaceutical composition comprising one or more sensitizer compound is provided. The pharmaceutical composition may be for human or for veterinary use, and comprise one or more compound of the invention (or a salt, solvate, metabolite, or derivative thereof) with one or more pharmaceutically acceptable carrier and/or one or more excipient and/or one or more active. The one or more carrier, excipient and/or active may be selected for compatibility with the other ingredients of the formulation and not unduly deleterious to the recipient thereof. Such carriers are known in the art and may be selected as will be apparent to a person of ordinary skill in the art.

According to an embodiment of the present invention, routes of administration for the compounds and pharmaceutical compositions include, but are not limited to: oral, intraperitoneal, subcutaneous, intramuscular, transdermal, rectal, vaginal, sublingual, intravenous, buccal, or inhalational. In some embodiments, the pharmaceutical compositions of the invention contain a pharmaceutically acceptable excipient suitable for rendering the compound or mixture administrable via the above routes of administration. Alternatively, the pharmaceutical compositions may be be administered through urogenital routes, e.g. via internal organs, topical lesions, or access by instillation (such as urinary bladder, vaginal cannel).

According to an embodiment of the present invention, the active ingredients can be admixed or compounded with a conventional, pharmaceutically acceptable excipient. A mode of administration, vehicle, excipient or carrier should generally be substantially inert with respect to the active agent, as will be understood by those of ordinary skill in the art. Illustrative of such methods, vehicles, excipients, and carriers are those described, for example, in Remington's Pharmaceutical Sciences, 18th ed. (1990), the disclosure of which is incorporated herein by reference. The excipient must be "acceptable" in the sense of being compatible with the other ingredients of the formulation and not deleterious to the recipient thereof.

According to an embodiment of the present invention, the pharmaceutical formulations may be conveniently made available in a unit dosage form by any of the methods generally known in the pharmaceutical arts. Generally speaking, such methods of preparation comprise presenting the formulation in a suitable form for delivery, e.g., forming an aqueous suspension. The dosage form may optionally comprise one or more adjuvant or accessory pharmaceutical ingredient for use in the formulation, such as mixtures, buffers, and solubility enhancers.

According to an embodiment of the present invention, parenteral dosage forms (i.e. that bypass the GI tract) of the pharmaceutical formulations include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

According to an embodiment of the present invention, suitable vehicles that can be used to provide parenteral dosage forms of the compounds of the invention include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound of the invention as disclosed herein can also be incorporated into the parenteral dosage forms of the disclosure, including conventional and controlled-release parenteral dosage forms.

According to an embodiment of the present invention, formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents.

According to an embodiment of the present invention, injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

According to an embodiment of the present invention, compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

According to an embodiment of the present invention, forms suitable for oral or sublingual administration include tablets, troches, capsules, elixirs, suspensions, syrups, wafers, chewing gum, or the like prepared by art recognized procedures. The amount of active compound in such therapeutically useful compositions or preparations is such that a suitable dosage will be obtained. A syrup formulation will generally consist of a suspension or solution of the compound or salt in a liquid carrier, for example, ethanol, glycerine or water, with a flavoring or coloring agent.

According to an embodiment of the present invention, solid dosage forms for oral administration include capsules, tablets, pills, powders, and granules. In such solid dosage forms, the active compound is mixed with at least one inert, and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

According to an embodiment of the present invention, solid compositions of a similar type can also be employed as fillers in soft and hardfilled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

According to an embodiment of the present invention, the active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

According to an embodiment of the present invention, the active compounds be present in form of salts, which may be particularly suitable for use in the treatment of cancer. The salts of the present invention may be administered to the patient in a variety of forms, depending on the route of administration, the salt involved, and the cancer being treated. For example, an aqueous composition or suspension of the salts may be administered by injection, or in the form of a pharmaceutical matrix by injection or surgical implantation, at a desired site. The particular technique employed for administering the matrix may depend, for example, on the shape and dimensions of the involved matrix. In some embodiments, the salt is introduced substantially homogeneously in a tumor to minimize the occurrence in the tumor of cold (untreated) areas. In certain embodiments, the salt is administered in combination with a pharmaceutically acceptable carrier. A wide variety of pharmaceutically acceptable carriers are available and can be combined with the present salts, as will be apparent to one of ordinary skill in the art.

According to an embodiment of the present invention, effective amounts, toxicity, and therapeutic efficacy of the active compounds can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods exhibit large therapeutic indices. A therapeutically effective dose can be estimated initially from cell culture assays. Also, a dose can be formulated in animal models to achieve a circulating plasma concentration range that includes the IC50 (i.e., the concentration of the compound of the invention, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

According to an embodiment of the present invention, the dosage of a pharmaceutical formulation as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule/regimen can vary, e.g. once a week, daily, or in particular predetermined intervals, depending on a number of clinical factors, such as the subject's sensitivity to each of the active compounds.

According to an embodiment, a composition comprising one or more sensitizer can be administered to tumor, cancer or pre-cancerous cells of a subject, in an effective dose to sensitize the cells to a RPT and thus provide an anticancer effect in combination with the RPT. The RPT may be concurrently administered to a subject or patient (e.g. in unconjugated form or as DZ-RPT conjugate, i.e. DZ-CIS or DZ-PT), or the RPT may be administered shortly before or shortly after the sensitizer, e.g. according to a particular dosing regimen that takes into account e.g. the concentration of the sensitizer and the RPT in the blood, and the half-life of these actives, as will be apparent to a person of ordinary skill.

According to an embodiment of the present invention, an effective dose of a composition comprising a sensitizer compound can be administered to a patient once. Alternatively, an effective dose of a composition comprising a compound of the invention can be administered to a patient repeatedly. In certain embodiments, an effective dose of a composition comprising a compound of the invention can be administered to a patient via skin patches, instillation into urinary bladder through urethral, or vaginal channel through ring implantation. Patients can be administered a therapeutic amount of a composition comprising a compound of the invention. A composition comprising a compound of the invention can be administered over a period of time, such as over a 5 minute, 10 minute, 15 minute, 20 minute, or 25 minute period. If warranted, the administration can be repeated, for example, on a regular basis, such as hourly for 3 hours, 6 hours, 12 hours or longer or such as biweekly (i.e., every two weeks) for one month, two months, three months, four months or longer. In some instances, after an initial treatment regimen, the treatments can be administered on a less frequent basis. For example, after administration biweekly for three months, administration can be repeated once per month, for six months or a year or longer. Administration of a composition comprising one or more sensitizer together with a RPT in a coordinated administration schedule to ensure exposure to both, and preferably concurrent exposure to both (e.g. as DZ-conjugated RPT, including DZ-CIS and DZ-PT), can reduce levels of a biomarker or a symptom of cancer.

According to an embodiment of the present invention, the sensitizer compound may be administered to a subject up to several days, hours or minutes before administration of the RPT. For example, about 20-24 h before, about 15-20 hours before, about 12-15 hours before, about 10-12 hours before, about 8-10 hours before, about 2-8 hours before, about 1-6 hours before, about 1-4 hours before, about 1-3 hours before, about 1-2 hours before, about 0.5-1.5 hours before, or about 45-min. about 30 minutes, or about 15 minutes before RPT administration.

According to an embodiment of the invention, the concentration of the RPT may depend on the typical dosage of the particular RPT formulation, may be adapted to expose the tumor, cancer or pre-cancerous cells to concentrations of, e.g., from about 0.1 to about 100 uM. Generally, sensitizer concentrations of about 0.1 uM to about 25 uM, preferably 0.1 to about 10 uM may be adequate and provide a sufficient anti-cancer effect while protecting normal tissues such as kidney and liver from damage, e.g. from RPT-mediated damage, such as exhibited by CIS. If using sensitizers in combination with a RPT, for example, for CIS, the concentration may be from about 0.2 uM to about 10 uM, for example about 0.5 uM to about 5 uM or lower, e.g. from about 0.5 uM to about 4, 3, 2, or 1 uM, or lower, and may be combined with about 1 to 10 uM DZ-SIM amide or ester, or 1 to 10 uM DZ-CIS amide or ester.

According to an embodiment of the invention, the amount of the actives (sensitizer and optionally RPT) in the pharmaceutical composition can be based on weight, moles, or volume. In some embodiments, the pharmaceutical composition comprises at least 0.0001% compounds of the invention. In some embodiments, the pharmaceutical composition comprises at least 0.1% compounds of the invention. In some embodiments, the pharmaceutical composition comprises at least 0.5% compounds of the invention. In some embodiments, the pharmaceutical composition comprises at least 1% compounds of the invention. In some embodiments, the pharmaceutical composition comprises at least 2% compounds of the invention. In some embodiments, the pharmaceutical composition comprises at least 3% compounds of the invention. In some embodiments, the pharmaceutical composition comprises at least 4% compounds of the invention. In some embodiments, the pharmaceutical composition comprises at least 5% compounds of the invention. In some embodiments, the pharmaceutical composition comprises at least 10% compounds of the invention. In some embodiments, the pharmaceutical composition comprises 0.01%-99% of the compounds of the invention. In some embodiments, the pharmaceutical composition comprises 0.05%-90% of the compounds of the invention. In some embodiments, the pharmaceutical composition comprises 0.1%-85% of the compounds of the invention. In some embodiments, the pharmaceutical composition comprises 0.5%-80% of the compounds of the invention. In some embodiments, the pharmaceutical composition comprises 1%-75% of the compounds of the invention. In some embodiments, the pharmaceutical composition comprises 2%-70% of the compounds of the invention. In some embodiments, the pharmaceutical composition comprises 3%-65% of the compounds of the invention. In some embodiments, the pharmaceutical composition comprises 4%-60% of the compounds of the invention. In some embodiments, the pharmaceutical composition comprises 5%-50% of the compounds of the invention.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound of the invention.

Various embodiments provide for a bifunctional method of cell sensitization to RPTs, cancer therapy and imaging, wherein in addition to sensitization, pre-cancerous or cancerous cells and tumors in a patient in need thereof are identified, imaged and/or localized. The method can comprise providing one or more DZ (dye) comprising sensitizer compound; administering the one or more sensitizer compound to a patient who is further administered with one or more RPT (optionally in DZ-conjugated form); and performing optical imaging. This allows to visually follow and control stop of tumor growth and/or shrinkage, e.g. to confirm or personalize an optimized dosage, and/or determine the location of tumor(s) and/or metastase(s) within the NIR spectral region of DZ. In various embodiments, imaging may be performed, for example, about 6 to 48 hours post injection. Imaging may be performed in comparison to normal tissue/cells.

Various embodiments provide for a bifunctional method of conducting in situ pharmacokinetic and pharmacodynamic analyses of the sensitizer compounds of the present invention and its drug payload in a tumor or normal cell or tissue. The method can comprise providing the sensitizer; contacting it with the cancer cells, tumor, or normal cell or tissue; and imaging the cancer cells, tumor, or normal cell or tissue, followed by pharmacokinetic and/or pharmacodynamics analyses, e.g. determining the fluorescence (or changes thereof) over time.

DETAILED DESCRIPTION OF THE DRAWINGS

Figures 1, 5:
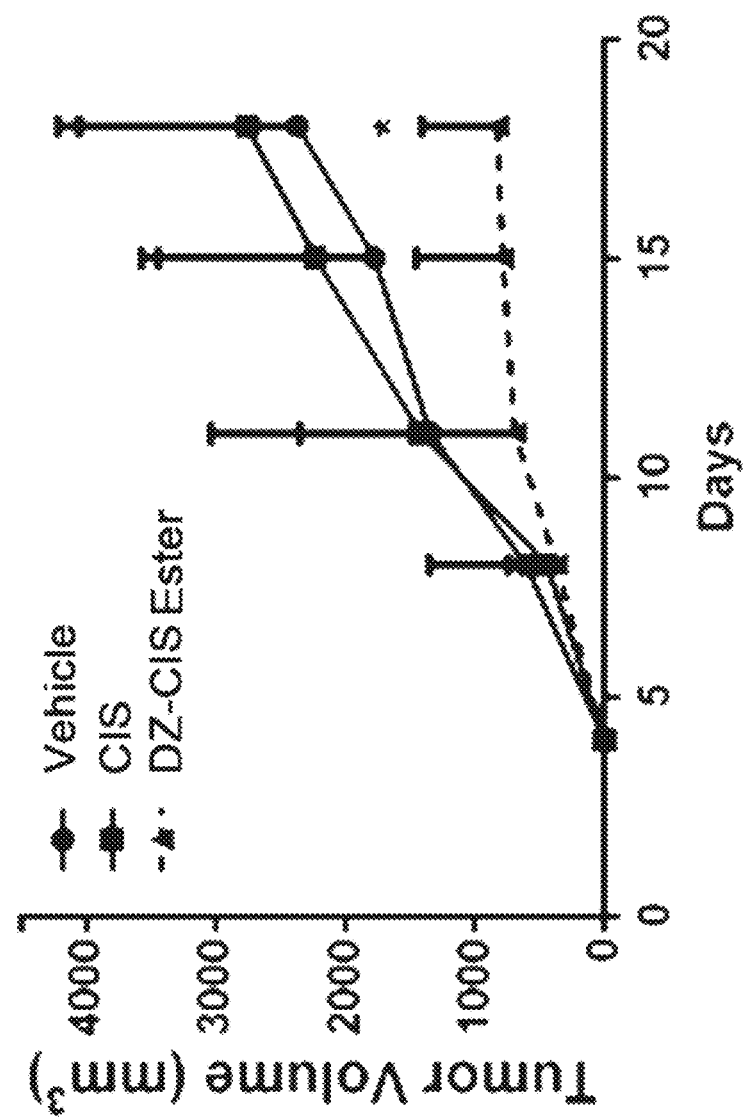
Figures 2, 5:
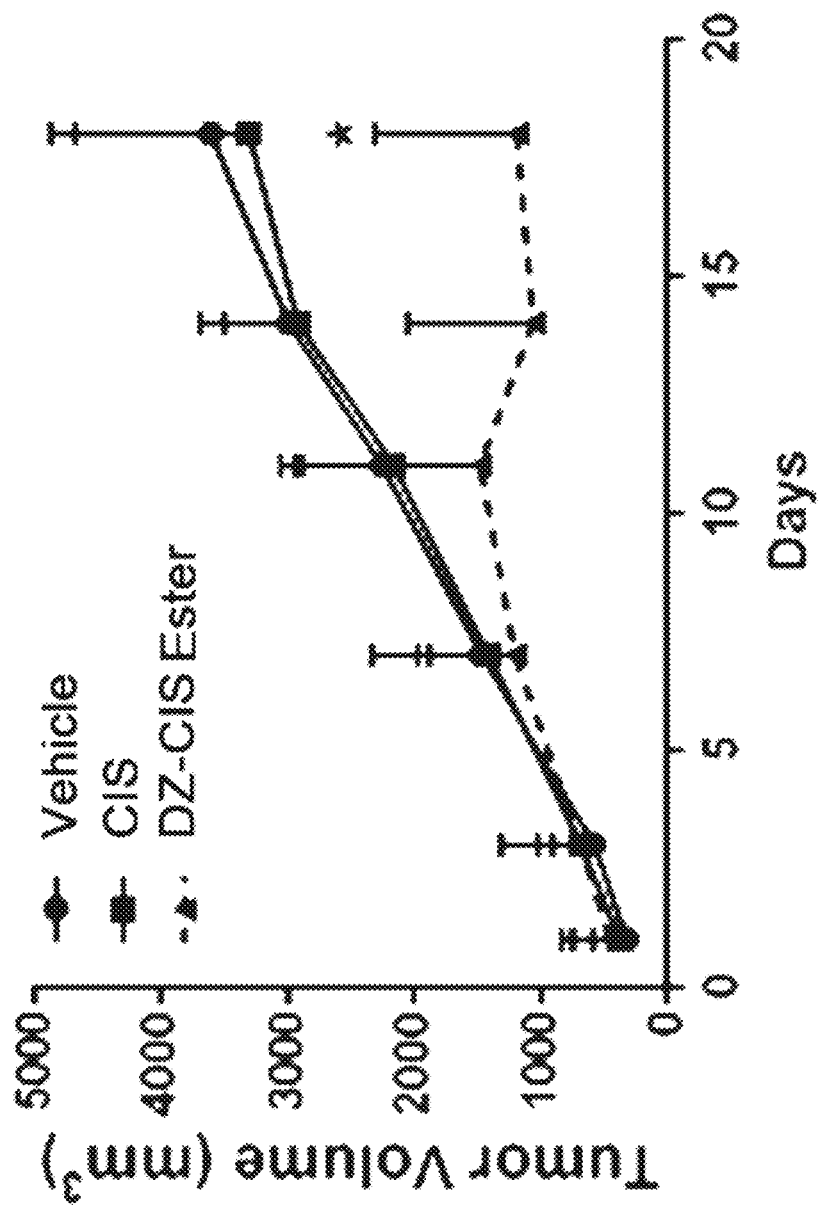

FIG. 1 shows a comparison of CIS versus DZ-CIS ester in human non-small cell lung cancer (NSCLC) and human small cell lung cancer (SCLC) cell lines in panels A-F. The calculated 50% inhibitory concentration (IC50) is shown on a logarithmic scale plotted over the respective drug concentrations. The graphs show that DZ-CIS is consistently more effective than CIS in a variety of different types of human lung cancer cells.

FIG. 2 shows a comparison of CIS alone versus a combination of CIS with DZ-SIM ester or amide in NSCLC cells (A 549 and and its isogenic CIS-resistant lung cancer cell line). The results in panels A-D show that DZ-SIM can sensitize NSCLC cells to the anticancer effects of CIS as measured by cell survival/IC50. In the presence of either DZ-SIM ester or amide, CIS IC50s are greatly reduced.

Figure 3A:
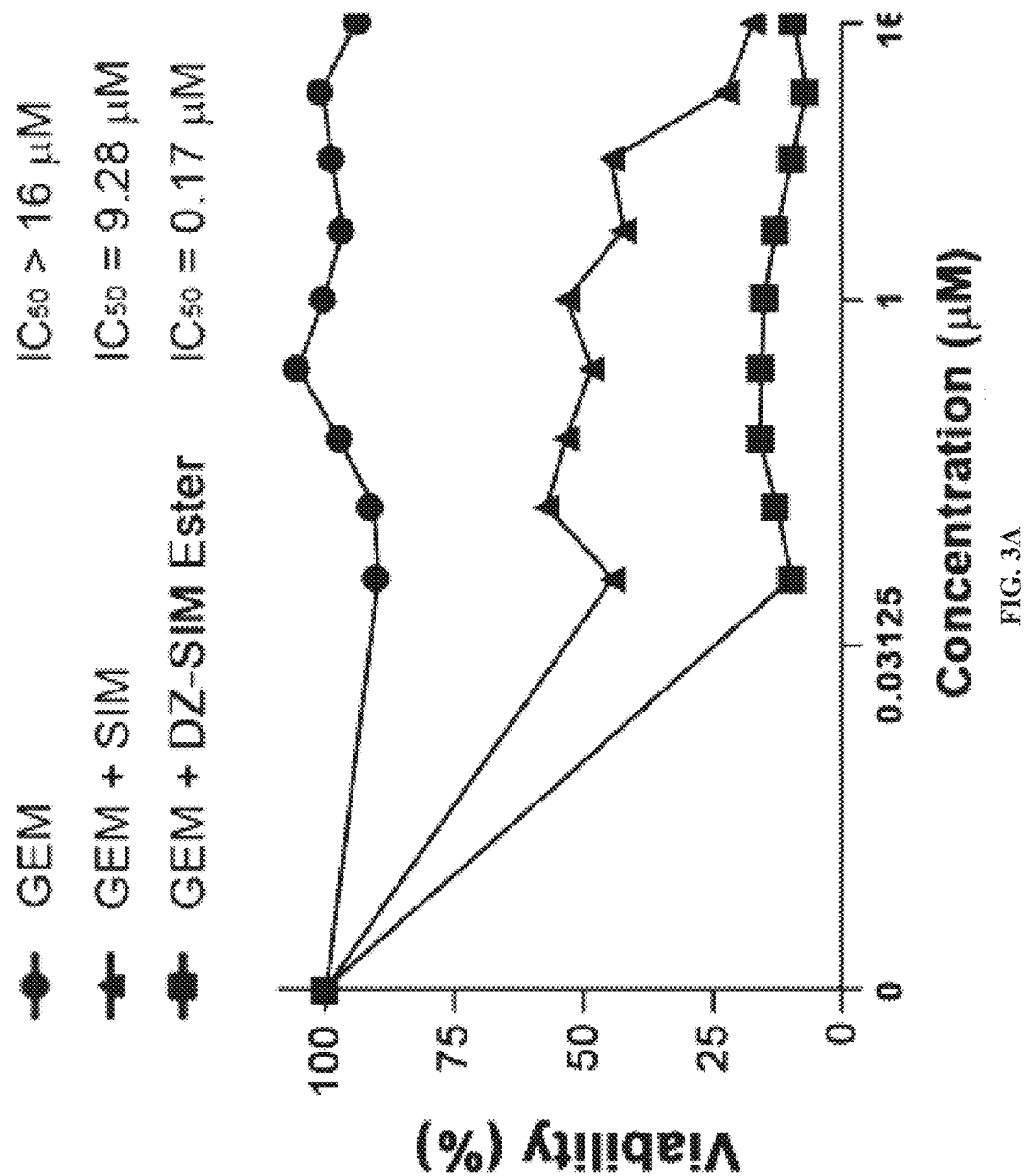
FIG. 3A shows the calculated 50% inhibitory concentration (IC50) of conventional chemotherapeutic drug Gemcitabine alone and in combination with SIM or DZ-SIM Ester, as tested in human pancreatic cancer cell line CTC-752-S-1.

FIG. 3A shows that DZ-SIM ester sensitizes human and mouse pancreatic cancer cells to the anticancer effects of Gemcitabine (GEM) or Paclitaxel (PAC, here "PTX") as measured by cell viability/IC50. In human pancreatic cancer cells CTC-752-S-1, DZ-SIM is more effective than SIM, while in mouse pancreatic cancer cell line MiaPaCa II both achieve similar sensitization.

Figure 3B:
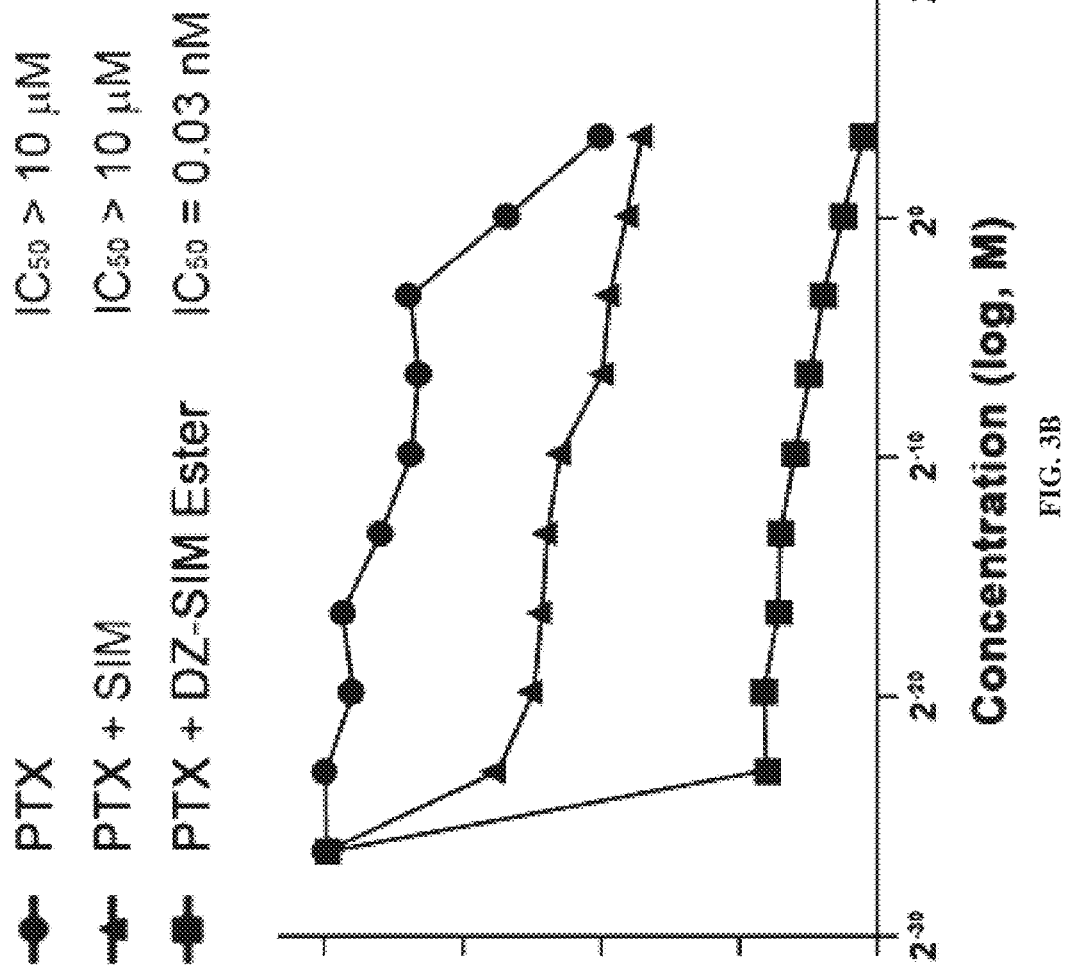
FIG. 3B shows the calculated 50% inhibitory concentration (IC50) of conventional chemotherapeutic drug Paclitaxel alone and in combination with SIM or DZ-SIM Ester, as tested in human pancreatic cancer cell line CTC-752-S-1.

FIG. 3B shows that DZ-SIM and SIM sensitize mouse pancreatic cancer cell line NKPC-961 to Cisplatin (CIS) and Gemcitabine (GEM), with both DZ-SIM and SIM enhancing anticancer effects of GEM and of CIS as measured by cell viability/IC50.

Figure 4:
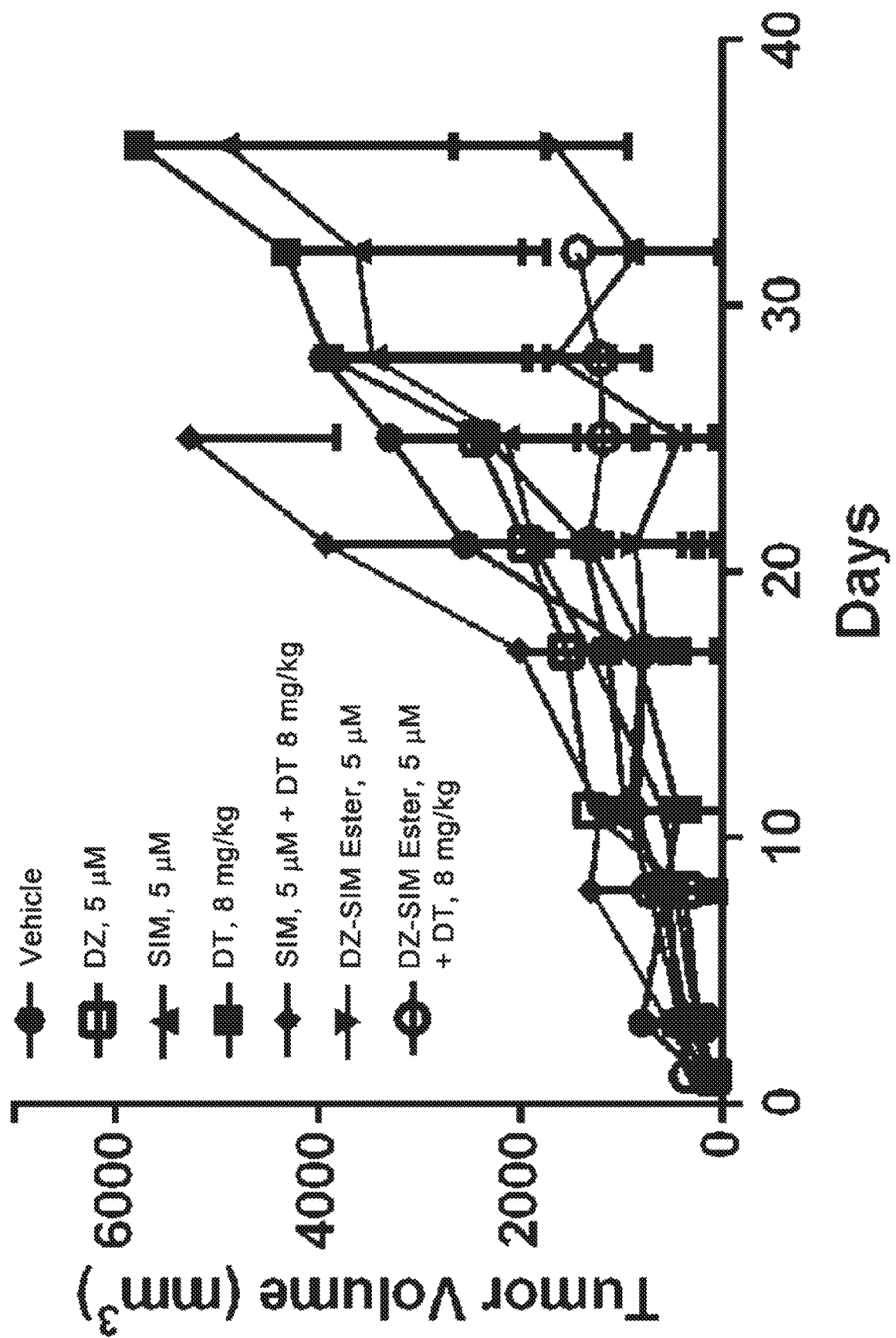

FIG. 4 shows that DZ-SIM inhibits the growth of therapeutically resistant tumors in vivo. DZ-SIM ester sensitizes prostate carcinoma tumors to the anticancer effects of a cytotoxic prostate cancer chemotherapeutic drug, Docetaxel (DT). Only DZ-SIM, but not SIM, inhibited the growth of tumors in vivo. DT alone is ineffective in inhibiting 22Rv1 tumor growth in vivo, and SIM alone or in combination with DT also is ineffective, while DZ-SIM is shown to sensitize the therapeutically resistant 22Rv1 tumors to DT.

FIG. 5 shows that DZ-CIS inhibits in vivo growth of tumors, including in a human lymphoma xenograft model, human Burkitt lymphoma cell line (Namalwa)-derived tumors in mice. In comparison to a control (vehicle) and CIS, results for DZ-CIS show a significant difference in tumor volume in cells treated with DZ-CIS ester compared to CIS or vehicle/control.

Figures 1, 6:
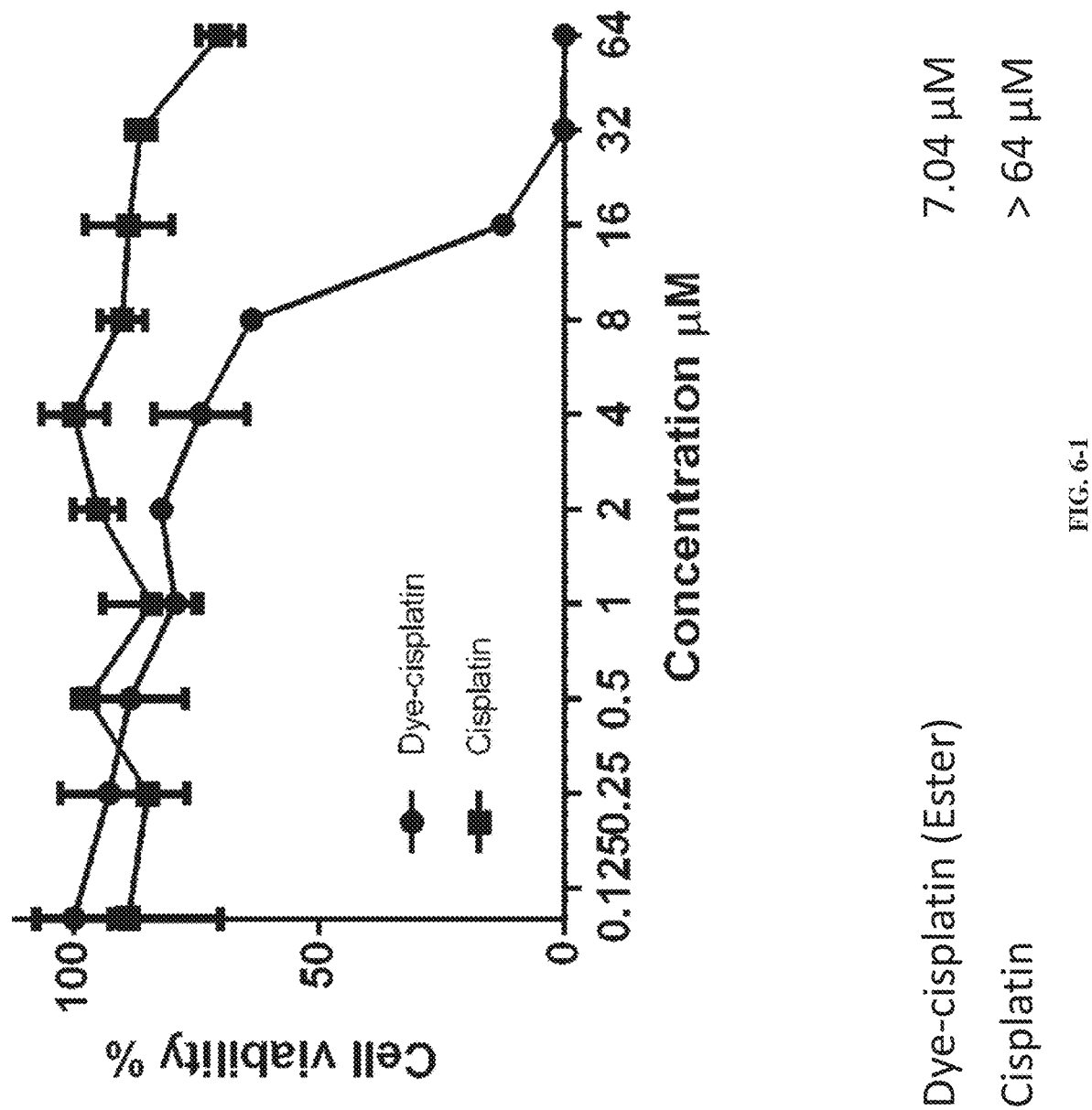
Figures 2, 6:
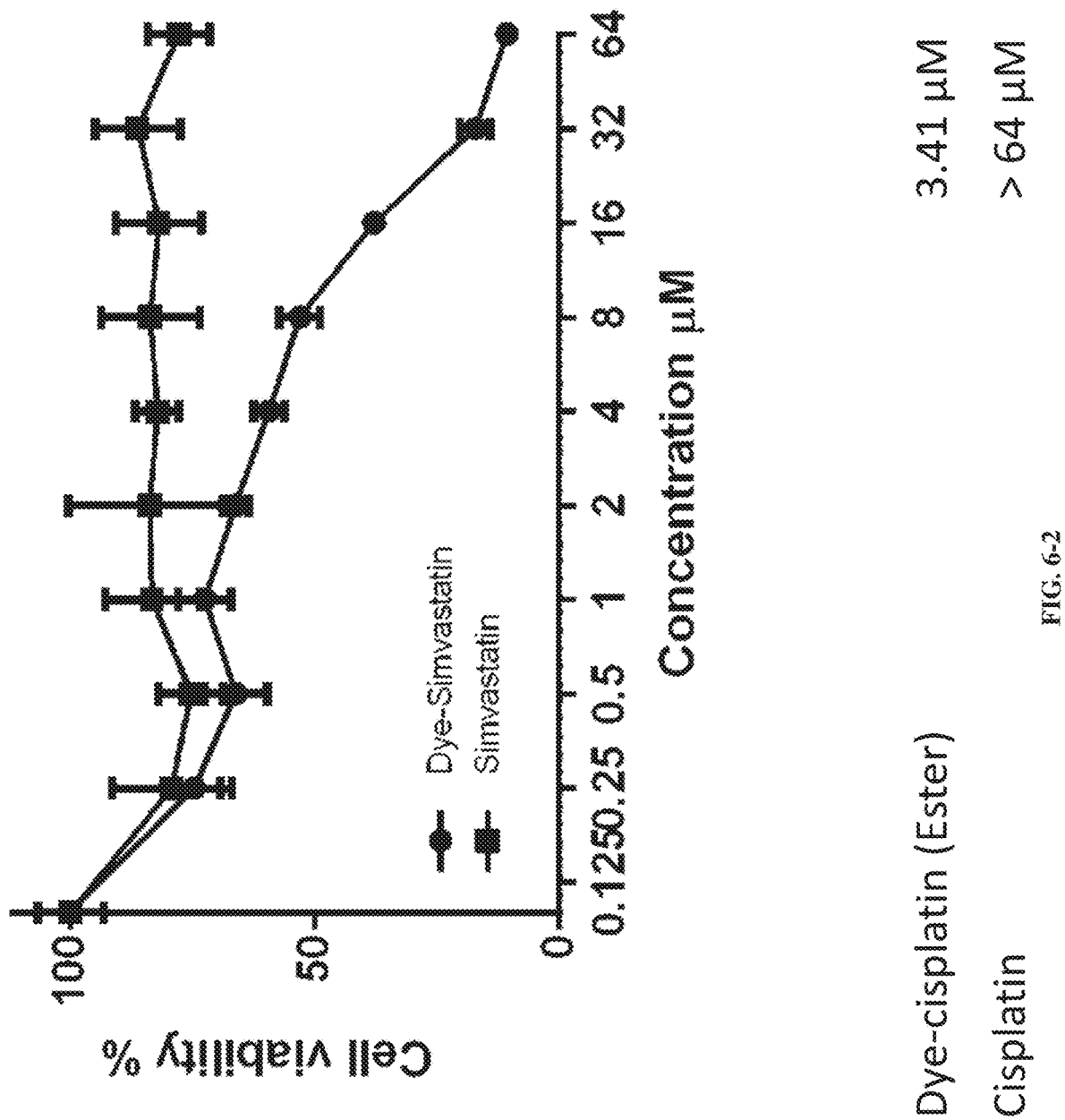

FIG. 6 shows the effectiveness of DZ-CIS ester in sensitizing CIS-resistant human ovarian cancer cell lines to anticancer effects of CIS. Human ovarian cancer cell strains, OV90 and OVCA 433, established from CSMC ovarian cancer patients, are CIS-resistant and have IC50s above 64 uM but responded when sensitized by DZ-CIS, displaying a significantly lower IC50 ranging from 3.41 uM to 7.04 uM. Clinical observations in the respective patients indicated overcoming therapeutic resistance to CIS by DZ-CIS ester.

Figure 7:
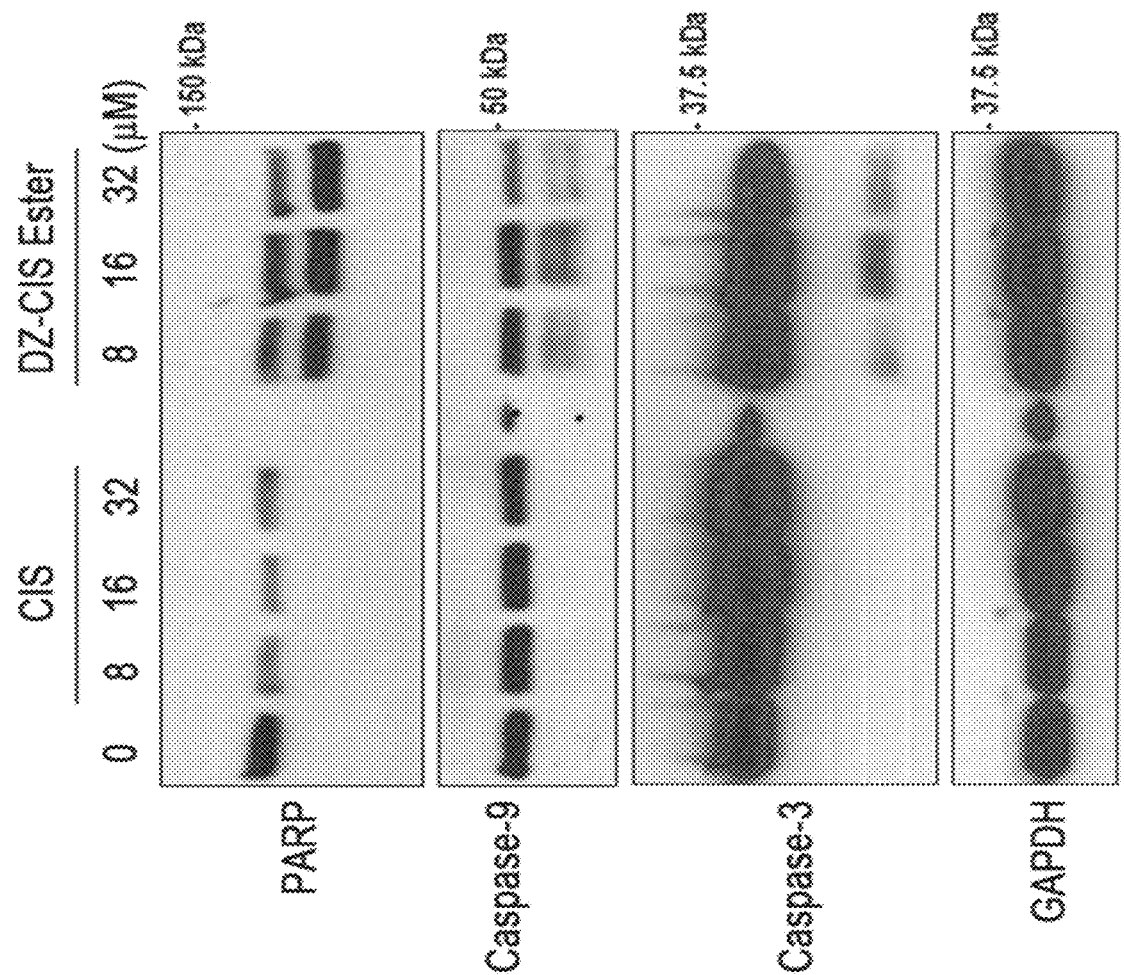
FIG. 7 (Right-Side) shows western blots of Cisplatin and DZ-CIS Ester for PARP, Caspase cleaved proteins, and GAPDH, as tested in human Burkitt lymphoma cell line Namalwa.
Figure 7:
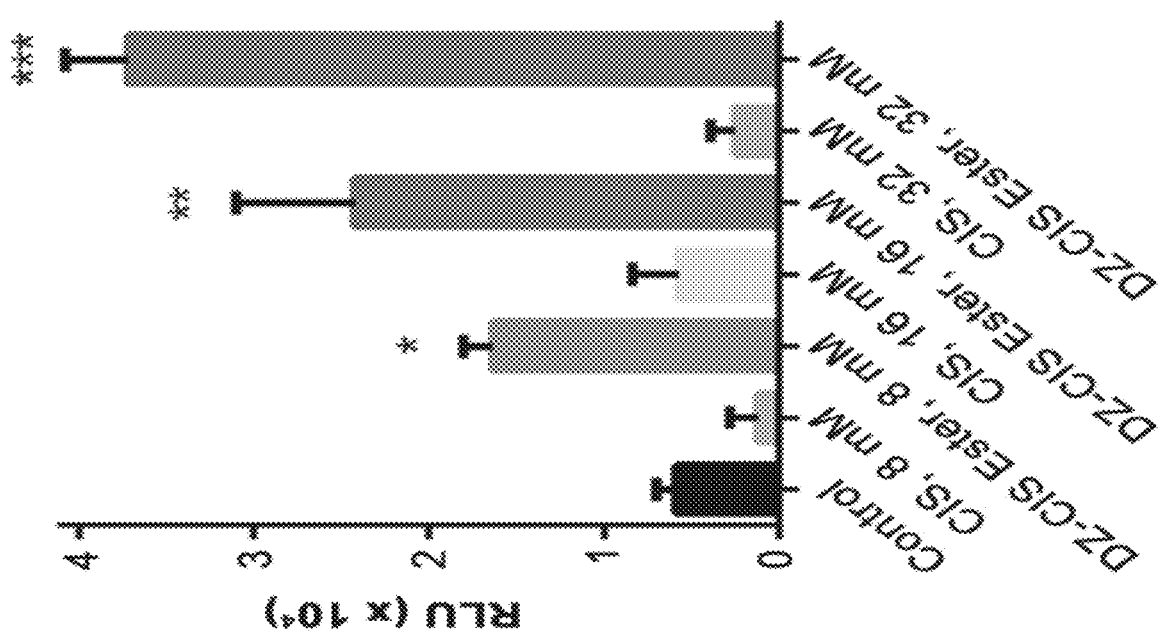

FIG. 7 shows that DZ-CIS inhibits the growth and induces apoptosis of human lymphoma and kidney tumor xenografts in mice. A human Burkitt lymphoma cell line, Namalwa is treated with CIS or DZ-CIS ester. Cells treated with DZ-CIS ester show significantly higher levels of apoptosis compared with CIS, as determined by apoptosis markers (CaspaseGlo 3/7 luminescent assay, and PARP and Caspase cleaved protein bands appearing for DZ-CIS but not CIS alone in the western blot).

Figure 8A:
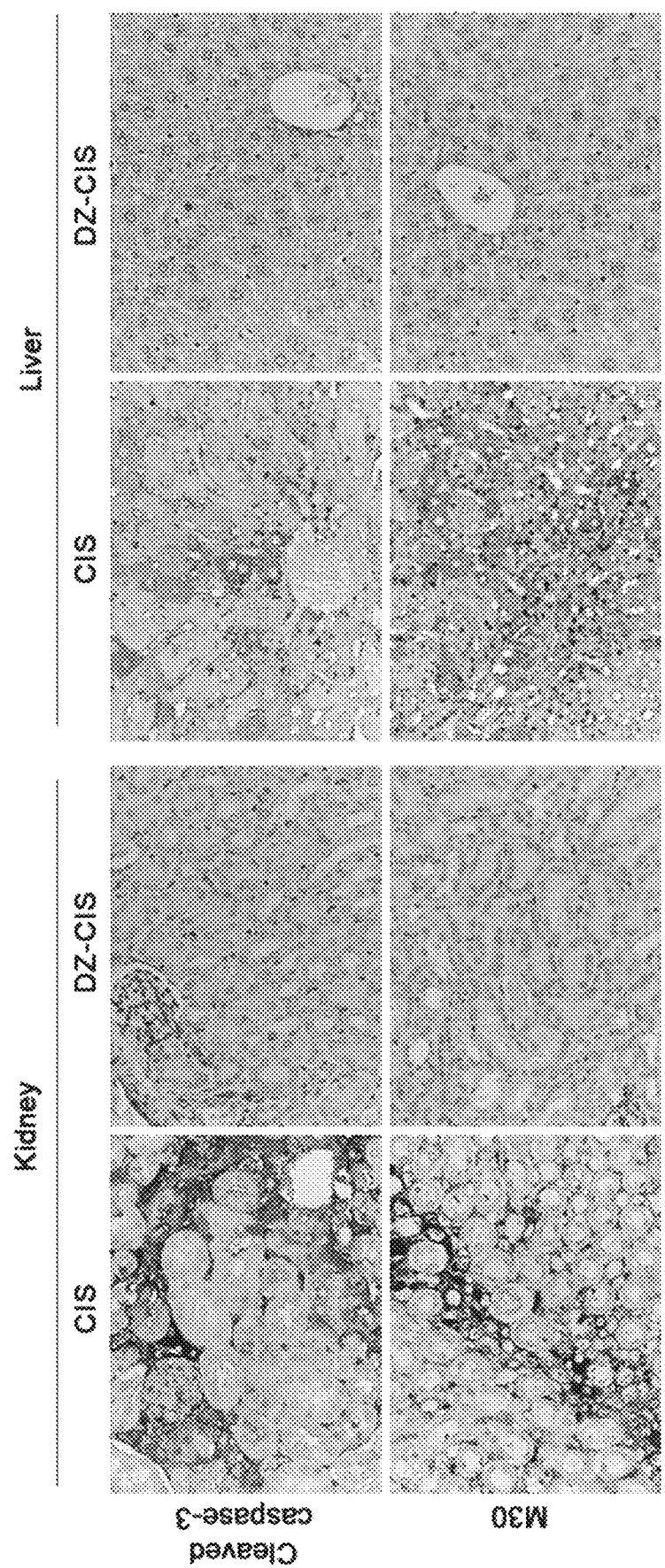
FIG. 8A shows a comparative immunohistochemical staining of normal kidney and liver demonstrating DZ-CIS protects from damage shown for CIS.

FIG. 8A shows a comparative immunohistochemical staining of normal mouse kidney and liver of mice administered with DZ-CIS or CIS, respectively. Apoptosis markers (cleaved caspas-3 and M30) are elevated in CIS but not in DZ-CIS treated normal mouse kidney and liver, showing protection by DZ-CIS from damage shown for CIS.

Figure 8B:
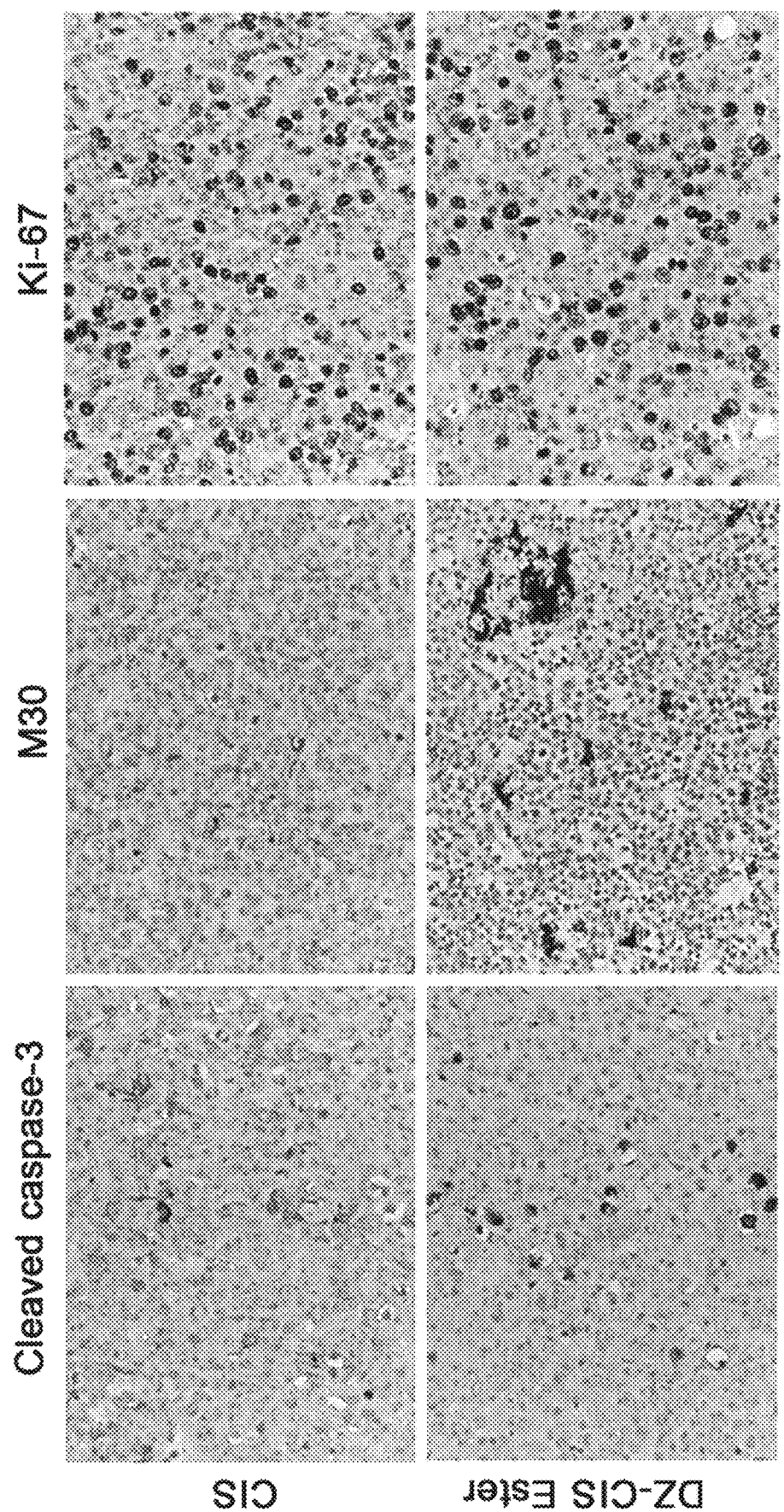
FIG. 8B shows a comparative immunohistochemical staining demonstrating that DZ-CIS increases apoptosis in mouse tumors.
Figure 9A:
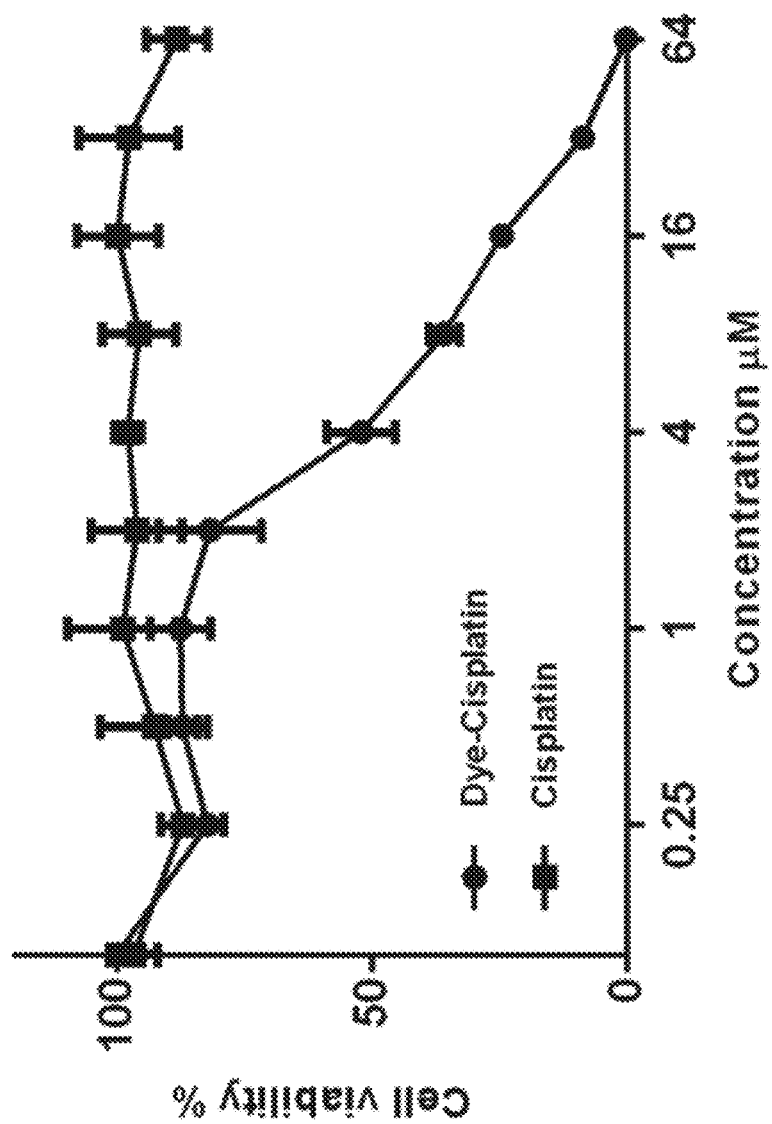
FIG. 9A shows the calculated 50% inhibitory concentration (IC50) of Cisplatin compared to DZ-CIS Ester as tested in human kidney cancer cell line Caki-1.
Figure 9B:
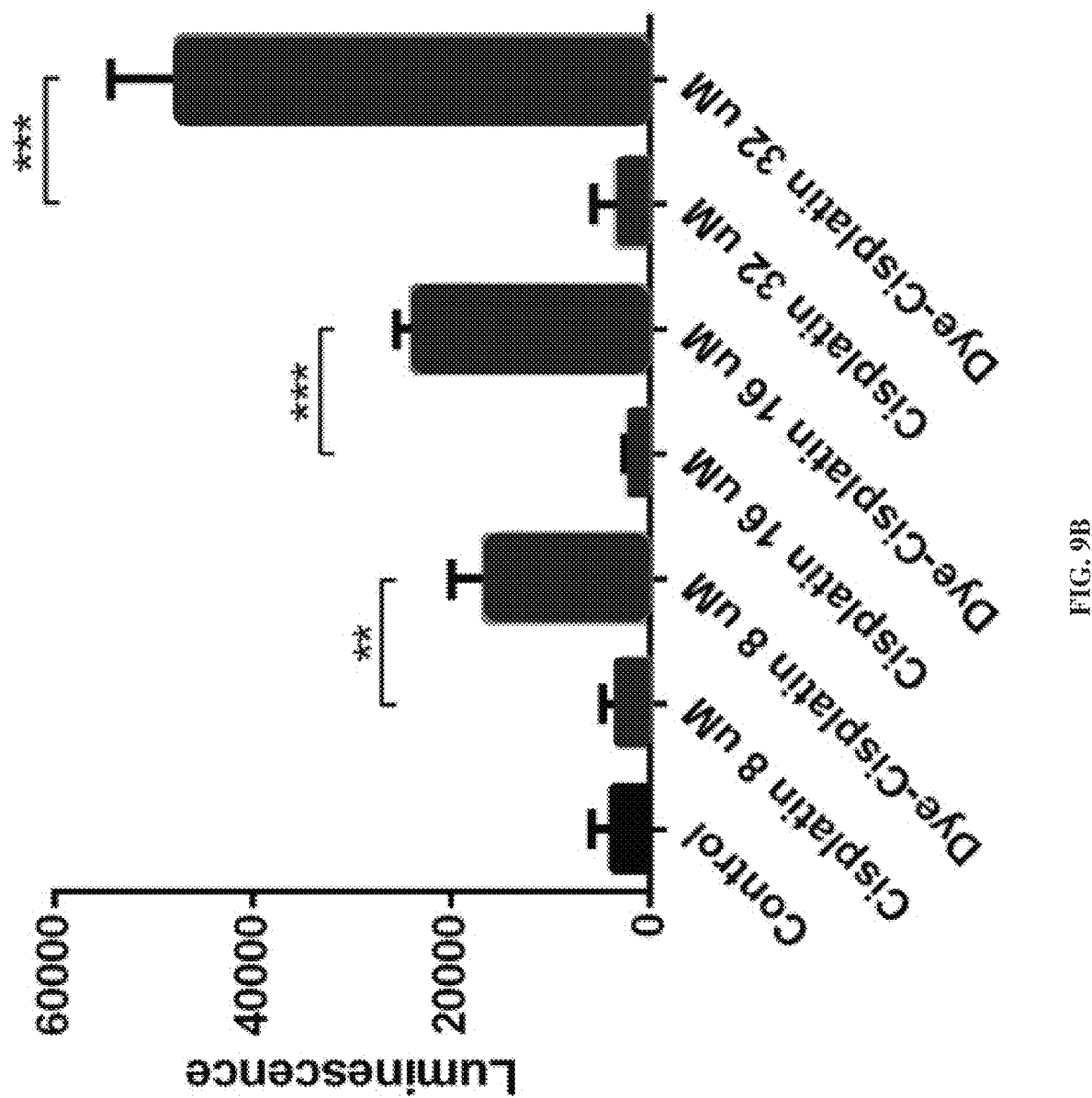
FIG. 9B shows the CaspaseGlo 3/7 luminescent assay of Cisplatin and DZ-CIS Ester as tested in human kidney cancer cell line Caki-1.
Figure 9C:
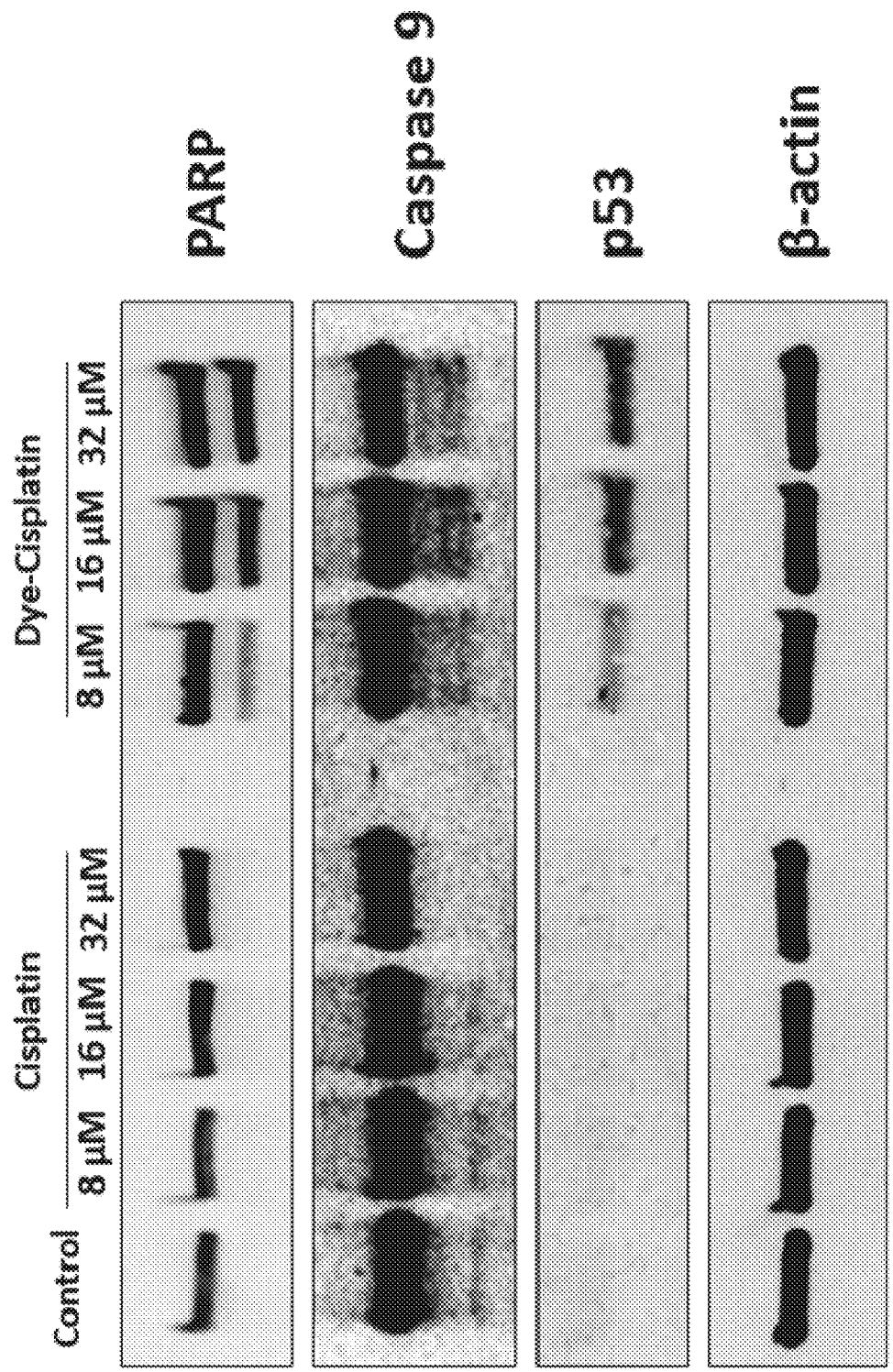
FIG. 9C shows western blots of Cisplatin and DZ-CIS Ester for PARP, Caspase 9, p53, and β-actin, as tested in human kidney cancer cell line Caki-1.
Figure 9D:
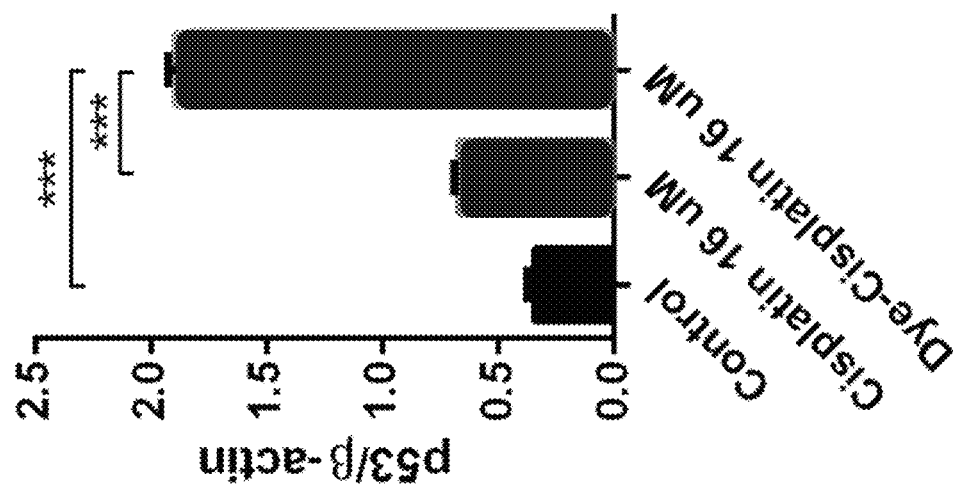
FIG. 9D shows elevated expression of p53 in human kidney cancer cell line Caki-1.

FIG. 8B shows a comparative immunohistochemical staining of mouse tumors (Namalwa human lymphoma xenograft tumors) administered with DZ-CIS or CIS, respectively. DZ-CIS increases apoptosis (elevated immunohistochemical markers, cleaved caspase-3 and M30), and decreases cell proliferation (immunohistochemical staining of Ki67), to a degree lesser than does CIS.

FIG. 9 shows growth inhibition of a human kidney cancer cell line by DZ-CIS, but not CIS (see upper left panel for graph of cell viability), and increased apoptosis in human kidney cancer cells (Caki) exposed to DZ-CIS, but not CIS, in concentration-dependent manner (see upper right panel for CaspaseGlo 3/7 luminescent assay). DZ-CIS, but not CIS, induces elevation of apoptosis related proteins, PARP, Caspase 9 and p53 (a tumor suppressor) expression (see lower panel).

Figure 10:
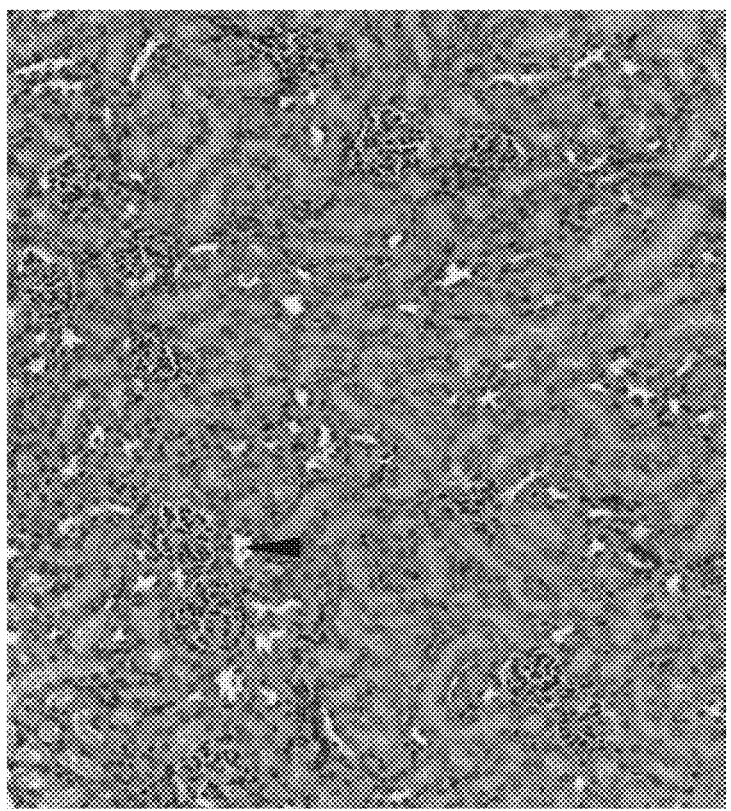
FIG. 10 (Right-Side) shows a histopathology of a mouse kidney treated with Cisplatin.
Figure 10:
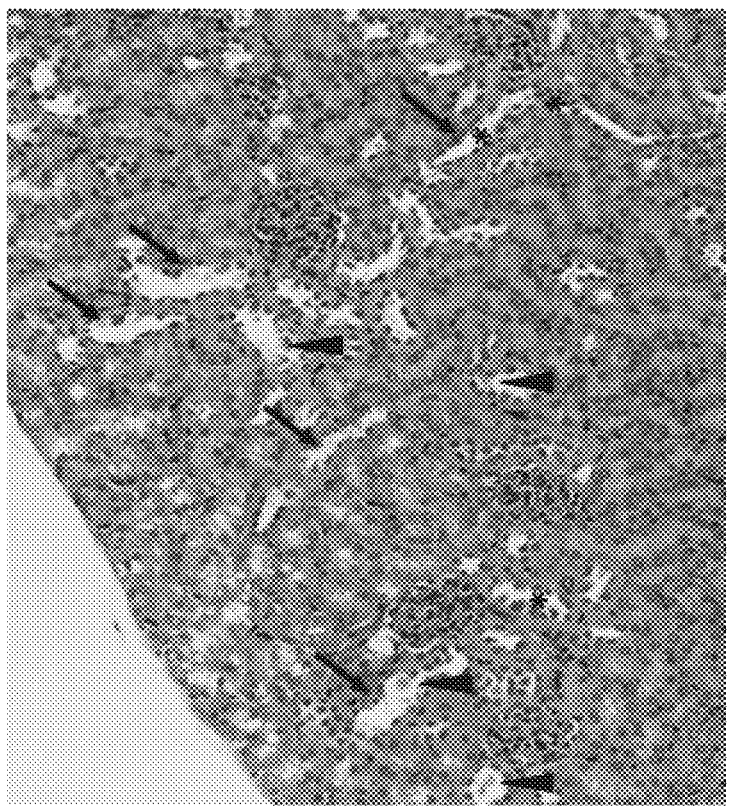

FIG. 10 shows a histopathology of normal kidney which demonstrates protection from CIS mediated damage by DZ-CIS. Mice treated with CIS (see left panel) showed severe damage as evidenced by necrosis, severe dilation and debris, compared to mice treated with DZ-CIS ester that were protected from such damage (see right panel).

Figure 11A:
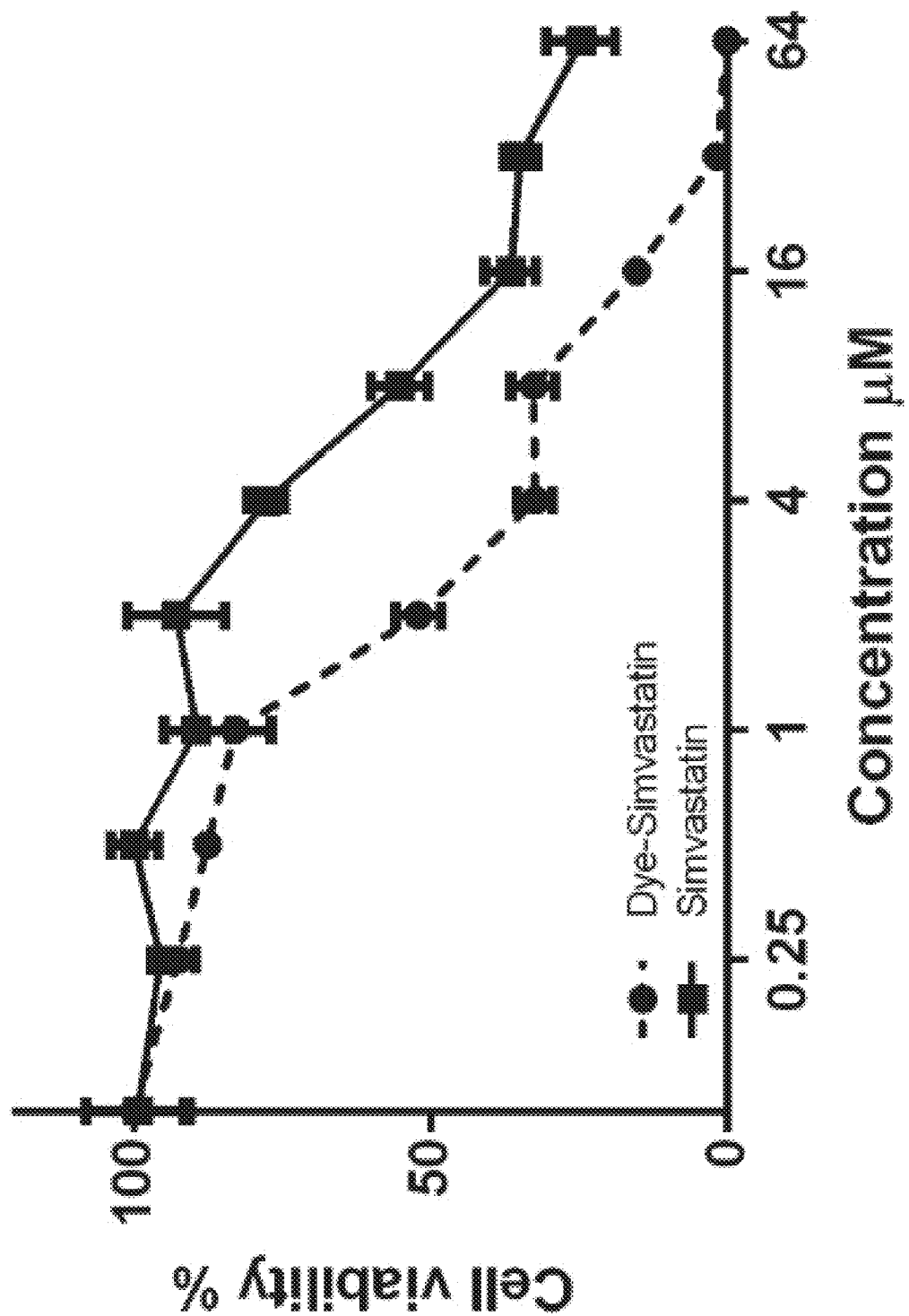
FIG. 11A shows the anticancer potency of Simvastatin compared to DZ-SIM Ester as tested in Ramos cells.
Figure 11B:
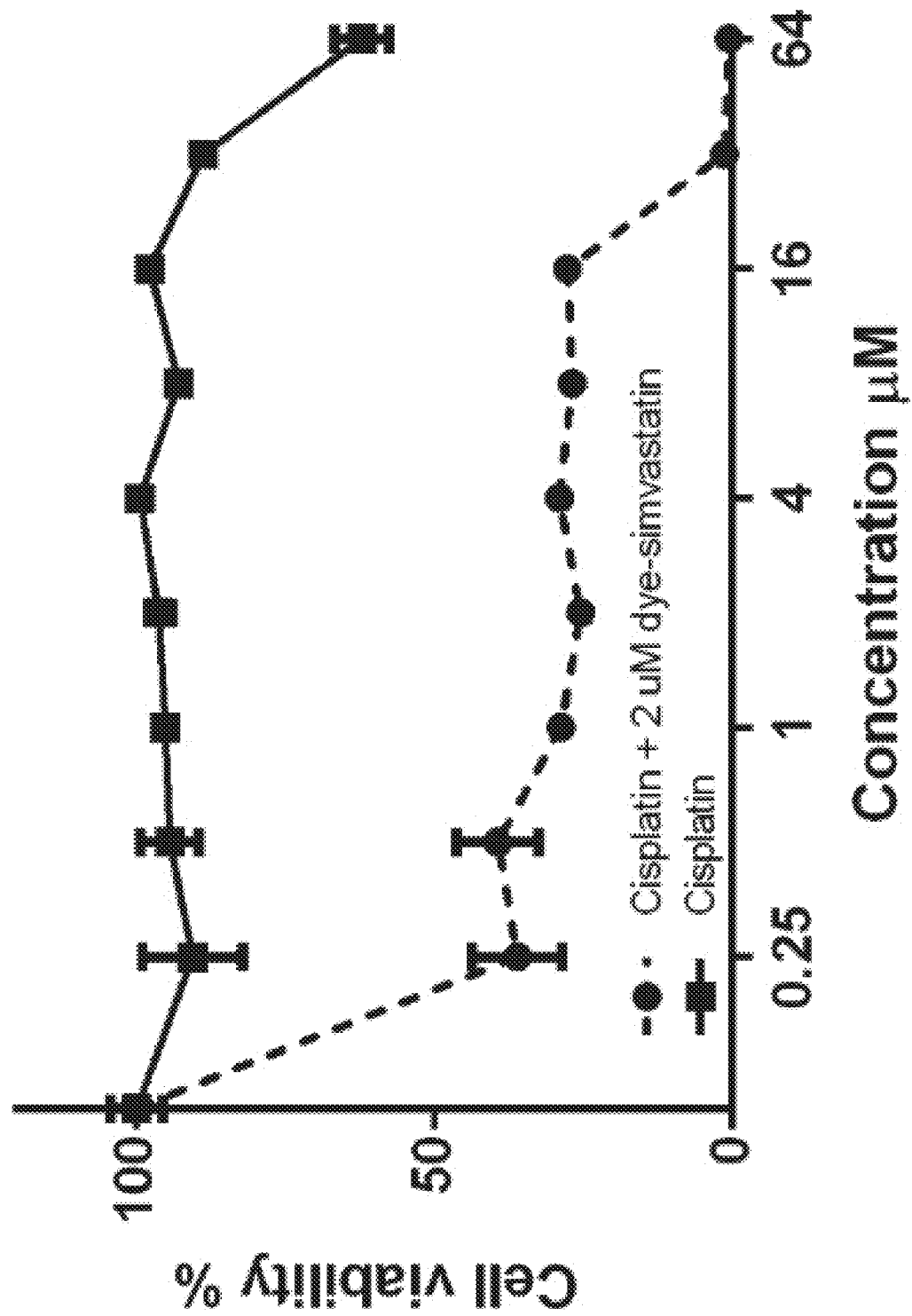
FIG. 11B shows the anticancer potency of Cisplatin compared to a combination of Cisplatin and DZ-SIM Ester as tested in Ramos cells.

FIGS. 11A and B shows graph of % cell viability that demonstrate that DZ-SIM ester (though only 5-fold more potent than SIM, FIG. 11A) synergistically increases anti-cancer CIS effects (as determined by % decreased cell viability) by over 190-fold (2 uM DZ-SIM ester, FIG. 11B). Cancer cells employed were Ramos cells, a B-cell lymphoma.

Figure 12:
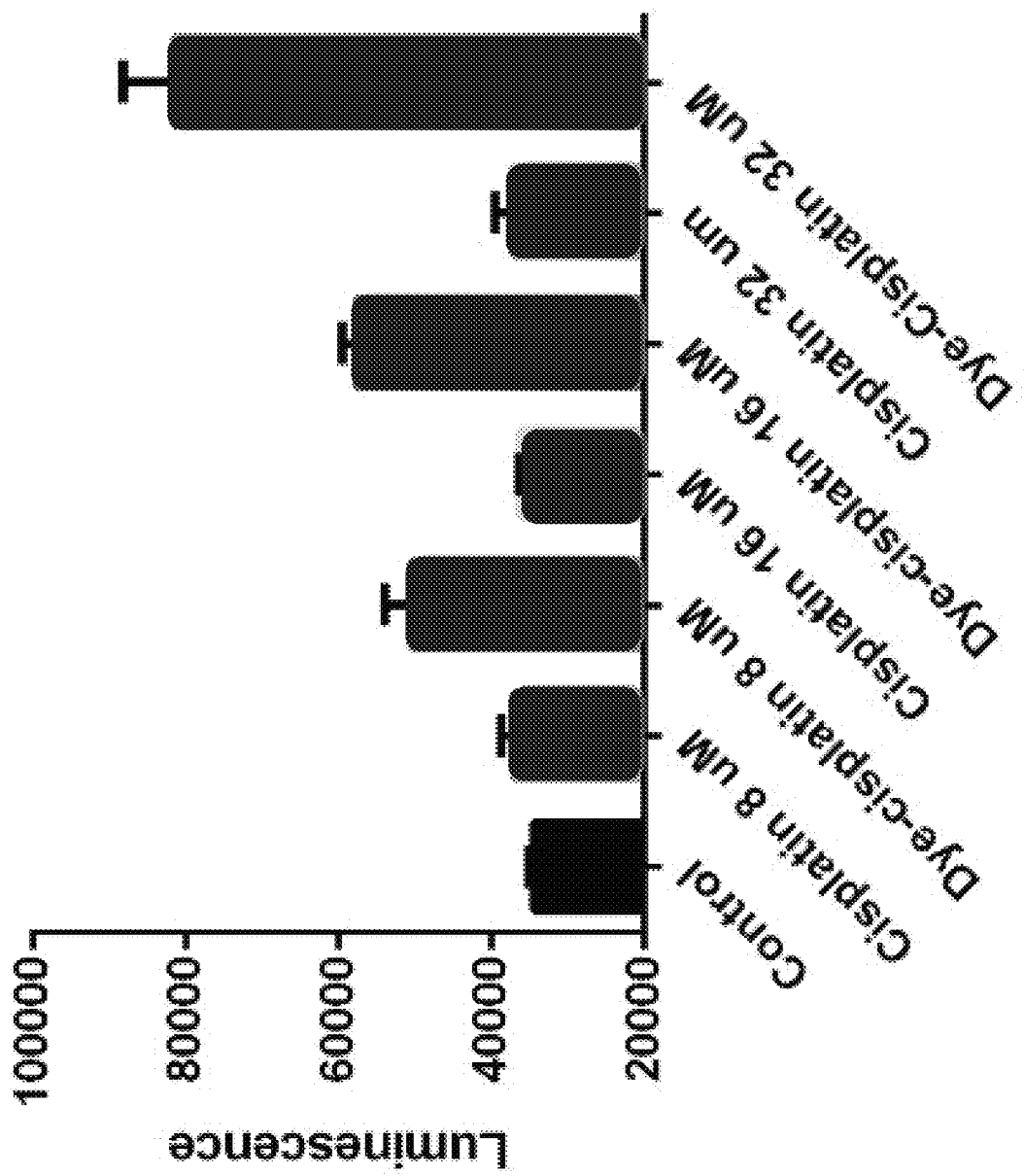
FIG. 12 shows that exposure of cancer cells to DZ-CIS more effectively induces apoptosis in cancer cells than exposure to CIS (B-cell lymphoma/Namalwa and renal Caki-1 cell lines).

FIG. 12 shows that exposure of cancer cells to DZ-CIS more effectively induces apoptosis in cancer cells than exposure to CIS (B-cell lymphoma cell lines/Namalwa and renal cancer cell lines Caki-1, as determined by Caspase-Glo 3/7 assay).

Figure 13:
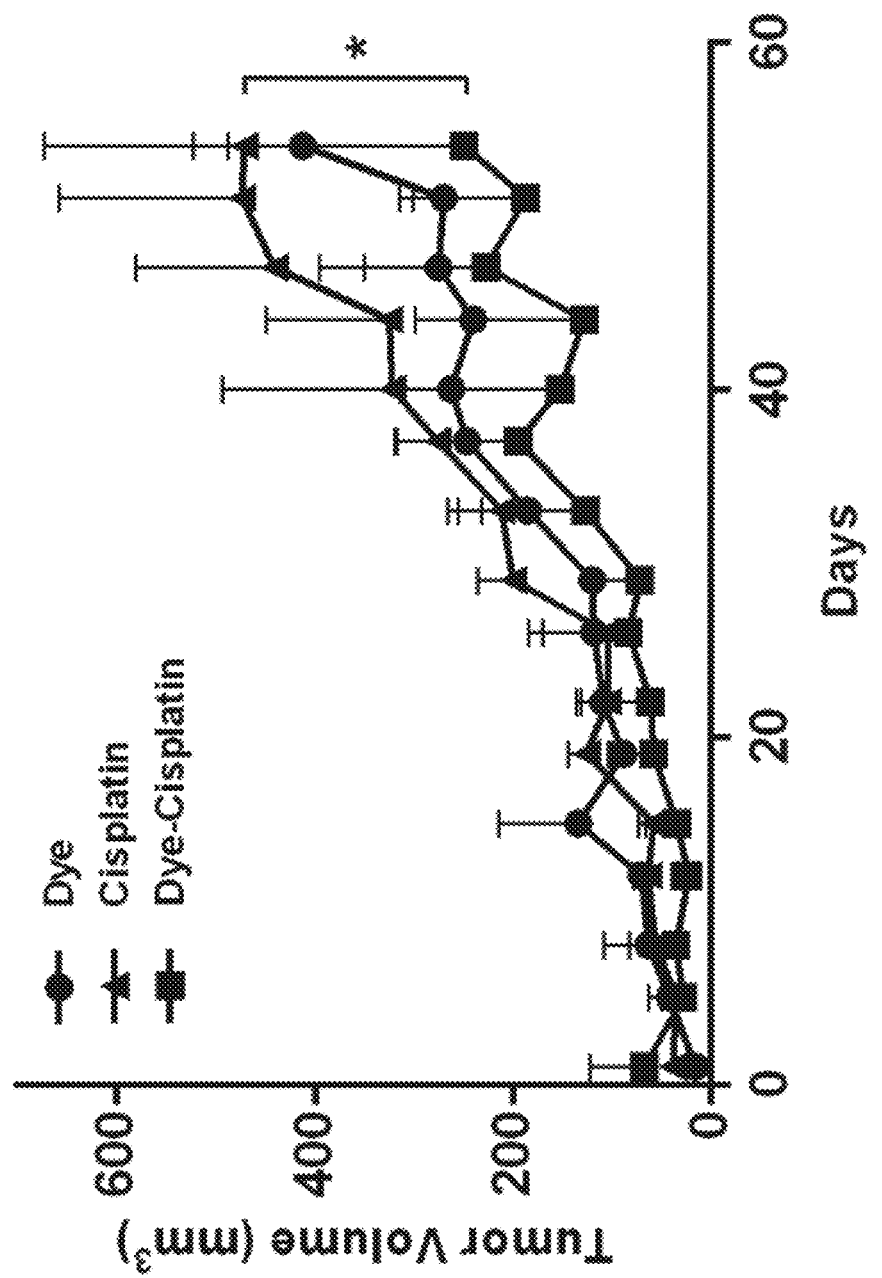
FIG. 13 shows that DZ-CIS is more effective than CIS in inhibiting renal tumor growth compared to CIS (renal cancer cell line ACHN in NCR-NU mice).

FIG. 13 shows that DZ-CIS is more effective than CIS in inhibiting renal tumor growth compared to CIS, as demonstrated with xenograft renal tumors (renal cancer cell line ACHN, in xenografts to immune-compromised mice NCR-NU mice). The graph shows lower tumor volumes for DZ-CIS compared to CIS.

Figure 14:
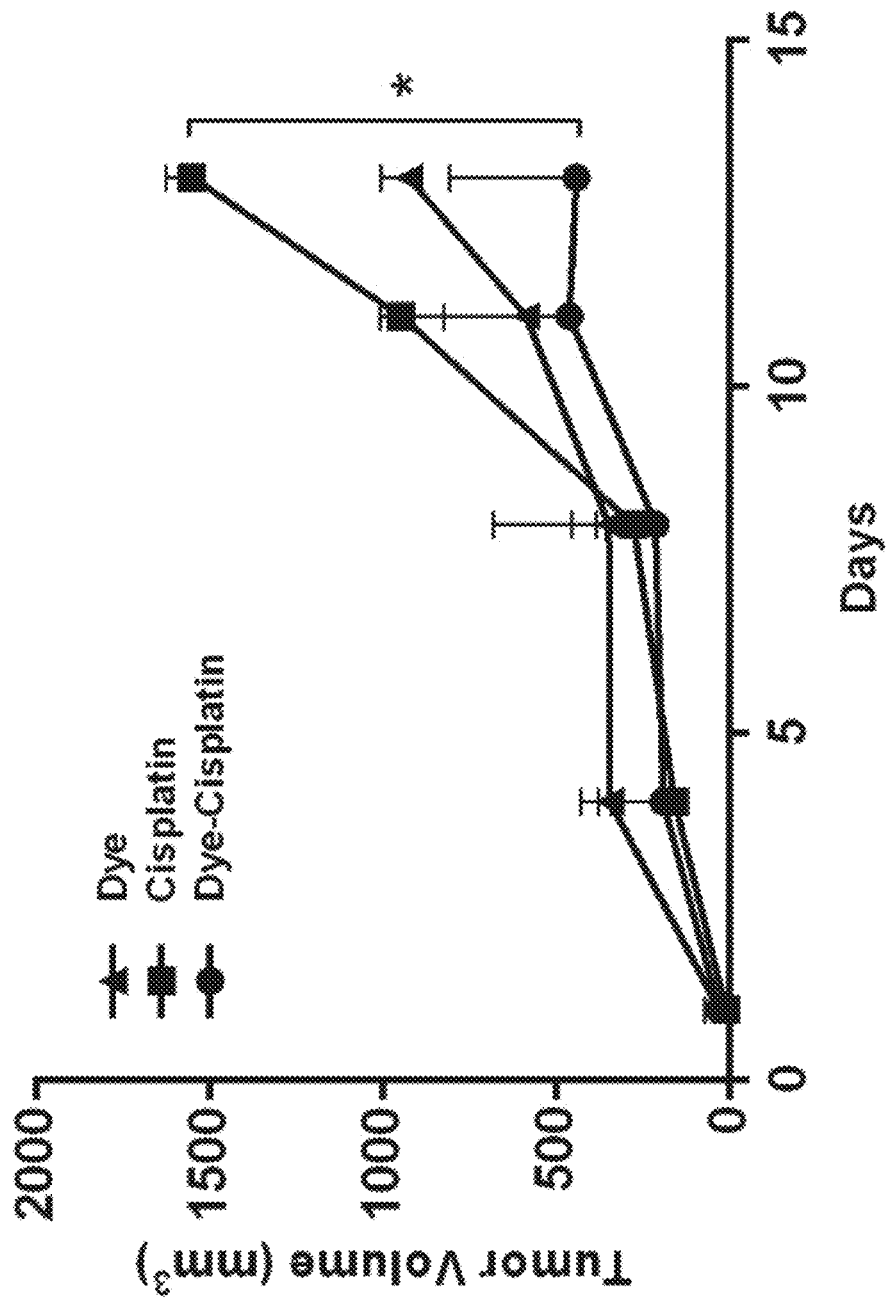
FIG. 14 shows that DZ-CIS is more effective than CIS in inhibiting kidney tumor growth in vivo (renal cancer Renca in Balb/c mice).

FIG. 14 shows that DZ-CIS is more effective than CIS in inhibiting kidney tumor growth in vivo, as demonstrated in a syngeneic mouse model of renal cancer (renal cancer cell line Renca employed in immune-intact Balb/c mice). The graph shows lower tumor volumes for DZ-CIS compared to CIS.

Figure 15:
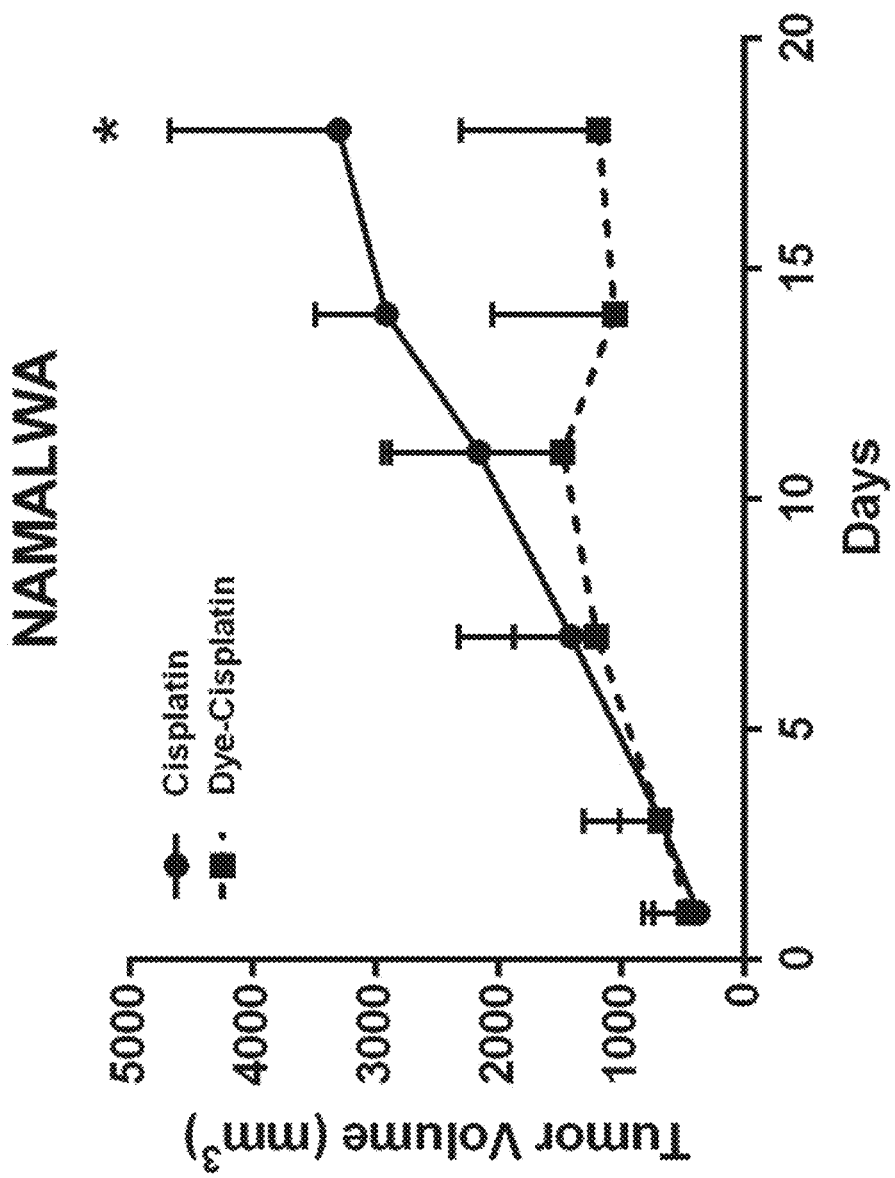
FIG. 15 shows that DZ-CIS is more effective than CIS in inhibiting the growth of B-cell lymphoma (Namalwa in NCR-NU).

FIG. 15 shows that DZ-CIS (ester or amide) is more effective than CIS in inhibiting the growth of B-cell lymphoma xenograft tumors, as demonstrated in a NCR-NU mice using Namalwa cells. The graph shows lower tumor volumes for DZ-CIS compared to CIS.

Figures 1, 16:
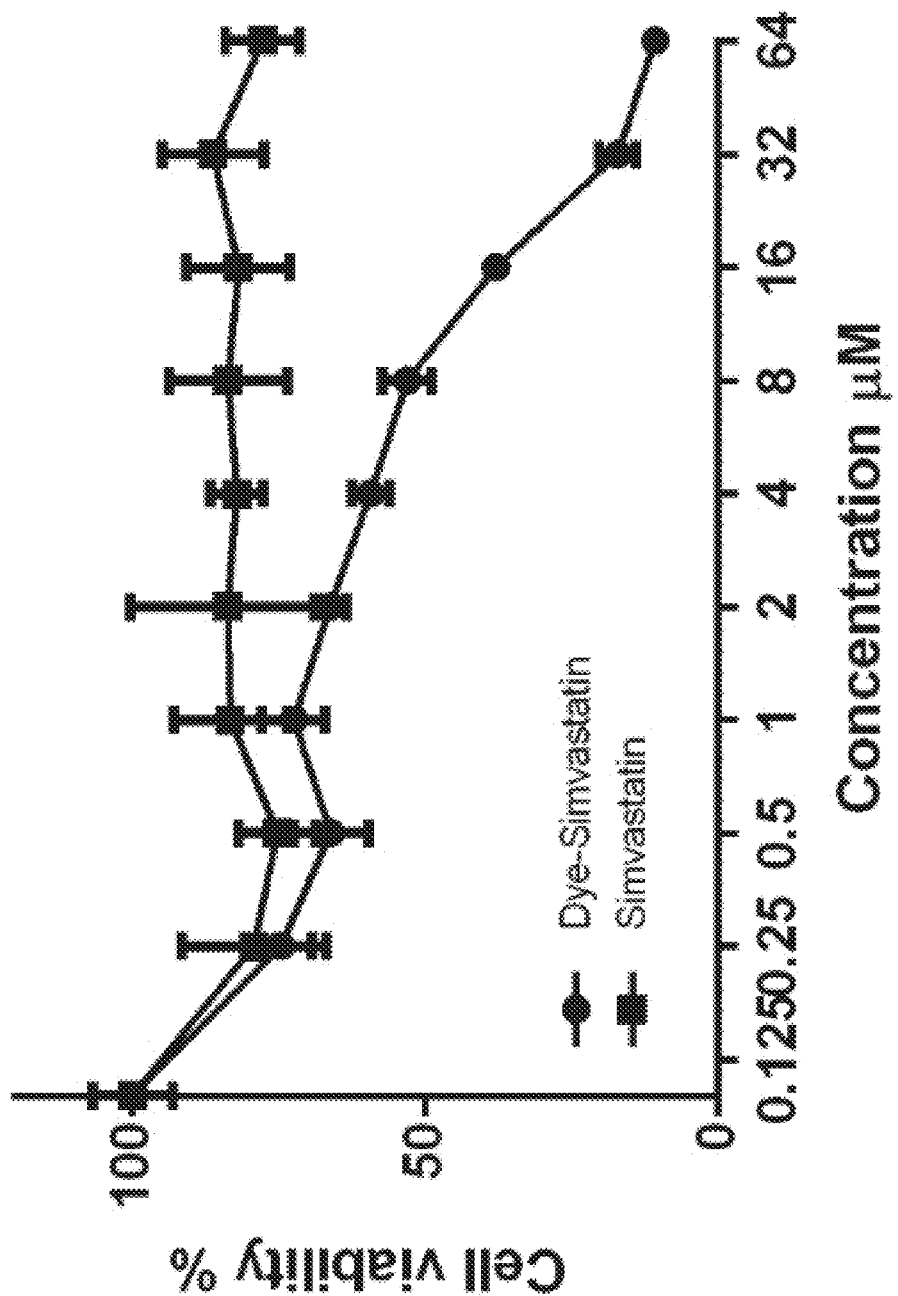
Figures 2, 16:
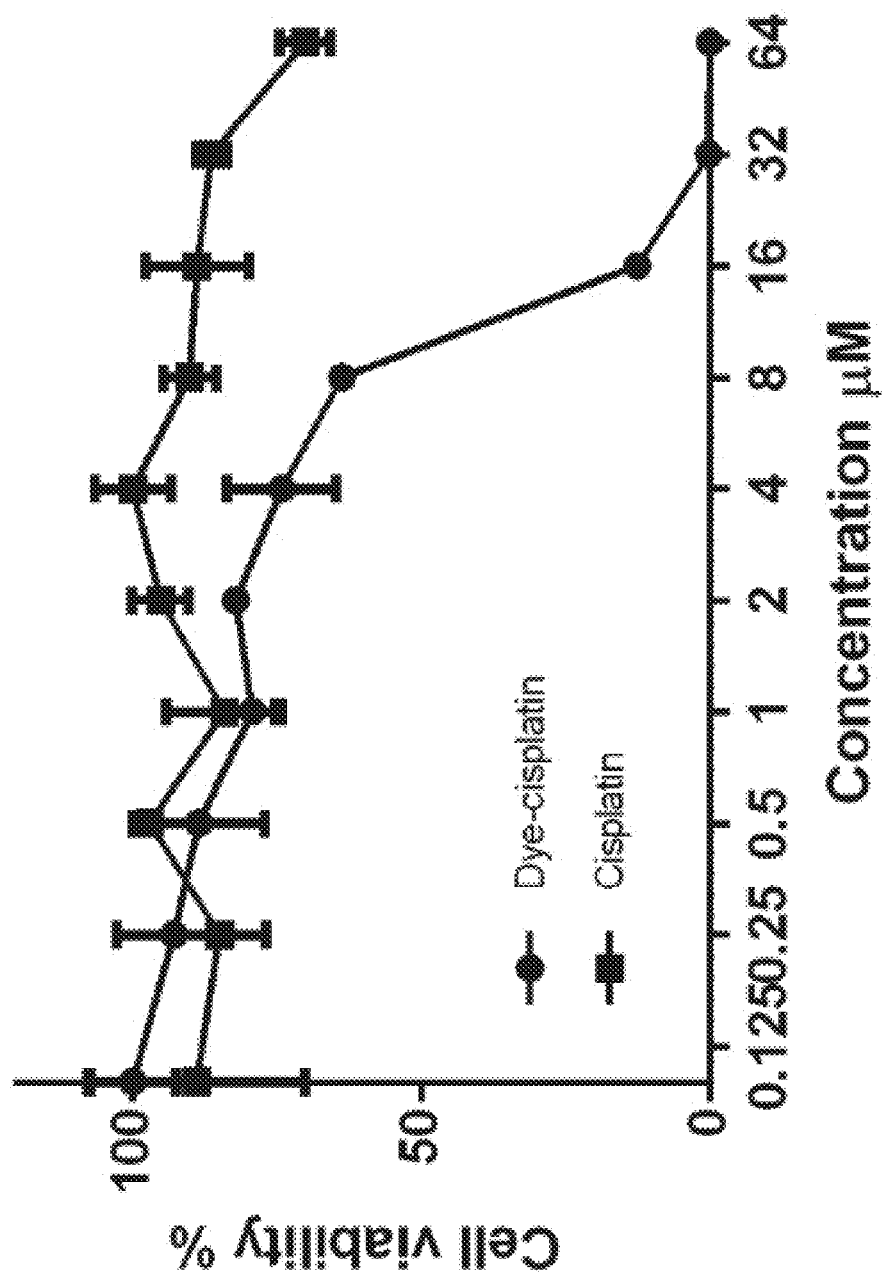

FIG. 16 shows growth inhibitory effects of DZ-SIM and of DZ-CIS as demonstrated in ovarian tumor cells (OV90 and OVCA433), determined by crystal violet assay. The graphs show lowered cell viability and a lowered IC50 for both DZ-SIM and DZ-CIS, compared to unconjugated SIM and CIS, respectively.

EXEMPLARY EMBODIMENTS

Exemplary Embodiments are generally performed as follows, unless otherwise noted. Simvastatin is purchased from Ark Pharm, Inc. (Arlington Heights, IL). Cisplatin (CIS) is purchased from MedKoo Biosciences, Inc. (Chapel Hill, NC). Dihydroartemisinin is purchased from TCI America (Portland, OR). All other chemicals and reagents are purchased from standard sources such as Sigma-Aldrich and/or VWR and are of highest quality available. Puromycin dihydrochloride was purchased from Alfa Aesar (Tewksbury, MA). Deionized water (18.2Ω) used for making solutions is obtained from Milli-Q Direct Ultrapure Water System from Millipore (Billerica, MA, USA). All intermediates are characterized by 1H NMR and mass analysis and the purity of compounds are analyzed by HPLC. 1H NMR data are collected on Bruker 400 MHz spectrometers using standard parameters; chemical shifts are reported in ppm (δ) in reference to residual non-deuterated solvent. ESI mass spectroscopy analysis is performed using a Thermo Fisher LTQ Orbitrap Elite system. IC50 is the half maximal inhibitory concentration and determined is determined by crystal violet assay unless otherwise noted.

The crystal violet assay is performed as follows, unless otherwise noted. Cell lines are supplemented with RPMI 1640 medium, 10% fetal bovine serum, 1% PenStrep, and placed in a humidified atmosphere containing 5% CO2 at 37° C. 5,000 cells/well renal cancer cells and 10,000 cells/well lymphoma cells are seeded in 96 well plates in 100 microliter medium/per well for 24 h. Cell lines are exposed to exponentially increasing concentrations of either CIS or DZ-CIS ester ranging from 0.25 μM to 64 μM for 72 h. Renal cancer cells are fixed with 3.7% paraformaldehyde for 15 minutes and are stained with Crystal violet solution (0.5% in 25% methanol) for 30 minutes. After rinsing with water cell layers are dried and decolorized with Sorenson citrate with shaking for 20 minutes. Light absorption of the extracted supernatant is read at 595 nm. Lymphoma cell growth was evaluated using MTT and cells are incubated for 4 hours. 100 microliters of isopropanol is added, and the extracted supernatant fraction is read at absorption maximum of 595 nm.

Standard cell culture conditions typically are RPMI 1640 medium, 10% fetal bovine serum, 1% PenStrep, and are performed in a humidified atmosphere containing 5% CO2 at 37° C. Generally, 5,000 cells/well-10,000 cells/well are seeded in 96 well plates in 100 microliter medium/per well for 24 h, or as described in Example 16, unless otherwise noted. Certain cells require specialized media, growth factors, antibiotics, or culture condition adjustments, as will be apparent to a person of ordinary skill in the art.

DZ1 may be synthesized as follows, using deionised Ultrapure water (resistivity, 18.2 M (2 cm) and High-performance liquid chromatography (HPLC) grade solvents. Analytical reversed-phase (RP) high-performance liquid chromatography (HPLC) is performed on an Agilent system with a 1260 Infinity Diode-Array Detector with an Apollo C18 RP column (5 μm, 150×4.6 mm). The mobile phase changes from 50% solvent A (0.1% trifluoroacetic acid in 80% water) and 50% solvent B (0.1% trifluoroacetic acid in 80% aqueous acetonitrile) to 100% solvent B over a period of 30 min at a flow rate of 1 mL/min (monitoring at 254 and 780 nm). ESI-time-of-flight mass spectroscopy (ESI-TOF-MS) analysis is performed on a LCT Premier Mass Spectrometer. 1HNMR spectra are recorded on a Bruker 400 MHz NMR spectrometer. A reaction scheme for DZ synthesis is shown below.

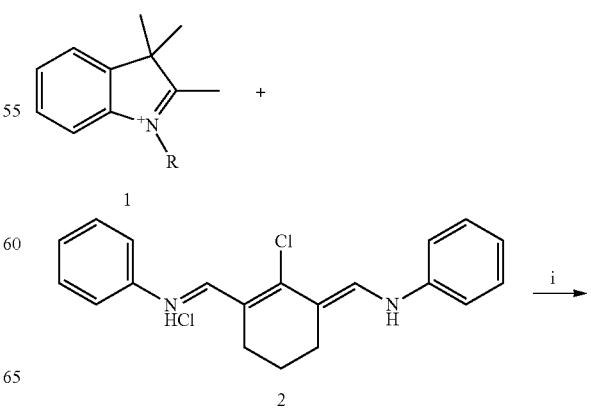

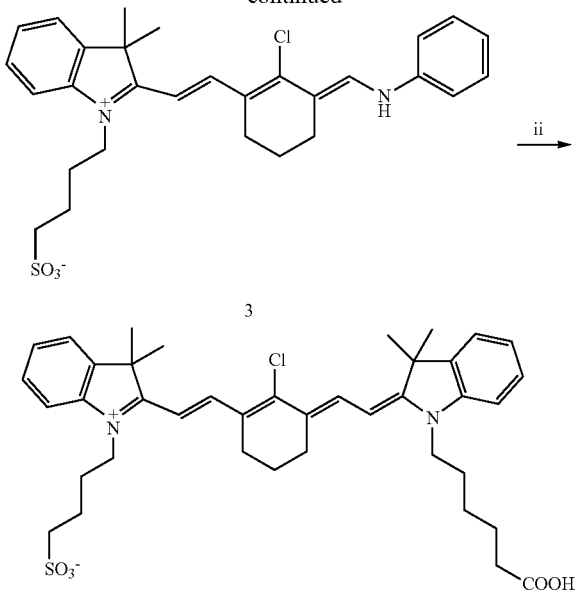

1a: R = ——(CH$_2$)$_4$SO$_3$H
1b: R = ——(CH$_2$)$_5$COOH

Reagents and conditions: (i) 1a, NaOAc, EtOH, reflux, 3 h; (ii) 1b, NaOAc, EtOH, reflux, 3 h Synthesis of compound 3: To the mixture of 1a (2.0 g, 6.78 mmol) and Vilsmeier-Haack reagent 2 (3.0 g, 8.36 mmol) in EtOH (50 ml) is added CH$_3$COONa (0.56 g, 6.78 mmol), the resulted mixture is heated to reflux for 3 h. The reaction mixture is poured into 200 ml of ice-water. The precipitate is collected and recrystallized from ethanol-acetone to afford desired product 3 as a dark blue solid (2.1 g, yield 56%). 1H NMR (DMSO-d6, 400 MHZ) δ 10.20 (s, 1H), 8.43 (d, 1H, J=16 Hz), 8.19 (s, 1H), 7.71 (m, 2H), 7.53-7.39 (m, 6H), 7.16 (m, 1H), 6.62 (d, 1H, J=12 Hz), 4.38 (m, 2H), 2.71 (m, 4H), 2.52 (m, 2H), 1.87 (m, 4H), 1.75 (m, 2H), 1.69 (s, 6H). MS (ESI-TOF) C$_{29}$H$_{34}$ClN$_2$O$_3$S [M+H]$^+$: 525.1979.

Synthesis of DZ dye 4: To the mixture of 1b (0.5 g, 1.4 mmol) and compound 3 (1 g, 1.9 mmol) in EtOH (20 ml) is added CH$_3$COONa (128 mg, 1.5 mmol), the resulting solution is heated to reflux for 3 h. The reaction mixture is poured in to 100 ml of water. The solid is collected and crystallized from methanol-water to afford desired product 4 as a dark green solid (0.8 g, yield 73%). 1H NMR (DMSO-d6, 400 MHz) δ 11.99 (s, 1H), 8.26 (m, 2H), 7.61-7.22 (m, 8H), 6.43 (d, 1H, J=16 Hz), 6.23 (d, 1H, J=16 Hz), 4.23 (m, 4H), 2.72 (m, 4H), 2.21 (m, 2H), 1.86 (m, 4H), 1.73 (m, 6H), 1.67 (s, 6H), 1.66 (s, 6H), 1.57 (m, 2H), 1.40 (m, 2H). MS (ESI-TOF) C$_{40}$H$_{50}$ClN$_2$O$_5$S [M+H]$^+$: 705.3152. HPLC retention time: 17.375 min.

Caspase-Glo® 3/7 Assay (Promega) is a homogeneous, luminescent assay that measures caspase-3 and-7 activities that provides a luminogenic caspase-3/7 substrate, which contains the tetrapeptide sequence DEVD, in a reagent optimized for caspase activity, luciferase activity and cell lysis. A single Caspase-Glo 3/7 Reagent in an "add-mix measure" format results in cell lysis, followed by caspase cleavage of the substrate and generation of a "glow-type" luminescent signal, produced by luciferase. Luminescence is proportional to the amount of caspase activity present. Caspase-Glo® 3/7 Reagent is prepared, mixed and the reagent and the 96-well plate containing cells are equilibrated to room temperature. 100 μl of Caspase-Glo® 3/7 Reagent is added to each well of a white-walled 96-well plate containing 100 μl of blank, negative control cells or treated cells in culture medium. The plate is covered with a plate sealer or lid, and contents gently mixed using a plate shaker at 300-500 rpm for 30 seconds. The plate is incubated at room temperature for 30 minutes to 3 hours, depending upon the cell culture system (optimal incubation period determined empirically). Luminescence of each sample is measured in a plate-reading luminometer.

Example 1

The example shows that DZ-CIS (ester or amide) is more effective than CIS in both CIS-resistant and non-resistant lung cancer. Results include non-small cell lung cancer (NSCLC) cell lines and small cell lung cancer cell lines (SCLC), as shown in the table below. The NSCLC cell lines include parental A-549 (a human NSCLC cell line), A-549/DDP (its CIS-resistant isogenic line), 95D (a metastatic variant of the parental non-metastatic 95C), and a squamous YTMLC line. H446 is a SCLC cell line. Cells are cultured in medium containing 10% FBS grown as monolayers and treated with different concentrations of the drugs indicated below for 72 h. IC50s (defined as the concentration that resulted in a 50% decrease of cell proliferation as assessed by a Crystal Violet assay) are determined in these cultured cells. The data in the table below represents the mean±Standard Error of the Mean (SEM) from at least three independent experiments. Drugs tested and compared include CIS and DZ-CIS ester. Each drug is used as single agent. DZ-CIS amide achieves similar results. FIG. 1 in panels A-F shows graphs of a comparison of antitumor activities of CIS versus DZ-CIS ester in both human non-small cell lung cancer (NSCLC) and human small cell lung cancer (SCLC) cell lines. The calculated 50% inhibitory concentration (IC50) is shown on a logarithmic scale for these human lung cancer cell lines, and represents the representative means+/−SEM for two assays done in quadruplicate. The viability of control cells treated with dimethyl sulfoxide is assigned a value of 100. The results show that DZ-CIS is consistently more effective than CIS in a variety of different types of human lung cancer cells.

| | IC50 | | | | | |
|---|---|---|---|---|---|---|
| | NSCLC | | | | | |
| Drugs | A549 parental | A549/DDP (Cisplatin Resistant) | 95D (Met) | 95C (Non-Met) | YTMLC | SCLC H446 |
| CIS | 26 ± 1.2 | 90 ± 1 | >100 ± 1.1 | 12.7 ± 1 | 16.2 ± 1 | 107.3 ± 1 |
| DZ-CIS ester | 1.8 ± 1 | 10.2 ± 11.2 | 13.7 ± 1.3 | 2.4 ± 1.1 | 2.2 ± 1 | 23.4 ± 1 |

Example 2

The example shows combination therapy results which demonstrate that DZ-SIM-Ester and DZ-SIM amide have sensitizing antitumor effects when combined with CIS. Results for an in vitro model of human lung cancer in the presence or absence of sensitization by DZ-SIM ester or DZ-SIM amide in different concentrations are shown in the table below, also see graphs of cell survival over CIS concentration illustrating the results in FIG. 2. The example is performed as indicated in Example 1, with changes in cell lines used, and in drugs and their concentrations used, as indicated below. A549 or A549/DDP cells are treated with variable concentrations of CIS and a constant concentration of DZ-SIM ester or DZ-SIM amide at the indicated doses for 72 h. Cell proliferation is determined by a Crystal Violet assay. The data represent the mean+/−SEM for two assays done in quadruplicate. The viability of control cells treated with dimethyl sulfoxide is assigned a value of 100. Cells are exposed to CIS in combination with DZ-SIM (ester or amide, respectively), or to CIS alone in a concentration of up to 100 µM. The mean of the IC50 determined from at least three independent experiments is shown in the table below. The results indicate that combinations with DZ-SIM ester or with DZ-SIM amide are more effective than CIS alone in both resistant and non-resistant lung cancer cell lines. As shown, the IC50 of CIS can be dramatically reduced by up to 200-or-7-fold respectively by combination with DZ-SIM ester or DZ-SIM amide. The results demonstrate that DZ-SIM ester and DZ-SIM amide sensitize cancer cells to CIS and can provide improved therapeutic responses, or similar responses at a lower dose. These sensitizers are thus useful to achieve a therapeutic effect in CIS-resistant patients, to avoid development of resistance, and/or to reduce the CIS dose (and thus its toxic effects) without affecting the antitumor/cancer effect of CIS in CIS, in resistant or non-resistant patients.

|  | A549 Mean (95% CI) | A549/DDP Mean (95% CI) |
| --- | --- | --- |
| CIS | 26 (17-40) | 87.6 (78.4-98.8) |
| CIS + 1 uM DZ-SIM ester | 8.8 (7.5-10.4) | 5.6 (3.6-8.7) |
| CIS + 2 uM DZ-SIM ester | 4.3 (3-6) | — |
| CIS + 3 uM DZ-SIM ester | 0.8 (0.5-1.5) | — |
| CIS + 4 uM DZ-SIM ester | 0.12 (0.06-0.2) | — |
| CIS + 4 uM DZ-SIM amide | — | 13.6 (7.6-24.3) |
| CIS + 7 uM DZ-SIM amide | 1 (0.6-1.4) | — |

FIG. 2 CIS in panels A-D shows a comparison of antitumor activities of CIS alone versus a combination of CIS with DZ-SIM ester or amide in NSCLC cells (A 549 and and its isogenic CIS-resistant lung cancer cell line). The results in panels A-D show that DZ-SIM can sensitize NSCLC cells to the antitumor effects of CIS. In the presence of either DZ-SIM ester or amide, CIS IC50s are greatly reduced demonstrating that NSCLC cells can be sensitized to the antitumor effects of CIS by DZ-SIM ester/amide, thus allowing to greatly reduce the dose of CIS without compromising its antitumor effect.

Example 3

The example shows that DZ-SIM ester is as or more effective than SIM to sensitize human and mouse pancreatic cancer cells to cancer drugs with antitumor effects.

Figure 3C:
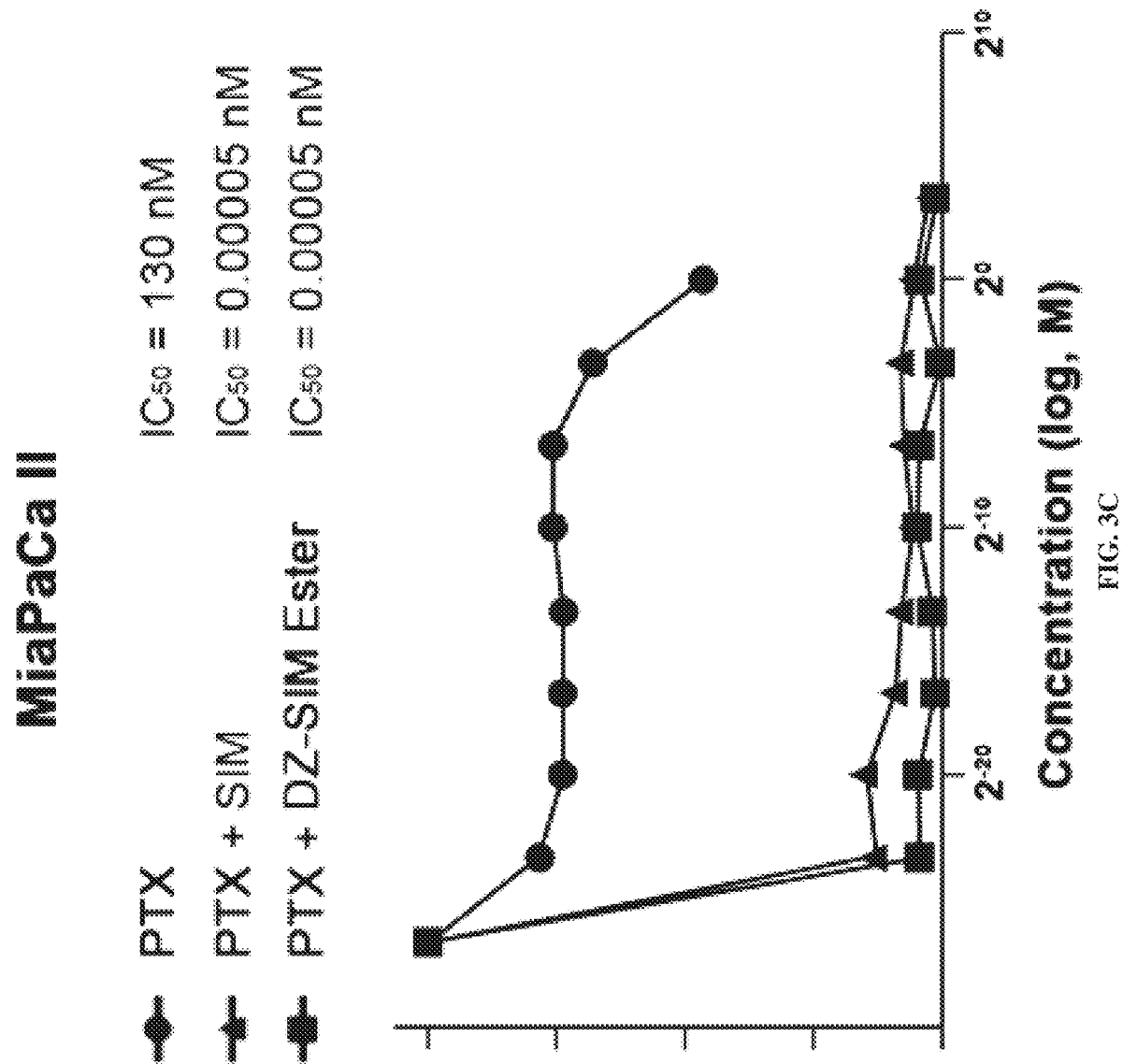
FIG. 3C shows the calculated 50% inhibitory concentration (IC50) of conventional chemotherapeutic drug Paclitaxel alone and in combination with SIM or DZ-SIM Ester, as tested in mouse pancreatic cancer cell line MiaPaCa II.

Pancreatic cancer cells are cultured for 72 hours in vitro and exposed to the conventional chemotherapeutic drugs Gemcitabine (GEM) and Paclitaxel (PAC), known to inhibit pancreatic cancer growth in patients. GEM (or PAC) alone are compared to a combination with SIM, or a combination with DZ-SIM. As shown in the graphs of FIG. 3, DZ-SIM ester is a more effective sensitizer to GEM or PAC than SIM in CTC-752-S-1 in human pancreatic cancer cells (freshly cultured cells from blood collected from human pancreatic cancer patients, CTC-752-S-1). Mouse pancreatic cancer cell line, MiaPaCa II, derived from transgenic KPC mice, showed similar sensitization for DZ-SIM and SIM. Representative results are illustrated in the graphs in FIG. 3.

Similarly, results indicate that DZ-SIM and SIM about equally sensitize mouse pancreatic cancer cell line NKPC-961 (a mouse pancreatic carcinoma cell line established from a pancreatic cancer KPC transgenic mouse model with introduced K-ras and p53 mutations) to therapeutic drugs CIS and GEM, with both DZ-SIM and SIM enhancing the cytotoxicity of GEM and of CIS. Representative results are illustrated in FIG. 3B.

Example 4

The example shows that DZ-SIM (ester or amide), but not SIM alone, inhibits the growth of tumors in vivo. The example and FIG. 4 also show that DZ-SIM ester sensitizes prostate carcinoma tumors to a cytotoxic prostate cancer chemotherapeutic drug, Docepaxel (DT). A human prostate tumor xenograft model, 22Rv1 in immune compromised mice, is employed as follows. 1×106 freshly harvested cells of a cultured human prostate carcinoma cell line, 22Rv1, are inoculated s.q. in mice. Mice bearing 22Rv1 tumors (10 tumors/group) are randomized into 7 groups on day-1, and administered drugs by IP (intraperitoneally) at the next day (day-2), and subsequently twice per week, using the following drugs and dosages: a control/vehicle (V, i.e. no drug), DZ (5 µM or 3.9 mg/kg, calculated based on the body weight of mice which averaged 20 grams), SIM (5 µM or 1.1 mg/kg), DZ-SIM (5 µM or 5.5 mg/kg), docetaxel (DT, 8 mg/kg), SIM+DT (drug doses as indicated), and DZ-SIM+DT (drug doses as indicated). Administration is continued for a total of 37 days, and tumor volumes are measured at the indicated times (see FIG. 4). Despite the effectiveness of SIM in inhibiting tumor cell growth in vitro (compare example 1 herein above, and FIG. 1), only DZ-SIM, but not SIM, inhibited the growth of tumors in vivo. DT alone is ineffective in inhibiting 22Rv1 tumor growth in vivo, and SIM alone or in combination with DT also is ineffective, while DZ-SIM is shown to sensitize the therapeutically resistant 22Rv1 tumors to DT. Thus therapeutically resistant prostate tumors can be rendered sensitive by DZ-SIM but not SIM.

Similar results are obtained using DZ-SIM amide, but not SIM alone, in human prostate, lung, and pancreatic cancer models.

Similar results also are obtained for DZ-CIS; DZ-CIS ester, but not CIS, is shown to inhibit the in vivo growth of human kidney (ACHN), and mouse kidney (RENCA) tumors implanted in immune-compromised and immune-intact mice, respectively.

Example 5

The example shows that DZ-CIS (ester or amide) but not CIS alone inhibits in vivo growth of tumors, including in a human lymphoma xenograft model (human Burkitt lymphoma cell line (Namalwa)-derived tumors in mice). Representative results are illustrated in FIG. 5. DZ-CIS is administered to tumors as follows. 15 mice each (NCr Nu/Nu, right panel of FIG. 5, and NOD-SCID, left panel) are injected with Human Burkitt lymphoma cell line, Namalwa cells ($10^3$), producing 4 xenograft tumors per mouse. Mice are randomized in three groups and after tumors reach 100 mm$^3$ are treated 2 times a week with either CIS or DZ-CIS ester in concentrations of either 5 µM (for NOD-SCID) or 10 µM (for NCr Nu/Nu). In comparison to a control (vehicle) and CIS, results show a significant difference in tumor volume in cells treated with DZ-CIS ester compared to CIS or vehicle/control ($p<0.05$).

Example 6

The example shows that DZ-CIS ester is highly effective in sensitizing the antitumor responses of human lymphoma, kidney, and ovarian cancer cell lines that are demonstrated to be CIS-resistant in vitro. As shown in a summary of results in the table below, DZ-CIS ester, but not CIS, inhibits the growth of a series of cultured human lymphoma cell lines (including Daudi, Raji, Namalwa, Ramos and CA-46). The IC50 determined for CIS exceeds 64 µM in all of the lymphoma cell lines, while the IC50 of DZ-CIS is significantly lower, ranging from 0.72 from 2.53 µM, compare table below.

| Cell line | Half maximal inhibitory concentration (IC$_{50}$, µM) at 72 hours | | | |
|---|---|---|---|---|
| | CIS | 95% CI | DZ-CIS Ester | 95% CI |
| Daudi | >64 | ND | 2.53 | 1.833-3.489 |
| Raji | >64 | ND | 1.23 | 1.004-1.502 |
| Namalwa | >64 | ND | 0.72 | 0.512-1.024 |
| Ramos | >64 | ND | 2.40 | 2.029-2.841 |
| CA-46 | >64 | ND | 2.00 | 1.604-2.512 |

Example 7

In the example, it is shown that DZ-CIS ester is highly effective in sensitizing the antitumor responses of human kidney cancer cell lines that are demonstrated to be CIS-resistant in vitro. As shown in a summary of results in the table below, DZ-CIS ester, but not CIS, inhibits the growth of a series of cultured human kidney carcinoma cell lines, including ACHN, Caki-1, 0-786, and SKRC. The IC50 determined for CIS exceeds 64 µM in all of the kidney cancer cell lines, while for DZ-CIS ester the IC50 are significantly lower, ranging from 1.94 to 3.71 µM, compare table below. The significance for all results was $p<0.0001$.

| Cell line | Half maximal inhibitory concentration (IC$_{50}$, µM) at 72 hours | |
|---|---|---|
| | CIS | DZ-CIS |
| ACHN | >64 | 1.94 |
| Caki-1 | >64 | 2.71 |
| o-786 | >64 | 3.71 |
| SKRC | >64 | 3.07 |

Example 8

In the example, it is shown that DZ-CIS ester is highly effective in sensitizing the antitumor responses of human ovarian cancer cell lines demonstrated to be CIS-resistant in vitro. As shown in FIG. 6, CIS-resistant ovarian cancer cells from patients gained or restored CIS sensitivity when exposed to DZ-CIS ester. Two human ovarian cancer cell strains, OV90 and OVCA 433, established from CSMC ovarian cancer patients, are CIS-resistant and have IC50s above 64 µM. These resistant cell strains responded to the antitumor effects of DZ-CIS with a significantly lower IC50 ranging from 3.41 µM to 7.04 µM, compare table below, see FIG. 6. The results of the cell strains corresponded to clinical observations in the respective patients for overcoming therapeutic resistance to CIS, thus allowing a custom-tailored or personalized approach to oncology in patients, first testing tumor cell strains derived from patients in vitro, prior to subjecting patients to DZ-CIS treatment, to improve the success of cancer treatment in patients while avoiding side effects of unnecessary or suboptimal treatments.

Example 9

In the example, it is shown that DZ-CIS ester inhibits the growth and induces apoptosis of human lymphoma and kidney tumor xenografts in mice. A human Burkitt lymphoma cell line, Namalwa is treated with CIS or DZ-CIS ester ("HMCD-Cisplatin") and the level of apoptosis is measured using a CaspaseGlo 3/7 luminescent assay 24 hours after treatment. Cells treated with DZ-CIS ester show significantly higher levels of apoptosis compared with CIS (see FIG. 7, left panel, $p<0.05$). Results are confirmed using Western blotting. Treatment of Namalwa cells with DZ-CIS ester for 24 hours causes more pronounced cleavage of PARP, Caspase 9 and Caspase 3 proteins compared to treatment with CIS. (see FIG. 7, right panel, *$p<0.05$, $p<0.01$, *$p<0.0001$). These results are consistent with the shown antitumor effects of DZ-CIS ester, but not CIS, compare above).

Example 10

In the example, it is shown that DZ-CIS inhibits human lymphoma and kidney tumor growth and induces apoptosis, but protects host normal kidney and liver tissues from damage caused by CIS. CIS, but not DZ-CIS, is shown to cause damages in mouse kidney and liver when given to live mice in vivo. As illustrated in FIG. 8A, immunohistochemical staining shows both apoptosis markers (cleaved caspas-3 and M30) to be elevated in CIS but not in DZ-CIS treated mouse kidney and liver. These normal kidney and liver tissues were obtained from mice harbored with human Burkitt's lymphoma. These comparative results indicate that DZ-CIS protects normal kidney and liver from damage by CIS. As shown in FIG. 8B, DZ-CIS causes increased apoptosis (elevated immunohistochemical markers, cleaved caspase-3 and M30), and decreased cell proliferation (immunohistochemical staining of Ki67), to a degree lesser than that cause by CIS, in a Namalwa human lymphoma xenograft tumors of mice.

Example 11

In the example, it is shown that the in vitro growth of a human kidney cancer cell line, Caki-1, is inhibited by DZ-CIS, but not CIS (see panel A in FIG. 9). These results also show increased apoptosis in human kidney cancer cells exposed to DZ-CIS in a DZ-CIS concentration-dependent manner, by measuring a CaspaseGlo 3/7 luminescent assay 24 hours after treatment (see panel B in FIG. 9). The results show that DZ-CIS, but not CIS, induces elevation of apoptosis related proteins, PARP, Caspase 9 and p53 expression (see panel C in FIG. 9). Results also confirm elevated expression of p53 (a tumor suppressor) in human kidney cancer Caki cells (see panel D in FIG. 9).

Example 12

The example shows protection of kidney from CIS mediated damage by DZ-CIS. In FIG. 10, a histopathology stained with hematoxylin and esosin of mouse kidney from animals treated with CIS (see left panel) and DZ-CIS ester (see right panel) is shown. Similar to host kidney harvested from mice implanted with lymphoma tumors, formalin fixed normal kidney tissues harvested from mice implanted with kidney tumors shows more abundant tubular diallation, intratubular debris and tubular necrosis (left panel, see respective indicators) in host kidney harvested from mice treated with CIS, than in those treated with DZ-CIS (right panel). As illustrated, DZ-CIS protects from more severe kidney damage that occurs with CIS.

Example 13

The table below shows a comparison of IC50s (72 h) of DZ-SIM ester and SIM in cultured prostate, breast, B-cell lymphoma, pancreatic and glioblastoma cancer cell lines, cultured according to standard culturing conditions.

| CELL LINE | DZ-SIM IC50 | SIM IC50 |
|---|---|---|
| PROSTATE CANCER | | |
| 22Rv1 | 4.90 µM | 3.52 µM |
| ARCaP-E | 4.76 µM | 5.61 µM |
| C42 | 4.26 µM | 7.73 µM |
| C4-2B | 1.81 µM | 1.88 µM |
| LNCaP | 1.79 µM | 3.76 µM |
| PC3 | 7.15 µM | 991.3 nM |
| PC3M | 5.19 µM | 248.2 nM |
| BREAST CANCER | | |
| MCF-7 | 9.90 µM | 2.69 µM |
| B-CELL LYMPHOMA (BURKITT) | | |
| Namalwa | 7.15 µM | 13.40 µM |
| Raji | 8.80 µM | 32.45 µM |
| Ramos | 2.74 µM | 13.03 µM |
| Daudi | 5.61 µM | 15 µM |
| PANCREATIC CANCER | | |
| MIAPaCa II | 2.12 µM | 591.7 nM |
| GLIOBLASTOMA | | |
| U87 | 1.32 µM | 505.8 nM |

Example 14

The example shows that DZ-SIM ester, while 5-fold more potent than SIM, DZ-SIM ester synergistically increases CIS cytotoxicity (as determined by % decreased cell viability) over 190-fold (2 µM DZ-SIM ester), see table below. Cancer cells were Ramos, a B-cell lymphoma, cultured as 3-D spheroids, cultured according to their standard culturing conditions. The determined IC50s (72 h) are shown in the table below. The corresponding graphs of % cell viability over the CIS and SIM concentrations, respectively, are shown in FIGS. 11A and B. Similar results are achieved inhibiting pancreatic and breast cancer circulating tumor cells (CTCs) cultured as 3-D spheroids.

| RAMOS | IC50 |
|---|---|
| SIM | 13.03 µM |
| DZ-SIM ester | 2.74 µM |
| CIS | 81.49 µM |
| CIS + DZ-SIM ester | 423 nM |

Example 15

The example shows that DZ-CIS amide exhibits significantly lower absolute IC50 values as shown in the table below, and overcomes resistance to CIS in a number of cell lines tested. Cell lines are cultured according to their standard culturing conditions.

| CELL LINE | DZ-CIS ester IC50 | CIS IC50 |
|---|---|---|
| RENAL CANCER | | |
| ACHN | 11.62 µM | >64 µM |
| Caki-1 | 20.50 µM | >64 µM |
| O-786 | 9.34 µM | >64 µM |
| SKRC | 16.13 µM | >64 µM |
| LUNG CANCER | | |
| H358 | 21.21 µM | >64 µM |
| LIVER CANCER | | |
| HepG2 | >64 µM | >64 µM |
| BREAST CANCER | | |
| MCF-7 | 35.52 µM | 39.53 µM |
| PANCREATIC CANCER | | |
| MIAPaCa II | 10.04 µM | >64 µM |
| U87 | 19.61 µM | >64 µM |
| OVARIAN CANCER | | |
| OV433 | 13.90 µM | >64 µM |
| CAOV-3 | 5.90 µM | 13.42 µM |
| OV90 | 13.93 µM | >64 µM |
| FUOV-1 | 7.52 µM | 27.52 µM |
| PROSTATE CANCER | | |
| ARCaP-M | 29.30 µM | >64 µM |
| PC3M | 24.72 µM | >64 µM |
| ARCaP-E | >64 µM | >64 µM |
| C4-2 | 32.95 | >64 µM |
| C4-2B | 25.47 µM | >64 µM |
| 22Rv1 | 16.84 µM | >64 µM |
| PC3 | 13.86 µM | 48.68 µM |
| LNCaP | >64 µM | >64 µM |
| B- CELL LYMPHOMA (BURKITT) | | |
| Namalwa | >64 µM | >64 µM |
| Raji | >64 µM | >64 µM |
| CA46 | 9.13 µM | >64 µM |
| Ramos | 11.19 µM | >64 µM |
| Daudi | >64 µM | >64 µM |

Example 16

The example shows that DZ-CIS (ester or amide) exhibits more potent antitumor effects in renal cancer and B-cell lymphoma cell lines compared to CIS. While the IC50 determined for CIS is higher than 64 µM, for DZ-CIS ester, the IC50 is below 4 µM for all cancer cell lines (and for some cell lines below 3, 2 or 1 µM), see respective tables below. Cell lines are cultured as follows. Renal cancer cell lines, ACHN, Caki-1, 0-786, SKRC and immortalized B-cell lymphoma cell lines, Namalwa, Raji, CA46, Ramos, Daudi are supplemented with RPMI 1640 medium, 10% fetal bovine serum, 1% PenStrep, and placed in a humidified atmosphere containing 5% $CO_2$ at 37° C. 5,000 cells/well renal cancer cells and 10,000 cells/well lymphoma cells are seeded in 96 well plates in 100 microliter medium/per well for 24 h. Cell lines are exposed to exponentially increasing concentrations of either CIS or DZ-CIS ranging from 0.25 µM to 64 µM for 72 h. Renal cancer cells are fixed with 3.7% paraformaldehyde for 15 minutes and are stained with Crystal violet solution (0.5% in 25% methanol) for 30 minutes. After rinsing with water cell layers are dried and decolorized with Sorenson citrate with shaking for 20 minutes. Light absorption of the extracted supernatant is read at 595 nm. Lymphoma cell growth is evaluated using MTT and cells are incubated for 4 hours. 100 microliters of isopropanol is added, and the extracted supernatant fraction is read at absorption maximum of 595 nm. The results are shown in the tables below.

| Renal cancer cell lines | CIS IC50 | DZ-CIS IC50 | Significance |
|---|---|---|---|
| ACHN | >64 µM | 1.94 µM | P < 0.0001 |
| Caki-1 | >64 µM | 2.71 µM | P < 0.0001 |
| o-786 | >64 µM | 3.71 µM | P < 0.0001 |
| SKRC | >64 µM | 3.07 µM | P < 0.0001 |

| B-cell lymphoma cell lines | CIS, IC50 | DZ-CIS, IC50 | Significance |
|---|---|---|---|
| Daudi | >64 µM | 2.53 µM | P < 0.0001 |
| Raji | >64 µM | 1.23 µM | P < 0.0001 |
| Namalwa | >64 µM | 0.72 µM | P < 0.0001 |
| Ramos | >64 µM | 2.40 µM | P < 0.0001 |
| CA46 | >64 µM | 2.00 µM | P < 0.0001 |

Example 17

The example shows that exposure to DZ-CIS (ester or amide), but not CIS, induces apoptosis in B-cell lymphoma cell lines and renal cancer cell lines. B-cell lymphoma cells (Namalwa) are cultured in RPMI 1640, 10% fetal bovine serum, 1% PenStrep, and placed in a humidified atmosphere containing 5% CO2 at 37° C. 10,000-15,000 cells/well are seeded in 96 white wall well plates in 100 microliter medium/per well for 24 h. Cell lines are then exposed to either CIS or DZ-CIS for 24 hours. 100 microliters of Caspase-Glo 3/7 assay is added and luminescence is then read. Caki-1 cells are cultured in RPMI 1640, 10% fetal bovine serum, 1% PenStrep, and placed in a humidified atmosphere containing 5% CO2 at 37° C. 5,000 cells/well are seeded in 96 white wall well plates in 100 microliter medium/per well for 24 h. Cell lines are then exposed to either CIS or DZ-CIS for 24 hours. 100 microliters of Caspase-Glo 3/7 assay is added and luminescence is then read. As shown in representative diagrams of FIG. 12, DZ-CIS ester is more effective than CIS to induce apoptosis in cancer cells.

Example 18

The example shows that DZ-CIS (ester or amide) is more effective than CIS in inhibiting xenograft renal tumor growth in vivo. Renal cancer cell line (ACHN) is employed in xenografts to immune-compromised mice as follows: 8×106 Caki-1 cells are injected subcutaneously in 4 week old NCR-NU mice. When the tumors grow to 50 $mm^3$, treatment is started with 10 mg/kg NIR-783 dye, 7 mg/kg CIS, and an equimolar dose of DZ-CIS ester, 3 times a week i.p. Tumor size is measured two times a week, using the formula (length×$width^2$)/2 to determine tumor volume. As shown in representative graphs of FIG. 13, DZ-CIS ester lowers the increase of tumor volumes and is more effective than CIS in inhibiting tumor growth in mice.

Example 19

The example shows that DZ-CIS (ester or amide) is more effective than CIS in inhibiting kidney tumor growth in vivo. In a syngeneic mouse model of renal cancer, renal cancer cell line (Renca) is employed in immune-intact Balb/c mice as follows. 500 000 Renca cells are injected subcutaneously in 4 week old BALB/c mice. When the tumors grow to ~50 $mm^3$ in size, treatment is started with 10 mg/kg NIR-783 dye, 7 mg/kg CIS or equimolar dose of DZ-CIS 3 times a week i.p. Tumor size is measured two times a week. Tumor size is measured using a formula (length×$width^2$)/2. As shown in representative graphs of FIG. 14, DZ-CIS ester lowers tumor volumes and is more effective than CIS in inhibiting Renca tumor growth in mice.

Example 20

The example shows that DZ-CIS (ester or amide) is more effective than CIS in inhibiting the growth of B-cell lymphoma. In NCR-NU mice, Namalwa cells are employed and tumor growth is determined as follows: $10^7$ Namalwa cells are injected subcutaneously in 4 week old NCR-NU mice. When the tumors grow to ~50 $mm^3$ in size, treatment is started with 7 mg/kg CIS or equimolar dose of DZ-CIS 3 times a week i.p. Tumor size is measured two times a week. Tumor size is measured using a formula (length×$width^2$)/2. As shown in representative graphs of FIG. 15, DZ-CIS ester lowers tumor volumes and is more effective than CIS in inhibiting tumor growth.

Example 21

The example shows that ovarian tumor cells OV90 and OVCA433 are more sensitive toward the growth inhibitory effect of DZ-SIM, or of DZ-CIS, than to SIM or to CIS, respectively. OV90 and OVCA433 are grown in vitro according to their standard culturing conditions, and an assay such as the crystal violet assay is performed. The IC50 (72 h) for DZ-SIM and DZ-CIS is generally well below 10 µM, as shown in the table below and in FIG. 16, e.g. for DZ-CIS in OV90 and OVCA 433, the IC50 are about 3 and about 7 µM.

| OV90 | IC50 | OVCA 433 | IC50 |
|---|---|---|---|
| DZ-CIS ester | 3.41 µM | DZ-CIS ester | 7.04 µM |
| CIS | >64 µM | CIS | >64 µM |

Example 22

The example shows that DZ-ART greatly enhances tumor growth inhibitory effects compared to ART in a number of tumor types. The table below lists the respective IC50s of 3D cultured circulating tumor cells (CTCs) grown as tumor spheroids (CTC 752-S-1), B-cell lymphoma (Namalwa), castration-resistant prostate cancer (C4-2B), and renal cancer (Caki-1). Cells are cultured according to their standard culturing conditions, and IC50s are determined as described herein-above.

| CELL LINE | ART, IC50 | DZ-ART, IC50 |
|---|---|---|
| CTC 752-S-1 | >64 μM | 1.64 μM |
| Namalwa | >64 μM | 1.30 μM |
| C4-2B | 657 nM | 291 nM |
| Caki-1 | >64 μM | 703 nM |

Example 23

The example shows that DZ-ART but not other DZ-conjugates to cancer therapeutics (DZ-puromycin and DZ-doxorubicin), greatly enhanced cytotoxic effects against cancer cell growth of various cancer cells. Representative results of the determined IC50s are shown in the table below for the indicated cancer cells cultured in vitro, including CTCs (C752-S-1), B-Cell Lymphoma (Namalwa), prostate cancer cells (C4-2B), and renal cancer cells (Caki-1). The cells are cultured according to their standard culturing conditions, and IC50s are determined as described herein-above.

| Cell line | Puromycin IC50 | DZ-Puromycin IC50 | Doxorubicin IC50 | DZ-Doxorubicin IC50 |
|---|---|---|---|---|
| CTC 752-S-1 | 4.87 μM | 31.44 μM | 1.82 μM | 3.41 μM |
| Namalwa | 969 nM | 22.44 μM | 666 nM | 6.23 μM |
| C4-2B | 249 nM | 1.32 μM | 43.10 nM | 206 nM |
| Caki-1 | 740 nM | >64 μM | 880 nM | >64 μM |

Example 24

In the example, the chemical synthesis of DZ-conjugates is shown. Simvastatin was purchased from Ark Pharm, Inc. (Arlington Heights, IL). DZ (1) for the current studies was synthesized as reported earlier. Cisplatin was purchased from MedKoo Biosciences, Inc. (Chapel Hill, NC). Puromycin dihydrochloride was purchased from Alfa Aesar (Tewksbury, MA). All other chemicals and reagents used for the synthetic processes were purchased from standard sources such as Sigma-Aldrich and/or VWR and were of highest quality available. Deionized water (18.2Ω) used for making solutions was obtained from Milli-Q Direct Ultra-pure Water System from Millipore (Billerica, MA, USA). ESI mass spectroscopy analysis was performed on new compounds at Mass Spectrometry and Biomarker Discovery Core facility using a Thermo Fisher LTQ Orbitrap Elite system.

DZ-SIM ester may be synthesized as illustrated in reaction scheme 1 below, e.g. as follows: DZ (1) (407 mg, 0.58 mmol), simvastatin (2) (387 mg, 0.92 mmol), 1-ethyl-3-(3-dimethyllaminopropyl) carbodiie hydrochloride (172 mg, 0.89) and DMAP (65 mg, 0.53 mmol) were mixed and dissolved in anhydrous methylene chloride (15 ml). The resulted mixture was stirred for 18 h. The reaction mixture was concentrated on a rotary evaporator. The residue was dissolved in 5 ml of methanol and purified by C18-RP silica chromatography elution with methanol-water to afford desired product 3 as a dark green solid (269 mg, yield 42%). Mass spectrum (ESI) 1105.58 [M+H]+.

1H NMR (DMSO-d6, 400 MHZ) δ 8.23 (m, 2H), 7.61-7.56 (m, 2H), 7.47 (d, 1H), 7.42-7.36 (m, 3H), 7.29-7.19 (m, 2H), 6.4-0 (d, 1H), 6.24 (d, 1H), 5.89 (d, 1H), 5.73 (m, 1H), 5.71 (s, 1H), 5.43 (m, 1H), 5.12-5.07 (m, 2H), 4.32 (m, 1H), 4.21 (m, 2H), 4.14 (m, 2H), 2.82 (m, 1H), 2.69 (m, 4H), 2.27 (m, 4H), 1.83 (m, 6H), 1.70 (m, 3H), 1.63 (s, 6H), 1.62 (s, 6H), 1.53 (m, 6H), 1.38 (m, 6H), 1.23 (m, 4H), 1.14 (m, 4H), 1.01 (s, 1H), 0.97 (s, 6H), 0.77 (q, 2H), 0.67 (t, 3H). Mass spectrum (ESI) m/z 1105.58 [M+H]+.

Scheme 1 - Illustrative reaction scheme for the synthesis of DZ-SIM ester

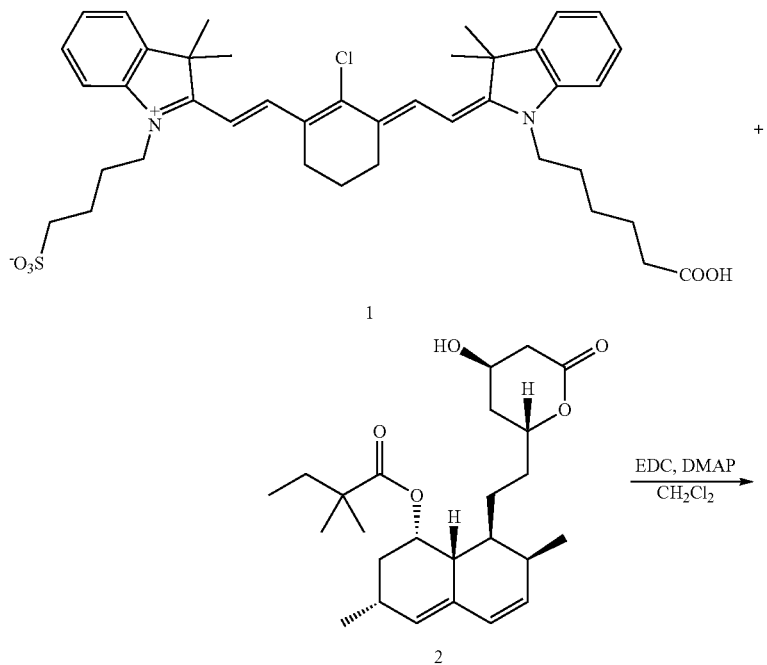

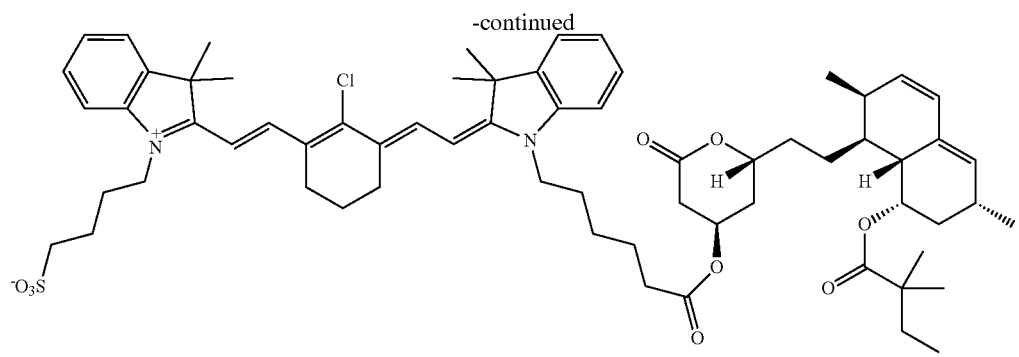

3

DZ-SIM amide may be synthesized as illustrated in the reaction scheme below, e.g. as follows: To a solution of simvastatin (1 g, 2.39 mmol, 1 eq.) in acetonitrile, propane-1,3-diamine (1 mL, 11.95 mmol, 5 eq.) was added. The mixture was refluxed with continuous stirring for 4 h. The solvent was removed under reduced pressure and the product was dried in high vacuum. The resulting product 5 was used without further purification. The mixture of DZ 1 (500 mg, 0.71 mmol) 1-ethyl-3-(3-dimethyllaminopropyl) carbodiie hydrochloride (204 mg, 1.07 mmol) and 1-hydroxy-7-azabenzotriazole (115 mg, 0.85 mmol) were dissolved in 10.0 mL CH$_2$Cl2 solution. The mixture was stirred for 15 min, then compound 5 (350 mg, 0.71 mmol) was added and stirred for additional 2 hours at rt. The solvent was removed under reduced pressure and the product was purified by C18-RP silica chromatography elution with methanol-water to afford desired product 6 as a dark green solid 327 mg (39%). Mass spectrum (ESI) 1179.65 [M+H]+.

Scheme 2 - Illustrative reaction scheme for the synthesis of DZ-SIM amide.

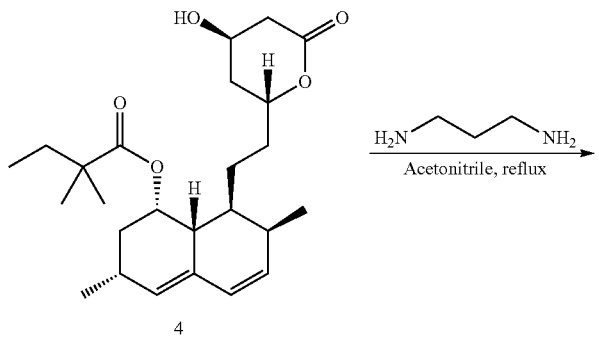

4

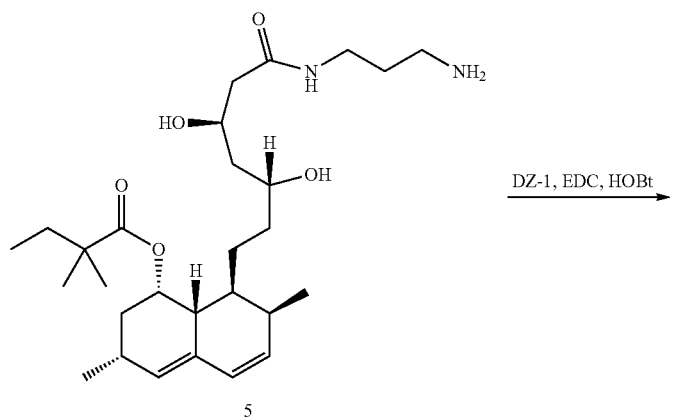

5

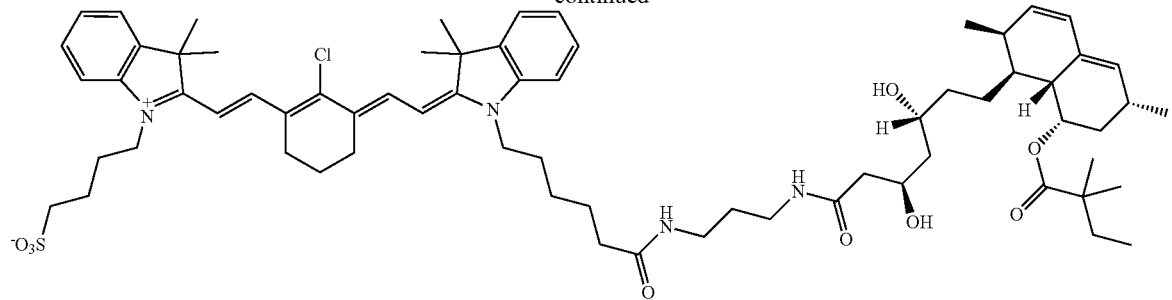

6

DZ-CIS-ester (9) may be synthesized as illustrated in the reaction scheme below, e.g. as follows: Oxoplatin 8 was synthesized according to the literature method (Journal of Inorganic Biochemistry 107 (2012) 6-14). To a suspension of compound 8 (350 mg, 1.05 mmol) in DMSO (20 ml) was added DZ 1 (500 mg, 0.71 mmol) followed by 1-ethyl-3-(3-dimethyllaminopropyl) carbodiie hydrochloride (163 mg, 0.85) and DMAP (80 mg, 0.65 mmol) and the mixture was stirred for 20 h at room temperature to afford green solution. The solution was filtered and the DMSO was removed by lyophilization. The product was purified with C18-RP silica chromatography, elution with methanol-water to afford DZ-CIS 9 as a dark green solid (275 mg, yield 38%). Mass spectrum (ESI) 1020.69 (M+H)+.

1H NMR (DMSO-d6, 400 MHz) δ 8.22 (m, 2H), 7.61-7.56 (m, 2H), 7.48 (d, 1H), 7.39 (m, 3H), 7.26 (m, 2H), 6.37 (d, 1H), 6.24 (d, 1H), 4.15 (m, 4H), 2.68 (m, 4H), 2.15 (m, 2H), 1.80 (m, 4H), 1.70 (m, 6H), 1.63 (s, 6H), 1.62 (s, 6H), 1.51 (m, 2H), 1.40 (m, 2H). Mass spectrum (ESI) m/z 1020.69 (M+H)+.

Scheme 3 - Illustrative reaction scheme for the synthesis of DZ-CIS ester.

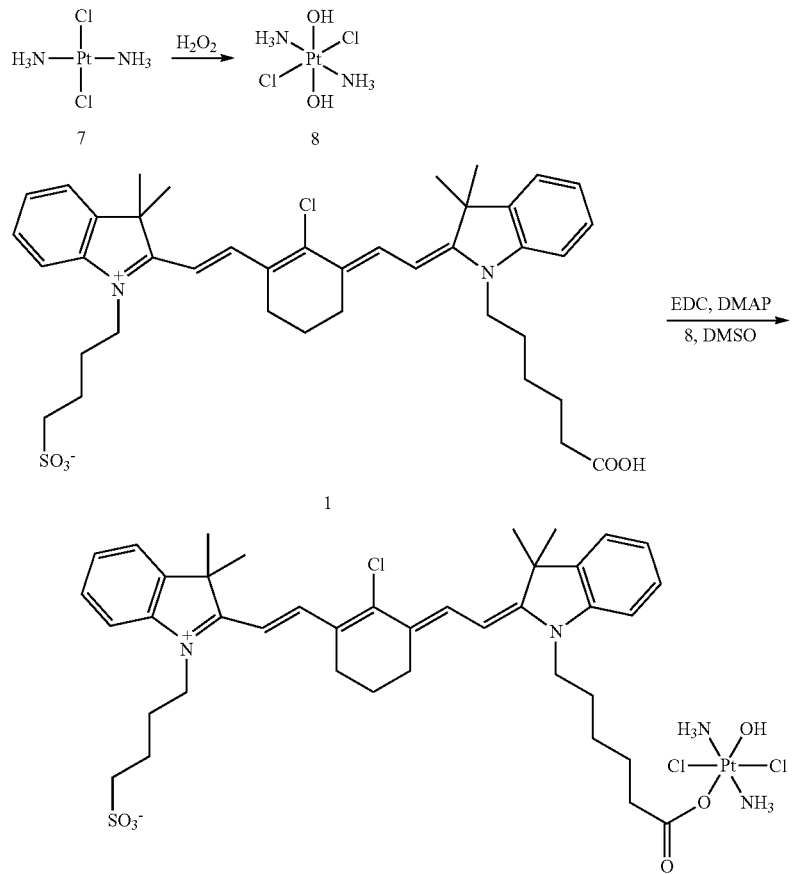

DZ-ART ester may be synthesized as illustrated in the reaction scheme below, e.g. as follows: To a solution of dye 1 (250 mg, 0.35 mmol) in methylene chloride (20 ml) was added dihydroartemisinin 10 (110 mg, 0.39 mmol), 1-ethyl-3-(3-dimethyllaminopropyl) carbodiie hydrochloride (82 mg, 0.43) and DMAP (20 mg, 0.16 mmol) and the mixture was stirred 12 hours at room temperature to afford green solution. The solution was filtered and the solvent was removed under reduced pressure. DZ-ART was purified by C18-RP silica column chromatography elution with methanol-water to afford DZ-ART 11 as a dark green solid 179 mg (52%). 1H NMR (DMSO-d6, 400 MHz) δ 8.22 (m, 2H), 7.58 (m, 2H), 7.47 (d, 1H), 7.38 (m, 3H), 7.25 (m, 2H), 6.38 (d, 1H), 6.25 (d, 1H), 5.60 (d, 1H), 5.50 (s, 1H), 4.55 (m, 2H), 4.21 (m, 4H), 2.68 (m, 6H), 2.35 (m, 2H), 2.17 (m, 2H), 1.86 (m, 6H), 1.73 (m, 6H), 1.64 (s, 6H), 1.63 (s, 6H), 1.57 (m, 2H), 1.37 (m, 2H), 1.24 (m, 2H), 1.22 (s, 3H), 0.84 (m, 3H), 0.67 (m, 2H). Mass spectrum (ESI) m/z 971.46 [M+H]+.

DZ-doxorubicin amide 12 may be synthesized as illustrated in the reaction scheme 5 below, e.g. as follows: The mixture of DZ 1 (103 mg, 0.15 mmol) 1-ethyl-3-(3-dimethyllaminopropyl) carbodiie hydrochloride (40 mg, 0.21 mmol) and 1-hydroxy-7-azabenzotriazole (24 mg, 0.18 mmol) were dissolved in 5.0 ml DMF solution. The mixture was stirred for 15 min, then doxorubicin (85 mg, 0.15 mmol) was added and stirred for additional 15 hours at RT. Ethyl ether (50 ml) was added. The precipitate collected and purified by C18-RP silica chromatography elution with methanol-water to afford desired product 12 as a dark green solid 83 mg (46%). 1H NMR (DMSO-d6, 400 MHz) δ 8.18 (m, 2H), 7.90 (m, 2H), 7.62 (m, 2H), 7.49 (m, 2H), 7.41 (m, 2H), 7.32 (s, 1H), 7.29 (m, 1H), 7.25 (m, 1H), 6.37 (d, 1H), 6.24 (d, 1H), 5.45 (s, 1H), 5.18 (s, 1H), 4.92 (m, 1H), 4.80 (m, 1H), 4.67 (m, 1H), 4.52 (m, 2H), 4.21 (m, 2H), 4.11 (m, 2H), 3.93 (s, 3H), 2.96 (s, 1H), 2.63 (m, 4H), 2.15 (m, 2H), 2.00 (m, 4H), 1.76 (m, 6H), 1.64 (s, 6H), 1.63 (s, 6H), 1.56

Scheme 4. Synthesis of DZ-ART ester conjugate

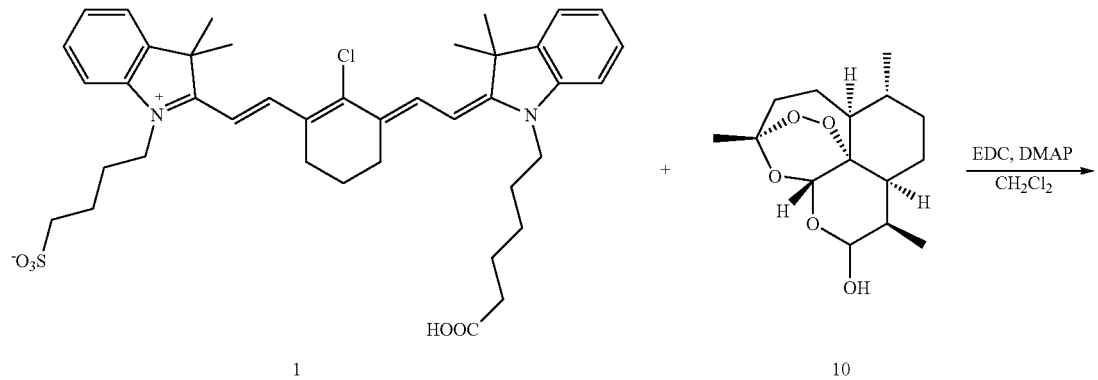

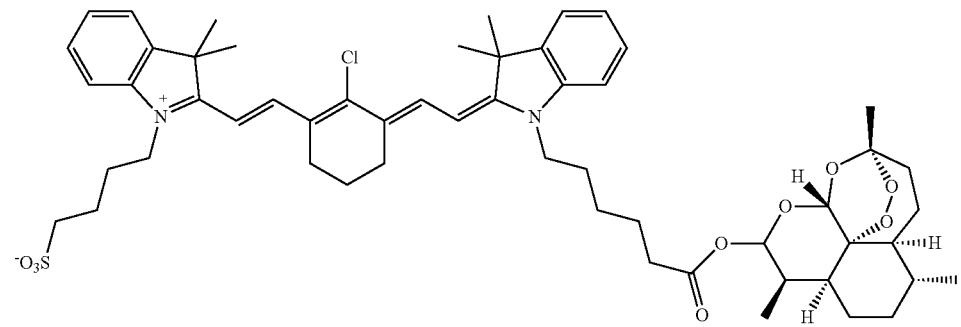

(s, 3H), 1.55 (s, 3H), 1.48 (m, 2H), 1.20 (m, 2H), 1.08 (m, 2H). Mass spectrum (ESI) m/z 1230.47 [M+H]+.

Scheme 5. Synthesis of DZ-doxorubicin

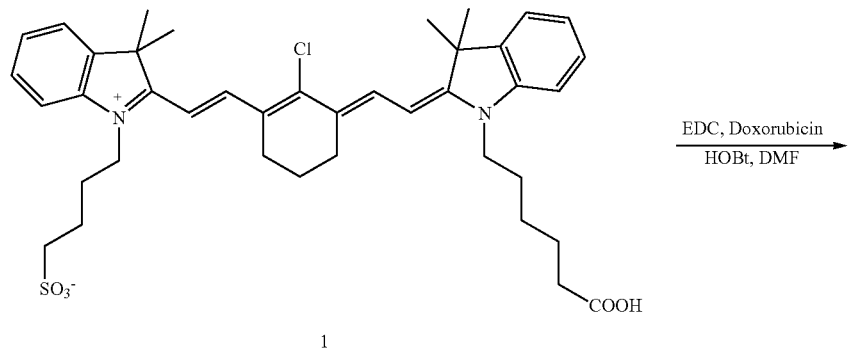

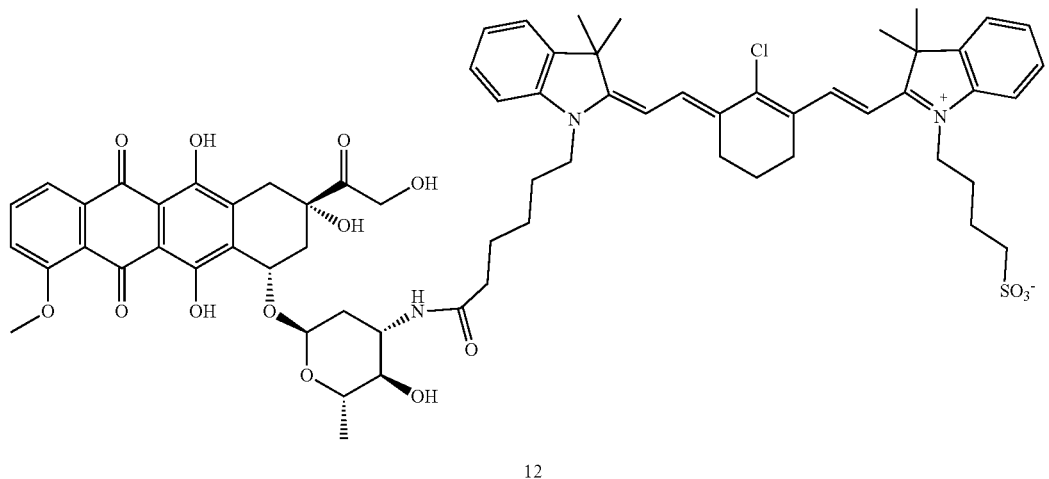

DZ-puromycin amide 14 may be synthesized as illustrated in the reaction scheme 6 below, e.g. as follows: The mixture of DZ 1 (130 mg, 0.18 mmol) 1-ethyl-3-(3-dimethyllaminopropyl) carbodiie hydrochloride (52.8 mg, 0.28 mmol) and 1-hydroxy-7-azabenzotriazole (29.8 mg, 0.22 mmol) were dissolved in 5.0 ml DMF solution. The mixture was stirred for 15 min, then puromycin dihydrochloride (340 mg, 0.18 mmol) was added and stirred for 15 hours at rt. Ethyl ether (50 ml) was added. The precipitate was collected and purified by C18-RP silica chromatography elution with methanol-water to afford desired product 14 as a dark green solid 94 mg (44%). Mass spectrum (ESI) m/z 1158.52 [M+H]+.

Scheme 6. Synthesis of DZ-puromycin amide

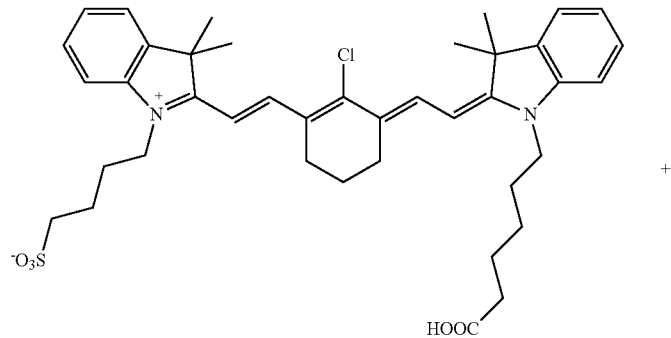

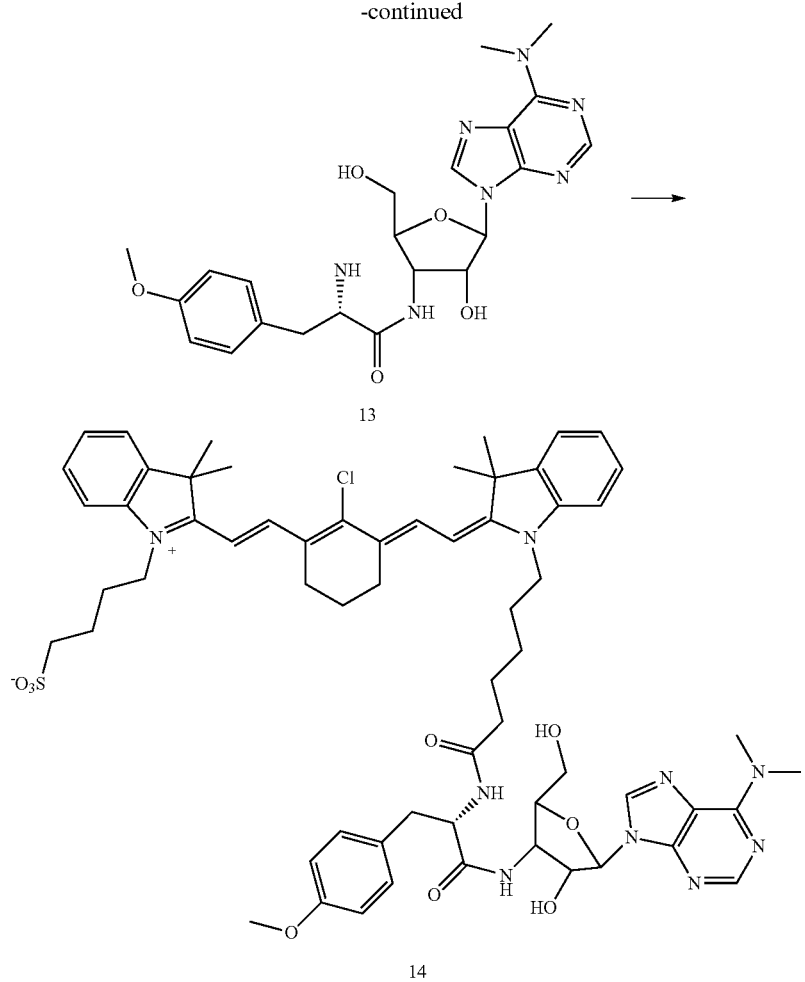

While multiple embodiments are disclosed, still other embodiments of the present invention will become apparent to those skilled in the art from this detailed description. There may be aspects of this invention that may be practiced without the implementation of some features as they are described. It should be understood that some details have not been described in detail in order to not unnecessarily obscure the focus of the invention. The invention is capable of myriad modifications in various obvious aspects, all without departing from the spirit and scope of the present invention. Accordingly, the drawings and descriptions are to be regarded as illustrative rather than restrictive in nature.

The invention claimed is:

1. A sensitizer compound which is a DZ-DRG amide or ester conjugate, wherein a DZ-residue of formula FI or FII, via an amide or ester bond, is linked to the residue of a drug (DRG); wherein the conjugated drug (DRG) is selected from the group consisting of Simvastatin (SIM), Artemisinin (ART), Doxorubicin (DOX), Paclitaxel (PAC), a statin, and a therapeutically functional derivative thereof, and wherein the DZ residue is selected from the group consisting of an amide DZ residue of formula I below

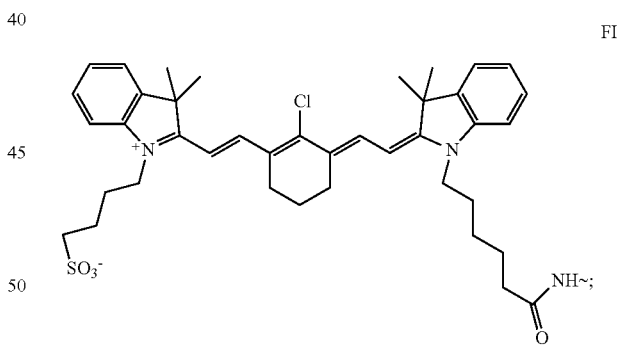

and an ester residue of formula II below

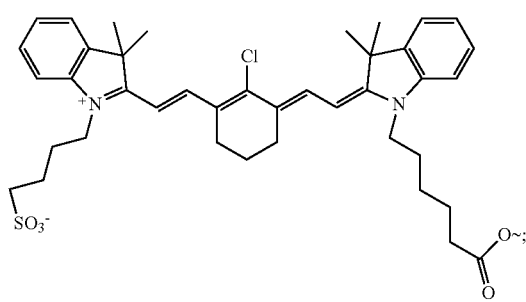

wherein ~ represents a point of attachment to the conjugated drug (DRG).

2. The sensitizer compound of claim 1, wherein the sensitizer is selected from group consisting of: DZ-SIM ester, DZ-SIM amide, DZ-ART ester, and DZ-ART amide.

3. The sensitizer compound of claim 1, wherein the conjugated DRG is a statin drug selected from the group consisting of simvastatin, atorvastatin, fluvastatin, lovastatin, pitavastatin, pravastatin, and rosuvastatin.

4. A pharmaceutical composition comprising a sensitizer compound which is a DZ-DRG amide or ester conjugate and at least one pharmaceutically acceptable carrier; wherein a DZ-residue of formula FI or FII, via an amide or ester bond, is linked to the residue of a DRG drug;
wherein the conjugated DRG of the sensitizer is selected from the group consisting of Simvastatin (SIM), Artemisinin (ART), a statin, and a therapeutically functional derivative thereof, and wherein the DZ residue is selected from the group consisting of an amide DZ residue of formula I below

FI

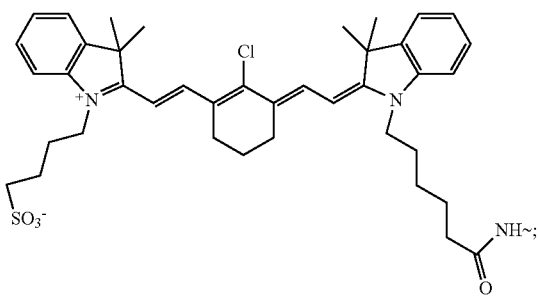

and an ester DZ reside of formula II below

FII

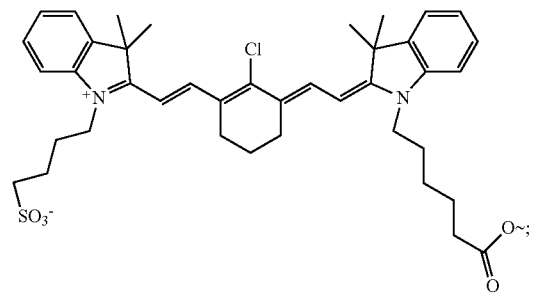

wherein ~ represents a point of attachment to the conjugated drug (DRG).

5. The pharmaceutical composition of claim 4, wherein the sensitizer is selected from the group consisting of DZ-SIM ester, DZ-SIM amide, DZ-ART ester, and DZ-ART amide.

6. The pharmaceutical composition of claim 4, wherein the concentration of the sensitizer compound and its carrier are adapted to provide the sensitizer to pre-cancerous cells or cancer cells of a tumor type generally responsive, and optionally resistant, to a RPT selected from the group consisting of Cisplatin (CIS), Gemcitabine (GEM), Doxorubicin (DOX), Paclitaxel (PAC), Docetaxel (DT), a platin-based compound, and a therapeutically functional derivative thereof, in sufficient concentration to sensitize the tumor or cancer cells to the RPT.

7. The pharmaceutical composition of claim 4 as part of a kit of one or more pharmaceutical compositions, the kit comprising (1) the DRG-conjugated sensitizer (2) a RPT, and (3) instructions for coordinated administration of the sensitizer and the RPT in a common administration regimen, wherein (1) and (2) each are in a suitable form for delivery and optionally comprise one or more accessory pharmaceutical ingredient, and wherein the RPT is selected from the group consisting of Cisplatin (CIS), Gemcitabine (GEM), Doxorubicin (DOX), Paclitaxel (PAC), Docetaxel (DT), a platin-based compound, and a therapeutically functional derivative thereof.

8. The composition of claim 7 wherein for (1) the DRG sensitizer is selected from the group consisting of DRG-SIM and DRG-ART.

9. The composition of claim 7 wherein for (1) the DRG sensitizer is selected from the group consisting of DRG-SIM and DRG-ART, and for (2) the RPT is CIS.

10. A method of sensitizing tumor, cancer, or precancerous cells present in a subject to the treatment with a RPT drug;
wherein the sensitizer is a DZ-DRG amide or ester conjugate comprising a conjugated DRG; wherein the DRG is selected from the group consisting of Cisplatin (CIS), Simvastatin (SIM), Artemisin (ART), Doxorubicin (DOX), Paclitaxel (PAC), a platin-based compound, a statin, and a therapeutically functional derivative thereof;
wherein the RPT is selected from the group consisting of Cisplatin (CIS), Gemcitabine (GEM), Doxorubicin (DOX), Paclitaxel (PAC), Docetaxel (DT), a platin-based compound, and a therapeutically functional derivative thereof;
and wherein if the RPT is present in form of a DZ-conjugated RPT, and a platin-based compound or Cisplatin (CIS) is selected as DRG, then the selected platin-based or CIS DRG is not also selected as RPT in the DZ-conjugated RPT;
and wherein the DZ residue is selected from the group consisting of a DZ amide of formula FI, and a DZ ester of formula FII, shown below:

FI

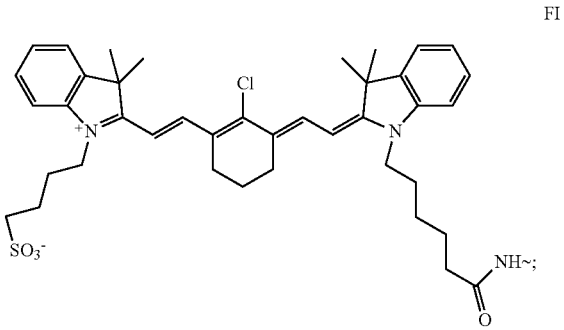

-continued

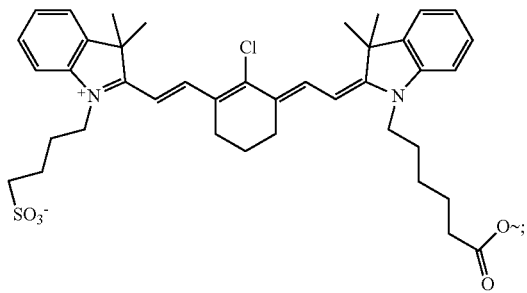

FII wherein ~ represents a point of attachment to the conjugated drug (DRG); and the method comprising exposing a plurality of tumor, cancer or pre-cancerous cells to the RPT by administering a sensitizer compound to a subject in need of treatment with the RPT, in an amount and concentration sufficient to increase the sensitivity of the cells to the RPT.

11. The method of claim 10, comprising co-administering, or administering in a coordinated schedule adapted to increase the sensitivity of the cells to the RPT, and in an amount and concentration sufficient for the RPT to provide an anticancer effect in presence of, or together with, the sensitizer.

12. The method of claim 10, wherein the RPT is selected from the group consisting of CIS, and a platin-based compound (PT), and wherein the sensitizer is selected from the group consisting of DZ-SIM ester, DZ-SIM amide, DZ-ART ester, and a DZ-ART amide.

13. The method of claim 10, wherein the DRG of the sensitizer is a statin selected from the group consisting of atorvastatin, fluvastatin, lovastatin, pitavastatin, pravastatin, and rosuvastatin.

14. The method of claim 10, wherein the DRG of the sensitizer is a platin-based compound selected from the group consisting of cisplatin, carboplatin (also known as CBDCA), and dicycloplatin (also known as DCP), oxaliplatin, satraplatin, picoplatin, nedaplatin, triplatin, lobapatin, heptaplatin, and lipoplatin.

15. The method of claim 10, wherein the tumor, cancer, or precancerous cells are cells of one or more of lung cancer, non-small cell lung cancer (NSCLC), small cell lung cancer (SCLC), pancreatic cancer, kidney cancer, and prostate cancer.

16. The method of claim 10, wherein prior to administration of one or more of sensitizer or RPT, the method comprises the further steps of: isolating cancer cells from a patient; culturing the isolated cancer cells in a suitable medium that allows cell growth; exposing the cancer cells to one or more of DZ-RPT sensitizer and RPT, and determining sensitivity of the cells to one or more of sensitizer and RPT.

17. The composition of claim 7 wherein for (1) the DRG sensitizer is selected from the group consisting of DRG-SIM and DRG-ART, and for (2) the RPT is Gemcitabine (GEM), or a therapeutically functional derivative thereof.

18. The composition of claim 7 wherein for (1) the DRG sensitizer is DRG-SIM, and for (2) the RPT is Gemcitabine (GEM), or a therapeutically functional derivative thereof.

19. The method of claim 10, wherein the DRG for conjugation in the DRG-sensitizer is selected from the group consisting of Simvastatin (SIM), Artemisinin (ART), Doxorubicin (DOX), Paclitaxel (PAC), a statin, and a therapeutically functional derivative thereof.

* * * * *